US006696548B2

(12) United States Patent
Morris et al.

(10) Patent No.: US 6,696,548 B2
(45) Date of Patent: Feb. 24, 2004

(54) ANTIBODIES FOR RECOGNITION OF ALK PROTEIN TYROSINE/KINASE RECEPTOR

(75) Inventors: Stephan W. Morris, Memphis, TN (US); A. Thomas Look, Boston, MA (US)

(73) Assignee: St. Jude Children's Research Hospital, Memphis, TN (US)

( * ) Notice: Subject to any disclaimer, the term of this patent is extended or adjusted under 35 U.S.C. 154(b) by 128 days.

(21) Appl. No.: 09/827,949

(22) Filed: Apr. 9, 2001

(65) Prior Publication Data

US 2001/0021505 A1 Sep. 13, 2001

Related U.S. Application Data

(60) Division of application No. 09/670,827, filed on Sep. 28, 2000, now Pat. No. 6,451,997, which is a continuation of application No. 09/100,089, filed on Jun. 19, 1998, now Pat. No. 6,174,674, which is a division of application No. 08/542,363, filed on Oct. 12, 1995, now Pat. No. 5,770,421, which is a continuation-in-part of application No. 08/160,861, filed on Dec. 3, 1993, now Pat. No. 5,529,925.

(51) Int. Cl.$^7$ .............................................. C07K 16/00
(52) U.S. Cl. .................................................... 530/387.9
(58) Field of Search ...................................... 530/387.9

(56) References Cited

U.S. PATENT DOCUMENTS

| 4,873,191 A | 10/1989 | Wagner et al. ............ 435/172.3 |
| 5,529,925 A | 6/1996 | Morris et al. ............. 435/252.3 |
| 5,770,421 A | 6/1998 | Morris et al. ................ 435/194 |
| 5,942,412 A | * 8/1999 | Prager et al. |

FOREIGN PATENT DOCUMENTS

| EP | 0 252 685 | 6/1993 |
| WO | WO 87/07305 | * 12/1987 |
| WO | WO 91/05064 | 4/1991 |

OTHER PUBLICATIONS

Ngo et al.; in The Protein Folding Problem and Tertiary Structure Prediction, 1994, Merz et al., (ed.), Birkhauser, Boston, MA, pp. 433 and 492–495.*
Coleman et al. (Research in Immunology, 1994; 145(1): 33–36).*
Abaza et al. (Journal of Protein Chemistry, vol. 11, No. 5, 1992, pp. 433–444).*
Lederman et al. (Molecular Immumology 28: 1171–1181, 1991).*
Li et al. (PNAS 77: 3211–3214, 1980).*
Mikayama et al. (PNAS, 1993. 90: 10056–10060).*
Bendayan (J. Histochem. Cytochem. 1995; 43: 881–886).*
Bost et al. (Immunol. Invest. 1988; 17:577–586).*
Basler, K., and Hafen, E., "Control of Photoreceptor Cell Fate by the sevenless Protein Requires a Functional Tyrosine Kinase Domain," *Cell 54*:299–311, Cell Press, Cambridge, MA (1988).

Beckmann, R., et al., "Nuclear Substrates of Protein Kinase C," *Eur. J. Biochem. 210*:45–51, Blackwell Science Ltd., Berlin, Germany (Nov. 1992).
Bitter, M.A., et al., "Morphology in Ki–1(CD30)–Positive Non–Hodgkin's Lymphoma Is Correlated with Clinical Features and the Presence of a Unique Chromosomal Abnormality, t(2;5) (p23;q35)," *Am. J. Surg. Pathol. 14*:305–316, Raven Press, Ltd., New York, NY (1990).
Borer, R.A., et al., "Major Nucleolar Proteins Shuttle Between Nucleus and Cytoplasm," *Cell 56*:379–390, Cell Press, Cambridge, MA (1989).
Bowtell, D.D.L., et al., "Nucleotide sequence and structure of the sevenless gene of *Drosophila melanogaster*," *Genes & Devel. 2*:620–634, Cold Spring Harbor Laboratory Press, Cold Spring Harbor, NY (1988).
Brinkman, A., et al., "Isolation and characterization of a cDNA encoding the low molecular weight insulin–like growth factor binding protein (IBP–1)," *EMBO J. 7*:2417–2423, IRL Press Limited, Oxford, England (1988).
Chan, P.K., et al., "The major phosphorylation site of nucleophosmin (B23) is phosphorylated by a nuclear kinase II," *Biochem. J. 270*:549–552, London Portland Press On Behalf Of The Biochemical Society, London, England (1990).
Chan, W.–Y., et al., "Characterization of the cDNA Encoding Human Nucleophosmin and Studies of Its Role in Normal and Abnormal Growth," *Biochemistry 28*:1033–1039, American Chemical Society, Washington D.C. (1989).
Chen, J., et al., "The proto–oncogene c–ros codes for a transmembrane tyrosine protein kinase sharing sequence and structural homology with sevenless protein of *Drosophila malanogaster*," *Oncogene 6*:257–264, Macmillan Press Ltd., London, England (1991).
Cleary, M.L., "Oncogenic Conversion of Transcription Factors by Chromosomal Translocations," *Cell 66*:619–622, Cell Press, Cambridge, MA (1991).
Coulier, F., et al., "Mechanism of Activation of the Human trk Oncogene," *Mol. Cell. Biol. 9*:15–23, American Society for Microbiology, Washington, D.C. (1989).
Dumbar, T.S., et al., "Interaction of Nucleolar Phosphorotein B23 with Nucleic Acids," *Biochemistry 28* (24):9495–9501, American Chemical Society, Washington D.C. (1989).

(List continued on next page.)

*Primary Examiner*—Christina Chan
*Assistant Examiner*—Michail Belyavskyi
(74) *Attorney, Agent, or Firm*—Sterne Kessler Goldstein & Fox PLLC

(57) ABSTRACT

The present invention is based on the identification and sequence determination of a novel gene, ALK, which is fused to the gene encoding nucleophosmin (NPM) in translocations present in t(2;5) lymphoma cells. Based on homologies to other proteins, the amino acid sequence of the polypeptide encoded by the ALK (Anaplastic Lymphoma Kinase) gene is a membrane-spanning protein tyrosine kinase (PTK)/receptor. Antibodies to the ALK PTK/receptor and methods utilizing such antibodies are described, as are methods of using the ALK gene to isolate ligands for the ALK PTK/receptor.

14 Claims, 30 Drawing Sheets

OTHER PUBLICATIONS

Dërkop, H., et al., "Molecular Cloning and Expression of a New Member of the Nerve Growth Factor Receptor Family That Is Characteristic for Hodgkin's Disease," *Cell* 68:421–427, Cell Press, Cambridge, MA (Feb. 1992).

Ebina, Y., et al., "The Human Insulin Receptor cDNA: The Structural Basis for Hormone–Activated Transmembrane Signalling," *Cell* 40:747–758, Cell Press, Cambridge, MA (1985).

Feuerstein, N., and Mond, J.J., "'Numatrin,' a Nuclear Matrix Protein Associated with Induction of Proliferation in B Lymphocytes," *J. Biol. Chem.* 262:11389–11397, American Society for Biochemistry and Molecular Biology, Inc., Baltimore, MD (1987).

Feuerstein, N., and Mond, J.J., "Identification of a Prominent Nuclear Protein Associated With Proliferation of Normal and Malignant B Cells," *J. Immunol.* 139:1818–1822, American Association of Immunologists, Baltimore, MD (1987).

Feuerstein, N., et al., "Identification of Numatrin, the Nuclear Matrix Protein Associated with Induction of Mitogenesis, as the Nucleolar Protein B23," *J. Biol. Chem.* 263:10608–10612, American Society for Biochemistry and Molecular Biology, Inc., Baltimore, MD (1988).

Feuerstein, N., et al., "The Nuclear Matrix Protein, Numatrin (B23), is Associated with Growth Factor–induced Mitogenesis in Swiss 3T3 Fibroblasts and with T Lymphocyte Proliferation Stimulated by Lectins and Anti–T Cell Antigen Receptor Antibody," *J. Cell Biol.* 107:1629–1642, The Rockfeller University Press, New York, NY (1988).

Feuerstein, N., and Randazzo, P.A., "In Vivo and in Vitro Phosphorylation Studies of Numatrin, a Cell Cycle Regulated Nuclear Protein, in Insulin–Stimulated NIH 3T3 HIR Cells," *Exp. Cell Res.* 194:289–296, Academic Press, Inc., New York, NY (1991).

Greer, J.P., et al., "Clinical Features of 31 Patients with Ki–1 Anaplastic Large–Cell Lymphoma," *J. Clin. Oncol.* 9(4):539–547, Lippincott Williams & Wilkins, Hagerstown, MD (1991).

Hanks, S.K., et al., "The Protein Kinase Family: Conserved Features and Deduced Phylogeny of the Catalytic Domains," *Science* 241:42–52, Association for the Advancement of Science, Washington D.C. (1988).

Hernandez–Verdun, D., "The Nucleolus Today," *J. Cell Sci.* 99:465–471, The Company of Biologists Limited, Great Britain (1991).

Julkunen, M., et al., "Primary Structure of Human Insulin–Like Growth Factor–Binding Protein/Placental Protein 12 and Tissue–Specific Expression of its mRNA," *FEBS Letts.* 236(2):295–302, Federation of European Biochemical Societies, Amsterdam, Netherlands (1988).

Kadin, M.E., "Ki–1–Positive Anaplastic Large–Cell Lymphoma: A Clinicopathologic Entity?, " *J. Clin. Oncol.* 9(4):533–536, Lippincott Williams & Wilkins, Hagerstown, MD (1991).

Kaneko, Y., et al., "A Novel Translocation, t(2;5) (p23;q35), in Childhood Phagocytic Large T–Cell Lymphoma Mimiking Malignant Histiocytosis," *Blood* 73:806–813, W. B. Saunders, Philadelphia, PA (1989).

Kozma, S.C., et al., "Activation of the Receptor Kinase Domain of the trk Oncogene by Recombination with Two Different Cellular Sequences," *EMBO J.* 7:147–154, IRL Press Limited, Oxford, England (1988).

Krolewski, J.J., and Dalla–Favera, R., "The ltk Gene Encodes a Novel Receptor–Type Protein Tyrosine Kinase," *EMBO J.* 10:2911–2919, IRL Press Limited, Oxford, England (1991).

Lawrence, J.B. et al., "Interphase and Metaphase Resolution of Different Distances Within the Human Dystrophin Gene," *Science* 249:928–932, Association for the Advancement of Science, Washington D.C. (1990).

Le Beau, M.M., et al., "The t(2;5) (p23;q35): A Recurring Chromosomal Abnormality in Ki–1–Positive Anaplastic Large Cell Lymphoma," *Leukemia* 3:866–870, Williams and Wilkins, Baltimore, MD (1989).

Lee, Y.–L., et al., "Insulin–Like Growth Factor (IGF) Binding Protein Complementary Deoxyribonucleic Acid from Human HEP G2 Hepatoma Cells: Predicted Protein Sequence Suggests an IGF Binding Domain Different from Those of the IGF–I and IGF–II Receptors," *Mol. Endocrinol.* 2:404–411, The Endocrine Society, Baltimore, MD (1988).

Martin–Zanca, D., et al., "A Human Oncogene Formed by the Fusion of Truncated Tropomyosin and Protein Tyrosine Kinase Sequences," *Nature* 319:743–748, Macmillan Publishers Ltd., London England (1986).

Mason, D.Y., et al., "CD30–Positive Large Cell Lymphomas ('Ki–1 Lymphoma ') Are Associated with a Chromosomal Translocation Involving 5q35," *Br. J. Haematol.* 74:161–168, Blackwell Scientific Publications, Oxford, England (1990).

Matsushime, H., et al., "Human c–ros–1 Gene Homologous to the v–ros Sequence of UR2 Sarcoma Virus Encodes for a Transmembrane Receptorlike Molecule," *Mol. Cell. Biol.* 6:3000–3004, American Society for Microbiology, Washington, D.C. (1986).

Morris, S.W., et al., "Reassignment of the Human CSFI Gene to Chromosome 1p13–p21," *Blood* 78:2013–2020, W. B. Saunders, Philadelphia, PA (1991).

Oskam, R., et al., "Frequent Generation of Oncogenes by in vitro Recombination of TRK Protooncogene Sequence," *Proc. Natl. Acad. Sci. USA* 85:2964–2968, National Academy of Sciences of the USA, Washingtion, D.C. (1988).

Pawson, T., "Tyrosine Kinases and Their Interactions with Signalling Proteins," *Curr. Opin. Genet. Devel.* 2:4–12, Current Biology, Ltd., London, England (Feb. 1992).

Peter, M., et al., "Identification of Major Nucleolar Proteins as Candidate Mitotic Substrates of cdc2 Kinase," *Cell* 60:791–801, Cell Press, Cambridge, MA (1990).

Rabbits, T.H., "Translocations, Master Genes, and Differences Between the Origins of Acute and Chronic Leukemias," *Cell* 67:641–644, Cell Press, Cambridge, MA (1991).

Rimokh, R., et al., "A Translocation Involving a Specific Breakpoint (q35) on Chromosome 5 is Characteristic of Anaplastic Large Cell Lymphoma ('Ki–1 Lymphoma ')," *Br. J. Haematol.* 71:31–36, Blackwell Scientific Publications, Oxford, England (1989).

Saltman, D.L., et al., "Isolation of Region–Specific Cosmids from Chromosome 5 by Hybridization with Microdissection Clones," *Nucl. Acids Res.* 20:1401–1404, Oxford University Press, Oxford, England (Mar. 1992).

Saltman, D.L., et al., "A Physical Map of 15 Loci on Human Chromosome 5q23–q33 by Two–Color Fluorescence in Situ Hybridization," *Genomics* 16:726–732, Academic Press, Inc., San Diego, CA (Jun. 1993).

Sambrook, J., et al., *Molecular Cloning: A Laboratory Manual*, 2nd Ed., Cold Spring Harbor, NY: Cold Spring Harbor Laboratory Press, Cold Spring Harbor, NY pp. 12.2–12.3, 16.2 (1989).

Sawyers, C.L., et al., "Leukemia and The Disruption of Normal Hematopoiesis," *Cell 64:*337–350, Cell Press, Cambridge, MA (Sep. 1992).

Schlessinger, J., and Ullrich, A., "Growth Factor Signaling by Receptor Tyrosine Kinases," *Neuron 9:*383–391, Cell Press, Cambridge, MA (Sep. 1992).

Schmidt–Zachmann, M.S., et al., "A Constitutive Nucleolar Protein Identified as a Member of the Nucleoplasmin Family," *EMBO J. 6(7)*:1881–1890, IRL Press Limited, Oxford, England (1987).

Schmidt–Zachman, M.S., and Franke, W.W., "DNA Cloning and Amino Acid Sequence Determination of a Major Constituent Protein of Mammalian Nucleoli," *Chromosoma (Berl) 96:*417–426, Springer–Verlag, Berlin, Germany (1988).

Selleri, L., et al., "Molecular Localization of the t(11;22) (q24;q12) Translocation of Ewing Sarcoma by Chromosomal in situ Suppression Hybridization," *Proc. Natl. Acad. Sci. USA 88:*887–891, National Academy of Sciences of the USA, Washington D.C. (1991).

Smith, C.A., et al., "CD30 Antigen, a Marker for Hodgkin's Lymphoma, is a Receptor Whose Ligand Defines an Emerging Family of Cytokines with Homology to TNF," *Cell 73:*1349–1360, Cell Press, Cambridge, MA (Jul. 1993).

Smith, K.A., "Interleukin–2: Inception, Impact, and Implications," *Science 240:*1169–1176, Association for the Advancement of Science, Washington D.C. (1988).

Stansfeld, A.G., et al., "Updated Kiel Classification for Lymphomas," *Lancet 1:*292–293, The Lancet Ltd., New York, NY (1988).

Stein, H., and Dallenbach, F., "Diffuse Large Cell Lymphomas of B and T Cell Type," in: *Neoplastic Hematopathology*, Knowles, D.M., ed., Williams & Wilkins, Baltimore, MD, pp. 675–714 (Jun. 1992).

Stryer, L., "Eukaryotic Genes Can Be Transcribed and Translated in Bacterial Cells," in *Biochemistry, 2nd* Ed., W.H. Freeman and Company, New York, NY pp. 765–766 (1981).

Taylor, S.S., et al., "Structural Framework for the Protein Kinase Family," *Ann. Rev. Cell Biol. 8:*429–462, Annual Reviews, Inc., Palo Alto, CA (Nov. 1992).

Tkachuk, D.C., et al., "Detection of bcr–abl Fusion in Chronic Myelogenous Leukemia by in Situ Hybridization," *Science 250:*559–562, Asociation for the Advancement of Science, Washington D.C. (1990).

Toyoshima, H., et al., "Differently Spliced cDNAs of Human Leukocyte Tyrosine Kinase Receptor Tyrosine Kinase Predict Receptor Proteins With and Without a Tyrosine Kinase Domain and a Soluble Receptor Protein," *Proc. Natl. Acad. Sci. USA 90:*5404–5408, National Academy of Sciences of the USA, Washington, D.C. (Jun. 1993).

Trask, B.J., et al., "Mapping of Human Chromosome Xq28 by Two–Color Fluorescence In Situ Hybridization of DNA Sequences to Interphase Cell Nuclei," *Am. J. Hum. Genet. 48:*1–15, University of Chicago Press, Chicago, IL (1991).

Ullrich, A., et al., "Human Insulin Receptor and Its Relationship to the Tyrosine Kinase Family of Oncogenes," *Nature 313:*756–761, Macmillan Publishers Ltd., London, England (1985).

Ullrich, A., et al., "Insulin–Like Growth Factor I Receptor Primary Structure: Comparison with Insulin Receptor Suggests Structural Determinants that Define Functional Specificity," *EMBO J. 5:*2503–2512, IRL Press Limited, Oxford, England (1986).

Vecchi, V., et al., "Anaplastic Large Cell Lymphoma (Ki–1+/CD30+) in Childhood," *Med. Pediatr. Oncol. 21:*402–410, Wiley–Liss, Inc. (Dec. 1993).

Watson, J.D., et al., eds., "The Unexpected Expression of Many Yeast Gene in *E. coli*," in *Molecular Biology of the Gene*, vol. I, pp. 597–598, The Benjamin/Cummings Publishing Company, Inc., Menlo Park, CA (1987).

Ziemiecki, A., et al., "Oncogenic Activation of the Human trk Proto–Oncogene by Recombination with the Ribosomal Large Subunit Protein L7a," *EMBO J. 9:*191–196, IRL Press Limited, Oxford, England (1990).

Bradley, A., et al., "Modifying the Mouse: Design and Desire," *Bio/Technology 10:*534–539, Nature Publishing Co., New York, NY (May 1992).

Bullrich, F., et al., "Nucleophosmin (NPM) Gene Rearrangements in Ki–1–positive Lymphomas," *Cancer Res. 54:*2873–2877, American Association For Cancer Research (Jun. 1994).

Downing, J.R., et al., "Molecular Detection of the (2;5) Translocation of Non–Hodgkin's Lymphoma by Reverse Transcriptase–Polymerase Chain Reaction," *Blood 85:*3416–3422, W. B. Saunders, Philadelphia, PA (Jun. 1995).

Hartig, P.R., "The Use of Cloned Human Receptors for Drug Design," In: *Medications Development: Drug Discovery, Databases, and Computer–Aided Drug Design*, NIDA Research Monograph 134, Rapaka, R.S. and Hawks, R.L., eds., U.S. Dept. of Health and Human Services, National Institute on Drug Abuse, Rockville, MD, pp. 58–65 (Jan. 1993).

Ladanyi, M., et al., "Reverse Transcriptase Polymerase Chain Reaction for the Ki–1 Anaplastic Large Cell Lymphoma–Associtated t(2;5) Translocation in Hodgkin's Disease," *Amer. J. Pathol. 145:*1296–1300, American Society for Investigative Pathology, Philadelphia, PA (Dec. 1994).

Mathew, P., et al., "Localization of the murine homolog of the anaplastic lymphoma kinase (Alk) gene on mouse Chromosome 17," *Cytogenet. Cell Genet. 70:*143–144, Karger, Basel, Switzerland (Apr. 1995).

Morris, S.W. et al., "The t(2;5) of Anaplastic Large Cell Lymphoma Generates a Fusion Gene Encoding the Catalytic Domain of ALK, A Novel Tyrosine Kinase," *Blood 82:*Abstract No. 333, W. B. Saunders, Philadelphia, PA (Nov. 1993).

Morris, S.W., et al., "Fusion of a Kinase Gene, ALK, to a Nucleolar Protein Gene, NPM, in Non–Hodgkin's Lymphoma," *Science 263:*1281–1284, Association for the Advancement of Science, Washington D.C. (Mar. 1994).

Proffitt, J., "New LSI® ALK (Anaplastic Lymphoma Kinase) FISH Probe Detects 2p23 Rearrangements in Non-Hodgkin's Lymphoma," *Vysions 3:*6–7, Downers Grove IL (1998).

Uhlmann, E., and Peyman, A., "Antisense Oligonucleotides: A New Therapeutic Principle," *Chem. Rev. 90:*544–584, American Chemical Society, Washington D.C. (1990).

Yung, B.Y.–M., and Chan, P.–K., "Identification and characterization of a hexameric form of nucleolar phosphoprotein B23," *Biochim. Biophys. Acta 925:*74–82, Elsevier Science Publishers B.V., Amsterdam, Netherlands (1987).

Downing, J.R., et al., "Molecular detection of the Ki–1 positive large cell lymphoma–associated t(2:5) by reverse transcriptase polymerase chain reaction," *Modern Pathol.* 7:107A, Abstract 618, Lippincott Williams & Wilkins (Jan. 1994).

Maru, Y., et al., "Evolution, expression, and chromosomal location of a novel receptor tyrosine kinase gene, eph," *Mol. Cell Biol.* 8:3770–3776, American Society for Microbiology, Washington, D.C. (1988).

Maru, Y., et al., "Human ltk: gene structure and preferential expression in human leukemic cells," *Oncogene Res.* 5:199–204, Harwood Academic Publishers GmbH, New York, NY (1990).

Morris, S.W., et al., "Sequence Correction," *Science* 267:316–317, Association for the Advancement of Science, Washington D.C. (Jan. 1995).

Stratgene Catalog, "Gene Characterization Kits," Stratagene Corporation, La Jolla, CA p. 39 (1988).

Zhang, X.T. et al., "Isolation and characterization of a molecular cDNA clone of a human mRNA from interferon-treated cells encoding nucleolar protein B23, numatrin," *Biochem. Biophys. Res. Commun.* 164:176–184, Academic Press, Inc. (1989).

* cited by examiner

MEDSMDMDMSPLRPQNYLFGCELKADKDYHFKVDNDENEHQL·SLRTVSLGAGAKDELHIVEAEAMNYEGSPIKVTLATLK 80
                                          NPM ALK
MSVQPTVSLGGFEITPPVVLRLKCCGSGPVHISGQHLVVYRRKHQELQAMQMELQSPEYKLSKLRTSTIMTDYNPNYCFAG 180
KTSSISDLKEVPRKNITLIRGLGHGAFGEVYEGQVSGMPNDPSPLQVAVKTLPEVCSEQDELDFLMEALIISKFNHQNIV 240
RCIGVSLQSLPRFILLELMAGGDLKSFLRETRPRPSQPSSLAMLDLLHVARDIACGCQYLEENHFIHRDIAARNCLLTCP 320
GPGRVAKIGDFGMARDIYRASYYRKGGCAMLPVKWMPPEAFMEGIFTSKTDTWSFGVLLWEIFSLGYMPYPSKSNQEVLE 400
FVTSGGRMDPPKNCPGPVYRIMTQCWQHQPEDRPNFAIILERIEYCTQDPDVINTALPIEYGPLVEEEKVPVRPKDPEGV 481
PPLLVSQQAKREEERSPAAPPPLPTTSSGKAAKKPTAAEVSVRVPRGPAVEGGHVNMAFSQSNPPSELHKVHGSRNKPTS 561
LWNPTYGSWFTEKPTKKNNPIAKKEPHDRGNLGLEGSCTVPPNVATGRLPGASLLLEPSSLTANMKEVPLFRLRHFPCGN 641
VNYGYQQQGLPLEAATAPGAGHYEDTILKSKNSMNQPGP 680

FIG.2A

VNIKHHYLNCSHCEVDECHMDPESHVICFCDHGTVLAEDGVSCIVSPTPEPHLPL SLILSVVTSALVAALVLAFSGIMI VYRRKHQELQAMQMELQSPEY

1    MGAIGLLWLLPLLSTAAVGSGMGTGQRAGSPAAGSPLQPREPLSYSRLQRKSLAVDFVVPSLFRVYARDLLLPPSSSELKAGRPEARGSLALDCAPLLRLLGPAPGVSWTAGSPAPAEA    120

121  RTLSRVLKGGSVRKLRRAKQLVLELGEEAILEGCVGPPGEAAVGLLQFNLSELFSWWIRQEGRLRIRLMPEKKASEVGREGRLSAAIRASQPRLLFQIFGTGHSSLESPTNMPSPSPDY    240

241  FTWNLTWIMKDSFPFLSHRSRYGLECSFDFPCELEYSPPLHDLRNQSWMRRIPSEEASQMDLLDGPCAERSKEMPRGSFLLNTSADSKHTILSPWMRSSSEHCTLAVSVRHLQPSGR    360

361  YIAQLLPHNEAAREILLMPTPCKHCGWTVLQCRIGRPDNPFRVALEYISSGNRSLSAVDFFALKNCSEGTSPGSKMALQSSFTCMNGTVLQLGQACDFHQDCAQGEDESQMCRKLPVGFYQ    480

481  NFEDGFCCWTQGTLSPHTPQWQVRTLKDARFQDHQDHALLLSTTDVPASESATVTSATFPAPIKSSPCELRMSWLIRGVLRQNVSLVLVENKIGKEQGRMVWHVAAYEGLSLWQWMVLPL    600

601  LDVSDRFWLQMVAWWGQGSRAIVAFDNISISLDCYLTISGEDKILQNTAPKSRNLFERNPNKELKPGENSPRQTPIFDPTVHWLFTTCCASGPHCPTQAQCNNAYQNSNLSVEVGSEGPL    720

721  KGIQIWKVPATDTYSISGYGAAGCKGGKNTMMRSHGVSVLGIFNLEKDDMLYILVGQQEDACPSTNQLIQKVQIGENNVIEEEIRVNRSVHEWAGGGGGGGATYVFKMKDGVPVPLII    840

841  AAGGGGGGRAYGACKTDTFHPERLENNSSVLGLNGNSGAAGGGGWNDNTSLLWAGKSLQECATGGHSCPQAMKKWGWETRGGFGGGGGGCSSGGGGGGYIGGNAASNNDPEMDGEDGVSFIS    960

---NPM-ALK fusion junction

961  PLGILYTPALKVMEGHGEVNIKHYLNCSHCEVDECHMDPESHKVIQFCDHCGTVLAEDGVSCIVSPTPEPHLPLSLILSVVTSALVAALVLAFSGIMIVYRRKHQELQAMQMELQSPEYKL   1080

1081 SKLRTSTIMTDYNPNYCFAGKTSSISDLKEVPRKNITLIRGLGHGAFGEVYEGQVSGMPNDPSPLQVAVKTILPEVCSEQDELDFLMEALIISKFNHQNIVRCIGVSLQSLPRFILLELMA   1200

1201 GGDLKSFLRETRPRPSQPSSLAMLDLLHVARDIACGCQYLEENHFIHRDIAARNCLLTCPGPGRVAKIGDFGMARDIYRASYRKGGCAMLPVKWMPPEAFMEGIFTSKTDTWSFGVLLW   1320

1321 EIFSLGYMPYPSKSNQEVLEFVTSGGRMDPPKNCPGPVYRIMTQCWQHQPEDRPNFAIILERIEYCTQDPDVINTALPIEYGPLVEEEKVPVRPKDPEGVPPLLVSQQAKREEERSPAA   1440

1441 PPPLPTTSSGKAAKKPTAAEVSVRVPRGPAVEGGHVNMAFSQSNPPSELHKVHCSRNKPTSLWNPTYGSWFTEKPTKKNNPIAKKEPHDRGNLGLEGSCTVPPNVATGRLPGASLLLEPS   1560

1561 SLTANMKEVPLFRLRHFPCGNVNYGYQQQGLPLEAATAPGAGHYEDTILKSKNSMNQPGP   1620

FIG. 3B

```
  S   L   G   G   F   E   I   T   P   P   V   L   R   L   K   C   G   S   G
TCCCTTGGGGGCTTTGAAATAACACCACCAGTGGTCTTAAGGTTGAAGTGTGGTTCAGGG

NPM | ALK
  P   V   H   I   S   G   Q   H   L   V | V   R   K   H   Q   E   L   Q
CCAGTGCATATTAGTGGACAGCACTTAGTAGTGTACCGCGGAAGCACCAGGAGCTGCAA

A   M   Q   M   E   L   Q   S   P   E   Y   K   L   S   K   L   R   T   S
GCCATGCAGATGGAGCTGCAGAGCCCTGAGTACAAGCTGAGCAAGCTCCGCACCTCG
```

FIG. 5B

FIG.7A  FIG.7B 
FIG.7C 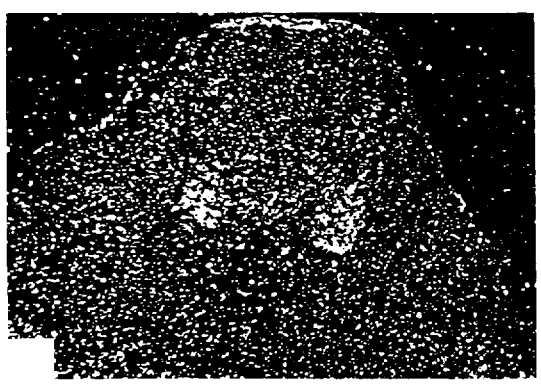 FIG.7D 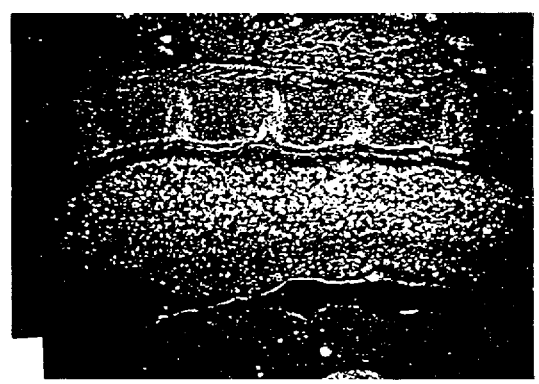
FIG.7E

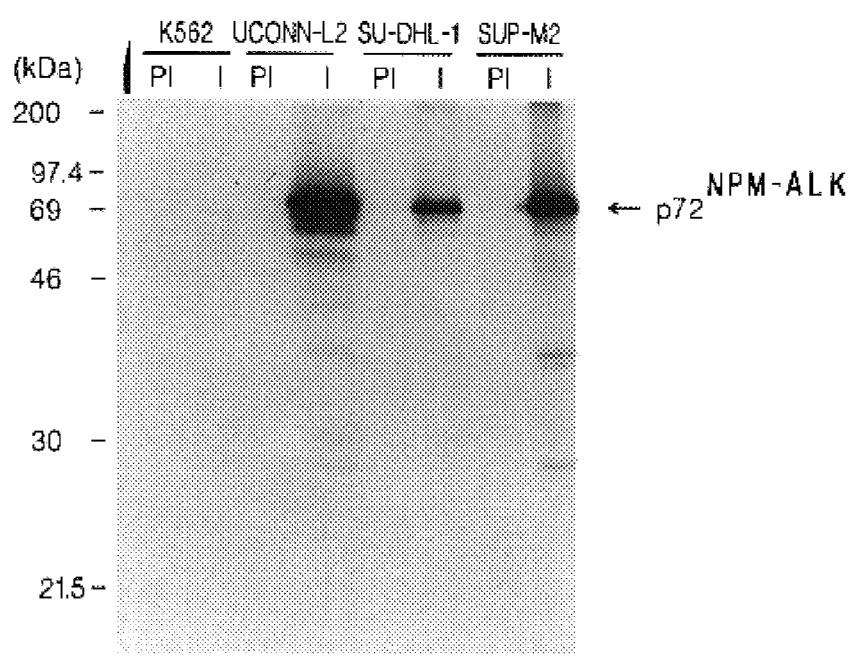
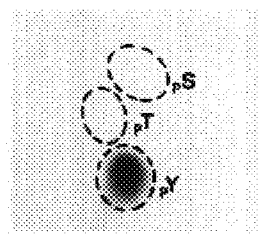
FIG.12A
FIG.12B

FIG.18A
FIG.18B
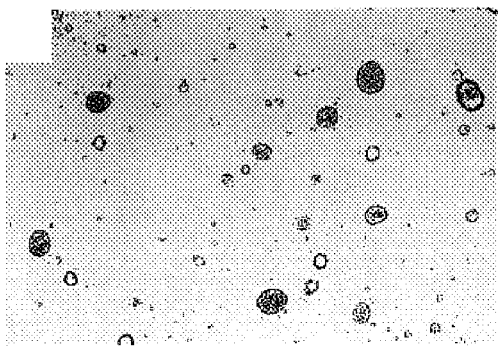
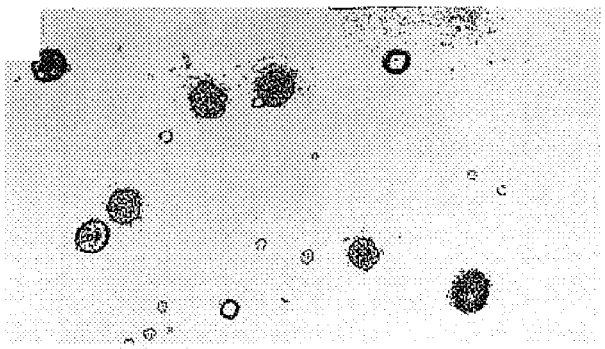
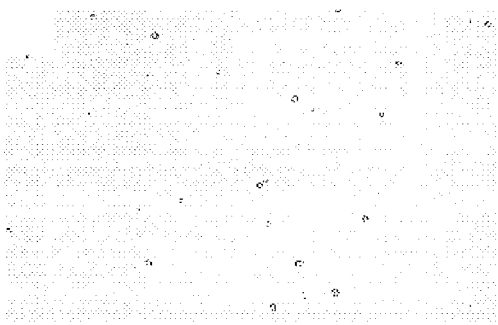
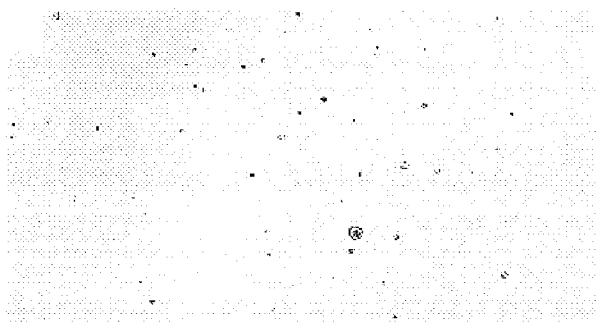
FIG.18C
FIG.18D

ANTIBODIES FOR RECOGNITION OF ALK PROTEIN TYROSINE/KINASE RECEPTOR

RELATED APPLICATIONS

This application is a divisional of application Ser. No. 09/670,827, filed on Sep. 28, 2000 now U.S. Pat. No. 6,451,997, which is a continuation of Ser. No. 09/100,089, filed on Jun. 19, 1998. Now U.S. Pat. No. 6,174,674, which is a divisional of application Ser. No. 08/542,363, filed on Oct. 12, 1995, now U.S. Pat. No. 5,770,421, which is a continuation in part of application Ser. No. 08/160,861, filed on Dec. 3, 1993, now U.S. Pat. No. 5,529,925.

STATEMENT AS TO RIGHTS TO INVENTIONS MADE UNDER FEDERALLY-SPONSORED RESEARCH AND DEVELOPMENT

Part of the work performed in this invention was made with the use of government funding by way of a grant from the National Institutes of Health and National Cancer Institute, Grant Number K08CA0 1702. Therefore, the government has certain rights in this invention.

BACKGROUND OF THE INVENTION

1. Field of the Invention

The present invention is directed to the field of molecular genetics of cancer. Specifically, the present invention relates to human lymphomas in which a translocation between chromosomes 2 and 5 (referred to in the art as "t(2;5)") has occurred. On a molecular level, the DNA rearrangement in t(2;5) results in the fusion of the known NPM gene with a novel gene named ALK (Anaplastic Lymphoma Kinase) that encodes a protein tyrosine kinase (PTK).

2. Related Art

Chromosomal abnormalities are frequently associated with malignant diseases. In a number of instances, specific chromosomal translocations have been characterized, which generate fusion genes encoding proteins with oncogenic properties (Sawyers et al., Cell 64:337–350 (1991)). Perhaps the best example of genetic characterization of a malignant disease is provided by the analysis of the chromosomal abnormalities unique to different subsets of non-Hodgkin's lymphoma (NHL). The NHL subset commonly referred to as large cell lymphoma (which comprises ~25% and 40% of NHL in children and adults, respectively) has historically been the most ill-defined because of its marked cytological, immunological and clinical heterogeneity.

Approximately one-third of large cell lymphomas (10% of all NHL) contain the t(2;5)(p23;q35), usually as the only cytogenetic abnormality (R. Rimokh et al., Br. J. Haematol. 71:31–36 (1989); D. Mason et al., Br. J. Haematol. 74:161–168 (1990); H. Stein and F. Dallenbach, in Neoplastic Hematopathology, D. M. Knowles, ed., Williams & Wilkins, Baltimore (1992), pp.675–714), suggesting that rearrangement of cellular proto-oncogenes on these chromosomes contributes to lymphomagenesis.

The majority oft(2;5)-positive lymphomas (70–75%) express T-lymphoid markers, although usually in the aberrant, incomplete fashion characteristic of T-cell malignancies (e.g., preservation of CD2 and CD4 with infrequent expression of CD3) (M. E. Kadin, J. Clin. Oncol. 12:884–887 (1994); J. T. Sandlund et al., Blood 84:2467–2471 (1994)). Less commonly, these neoplasms bear B-cell markers (~15%) or have a null phenotype with neither B- nor T-antigen expression (10%). Lymphomas with the t(2;5) typically involve lymph nodes, skin, lung, soft tissue, bone and the gastrointestinal tract, and arise predominantly from activated T lymphocytes (Y. Kaneko et al., Blood 73:806–813 (1989); M. M. Le Beau et al., Leukemia 3:866–870 (1989); R. Rimokh et al., Br. J. Haematol. 71:31–36 (1989); D. Y. Mason et al., Br. J. Haematol. 74:161–168 (1990); M. A. Bitter Am. J. Surg. Pathol. 14:305–316 (1990); M. E. Kadin, J. Clin. Oncol. 9:533–536 (1991); J. P. Greer et al., J. Clin. Oncol. 9:539–547 (1991); V. Vecchi et al., Med. Pediatr. Oncol. 21:402–410 (1993)). The malignant cells express IL-2 receptors and CD30 (Ki-1) antigen, a receptor for a newly described member of the tumor necrosis factor ligand family (H. Durkop et al., Cell 68:421–427 (1992); C. A. Smith et al., Cell 73:1349–1360 (1993)). By the updated Kiel lymphoma classification, most tumors with the t(2;5) are classified as anaplastic large cell non-Hodgkin's lymphomas (A. G. Stansfeld et al., Lancet 1:292–293 (1988)). These tumors typically behave as aggressive, high-grade NHL with most patients having advanced stage disease at presentation. From 30% to 40% of patients eventually succumb to their disease despite aggressive therapeutic intervention.

SUMMARY OF THE INVENTION

Disclosed herein is the cloning and sequencing of human nucleic acid sequences which are rearranged in the t(2;5) (p23;q35) chromosomal translocation event which occurs in human t(2;5) lymphoma. The rearrangement was found to bring sequences from the nucleolar phosphoprotein gene (the NPM gene) on chromosome 5 q35 to those from a previously unidentified protein tyrosine kinase (PTK) gene (the ALK gene) on chromosome 2p23. The sequence of the novel ALK gene and ALK protein, as well as the sequence of the t(2;5) fusion gene and fusion protein (the NPM/ALK gene and NPM/ALK protein, respectively), are disclosed herein.

The NPM gene encodes a highly conserved nonribosomal RNA-binding protein that shuttles ribosomal ribonucleoproteins (rRNPs) between the nucleolus and the cytoplasm; rRNPs associate with NPM in the nucleolus, are carried to the cytoplasm, and are released at the maturing ribosomes (M. S. Schmidt-Zachmann et al., EMBO J. 6:1881–1890 (1987); M. S. Schmidt-Zachmann et al., Chromosoma. 96:417–426(1988)). Bidirectional movement of NPM between the nucleolus and cytoplasm has been elegantly demonstrated in studies monitoring the equilibration of the protein between nuclei present in chicken-mouse heterokaryons (R. A. Borer et al., Cell 56:379–390 (1989)). Several groups have shown that NPM can exist in the cell as either a monomer or a homo-oligomeric hexamer, associated in a head-to-head/tail-to-tail fashion; it is not clear which form of the protein moves between the nucleolus and cytoplasm (M. S. Schmidt-Zachmann et al., Chromosoma. 96:417–426 (1988); B.Y. Yung et al., Biochim. Biophys. Acta. 925:74–82 (1989); Q. R. Liu et al., Eur. J. Biochem. 200:715–721 (1991)).

The NPM/ALK fusion gene was initially identified in anaplastic large cell lymphomas. However, its presence has since been observed in a significant number of diffuse and immunoblastic large cell cases as well. Expression of the NPM/ALK fusion gene in lymphoid cell lines which are otherwise dependent on IL-3 for growth results in transformed cells which proliferate in an IL-3-independent manner. This result suggests a means by which the NPM/ALK fusion acts to promote tumorigenesis and provides for methods of culturing lymphoid cells in vitro in the absence of IL-3.

Utilizing the sequences of the NPM/ALK fusion gene, the present invention provides methods of identifying the presence of nucleic acids containing the NPA/ALK fusion by means such as nucleic acid hybridization and detection methods (e.g., "Southerns," "Northerns" and the like) fluorescence in situ hybridization (FISH) and detection methods, or polymerase chain reaction (PCR) amplification and detection methods. Such methods can be used in, inter alia, to determine if particular cells or tissues express ALK or NPM/ALK coding sequences, or diagnostic assays designed to determine, for example, if a mammal has cancer or a genetic predisposition to (i.e., is at an increased risk of developing) cancer.

Detection methods utilizing the ALK sequences of the invention as probes are further used to isolate and clone ALK sequences and genes from a variety of mammalian species, and the ALK sequences and genes so prepared provide the foundation for further embodiments of the invention. For example, a "Southern" assay is used to identify clones from a library of murine cDNA sequences using human ALKDNA sequences as a radiolabeled probe. These ALK-positive clones are isolated, and the nucleotide sequence of the mouse cDNA inserted into the vector in these clones is determined using any standard method of nucleotide sequencing known to those of skill in the art. The human and murine ALK nucleotide sequences are aligned by computer program or by hand, and regions of identical or, at least well-conserved, nucleotide sequence between the ALK genes of the two species are identified. These identical/conserved sequences are used to design oligonucleotides which function as ALK-specific primers to be used in PCR amplifications in which the template DNA is genomic DNA or cDNA from a third mammal (i.e., one which is neither a mouse nor a human) in order to obtain ALK DNA, that can be cloned and sequenced, from said third mammal. Alternatively, human or murine ALK sequences, or oligonucleotides derived therefrom, are labeled and used as probes to identify ALK-positive clones in libraries prepared from genomic DNA or cDNA from a third mammal. In like fashion, ALK sequences from any mammal can be prepared and tested for its use in any appropriate embodiment of the present invention. Furthermore, cDNAs derived from alternatively-spliced human ALK transcripts (see Example 2(B)) are prepared by reverse transcription, cloning and identification by hybridization according to methods known in the art (see, for example, Chapters 7–8 in Sambrook et al., eds., *Molecular Cloning*, Cold Spring Harbor Press, Cold Spring Harbor, N.Y. (1989).

The nucleotide sequences of the ALK, as well as the NPM/ALK, genes of the invention are also utilized to design and prepare agents which specifically inhibit the expression of the ALK and/or NPM/ALK genes in cells for therapeutic and other purposes. For example, antisense oligonucleotides and ribozymes specific for ALK and/or NPM/ALK are prepared using the nucleotide sequences of the invention.

The ALK and NPM/ALK genes of the invention are further utilized in methods of producing ALK or NPM/ALK proteins, respectively, by introduction of the appropriate gene into a host/vector expression system. Of course, ALK and NPM/ALK proteins or polypeptides derived therefrom may also be produced by other means known in the art such as, for example, chemical synthesis or in vitro transcription/translation.

The ALK and NPM/ALK proteins and polypeptide sequences of the invention, whether produced by host/vector systems or otherwise, can be used to produce antibodies which (a) specifically recognize (i.e., bind) the NPM/ALK protein, (b) specifically recognize the ALK protein or (c) specifically recognize both the ALK and NPM/ALK proteins.

The present invention further provides methods of detecting the presence of the ALK and/or NPM/ALK proteins which are based on antibody detection systems. For example, because the NPM/ALK fusion protein is expressed in t(2;5) lymphoma cells, but the normal ALK protein is not, antibodies which recognize the fusion protein can be used to detect the presence of the NPM/ALK fusion protein in a sample containing such cells, or to detect the presence oft(2;5) lymphoma cells in a tissue sample suspected of containing such cells.

The invention further provides compartmentalized kits to receive in close confinement one or more containers containing the reagents used in one or more of the above described detection methods.

The present invention further provides methods for isolating and identifying the natural ligand(s) bound by the NPM/ALK or ALK proteins, and for identifying derivatives of the ligand(s) that act to inhibit the action of the NPM/ALK and/or ALK proteins.

Finally, the present invention provides for transgenic animals, preferably mice, which (a) lack a functional copy of the endogenous ALK gene (e.g., ALK "knockout" mice), (b) contain and express an NPM/ALK fusion protein derived from an exogenous source and subsequently introduced into the genome of the animal or (c) both lack a functional ALK gene and express an introduced NPM/ALK fusion gene. Methods of utilizing such mice to identify and test carcinogenic or therapeutic compositions are also described herein.

BRIEF DESCRIPTION OF THE FIGURES

FIGS. 2A–2C Deduced amino acid sequence of(A) NPM/ALK (SEQ ID NO:4) and (B) the portion of ALK immediately adjacent to the fusion junction (SEQ ID NO:7), and (C) homology comparison of the catalytic domain of ALK with other tyrosine kinases of the insulin receptor subfamily (SEQ ID NOs:12–39). In panel A, solid circles indicate possible protein kinase C phosphorylation sites, the dashed underline signifies a potential metal-binding domain, and the two arrows represent the boundaries of the ALK catalytic domain. In panel B, the arrow indicates the position in the normal ALK sequence at which NPM/ALK fusion occurs, and amino acid residues (hydrophobicity greater than 1.5) comprising a putative transmembrane domain are boxed. In panel C, the amino acid residues of the tyrosine kinase catalytic domains are aligned, with gaps indicated by dashes. Shaded boxes indicate residues in the related tyrosine kinases that are identical to amino acids of ALK. All sequences are for human proteins, excluding 7leis (*Drosophila melanogaster* Sevenless) (J. J. Krolewski et al., *EMBO J.* 10.2911–2919 (1991); H. Toyoshima et al., *Proc. Natl. Acad. Sci. USA* 90:5404–5408 (1993); D. Martin-Zanca et al., *Nature* 319:743–748 (1986); H. Matsushime el al., *Mol. Cell. Biol.* 6:3000–3004 (1986); J. M. Chen et al., *Oncogene* 6:257–264 (1991); K. Basler et al., *Cell* 54:299–311 (1988); D. D. Bowtell eta!., *Genes and Development* 2:620–634 (1988); A. Ullrich et al., *EMBOJ.* 5:2503–2512 (1986); A. Ullrich et al., *Nature* 313:756–761 (1985); Y. Ebina et al., *Cell* 40:747–758 (1985)).

FIGS 3A–3B Schematic representation (A) and deduced amino acid sequence (SEQ ID NO:2) (B) of a human ALK cDNA clone. (A) The thick bar represents the coding sequences of the 6,226 bp insert of human ALK cDNA clone RMS17-2. The putative signal peptide (SP, hatched box), transmembrane (TM, solid box), and tyrosine kinase (TK, stippled box) domains are indicated. Cysteine residues (solid circles) and consensus N-glycosylation sites (inverted triangles) present in the extracellular domain are indicated. The thin open bars on either end represent 5' and 3' non-coding sequences. (B) Deduced amino acid sequence encoded by ALK cDNA clone RMS17-2 (SEQ ID NO:2). The putative signal peptide (amino acids 1–26) is underlined. Cysteine residues within the extracellular domain are circled. Consensus N-glycosylation sites (N-X-S/T) are enclosed by open boxes. The transmembrane domain (residues 1031–1058) is highlighted by a shaded box. Horizontal arrows flank the tyrosine kinase catalytic domain (residues 1123–1376). The position at which ALK is truncated by the t(2;5) to produce NPM-ALK is also shown ("NPM-ALK fusion junction").

FIGS 5A–5C (A) Southern blot analysis of NPM/ALK and NPM RNA-PCR products. Total RNAs (1 µg) from t(2;5)-positive cell lines (SU-DHL-1, SUP-M2 and UCONN-L2; lanes 3–5) and diagnostic samples (Pts. 1–4, lanes 6–9) were analyzed; in addition, RNAs from the t(2;5)-negative B- and T-lymphoid leukemia cell lines (NALM-6 and CEM, respectively; lanes 1 and 2) and the Rh30 rhabdomyosarcoma cell line (lane 10), which lacks the translocation but expresses normal ALK, were included as negative controls, as was a blank without RNA (lane 11). (B) Nucleotide sequence (bottom line of text) of the NPM/ALK RNA-PCR product (SEQ ID NO:40). The corresponding amino acid sequence (top line of text)(SEQ ID NO:41) is also shown, and a vertical line indicates the position of the NPM/ALK fusion junction. Single underlines indicate the sequences of the primers (5' primer, direct sequence (SEQ ID NO:5); 3' primer, reverse complement (SEQ ID NO:6)) used for amplification reactions, and the double underline indicates the position of sequences corresponding to the detection oligonucleotide (SEQ ID NO: 10) used as a probe for Southern hybridization. (C) Schematic representations of the proteins encoded by normal NPM, the NPM/ALK fusion gene and normal ALK. Symbols: MB, potential metal-binding domain; AC, acidic amino acid clusters; N, nuclear localization signals; TM, location of the putative transmembrane domain of normal ALK. Arrows indicate the position of the NPM/ALK fusion junction and the corresponding positions in NPM and ALK polypeptides. NPM phosphorylation sites are indicated as follows: solid circles, sites protein kinase C; open circles, sites for nucleolar type II kinase; asterisks, sites for cdc2 kinase. The two protein kinase C phosphorylation sites in the NPM amino-terminus are potential sites only; all other sites have been demonstrated in vitro or in vivo (M. Peter et al., *Cell* 60:791–801 (1990); P.K. Chan et al., *Biochem. J.* 270:549–552 (1990); R. Beckmann et al., *Eur. J. Biochem.* 210:45–51 (1992)).

FIGS. 7A–7E Developmental expression of ALK. (A) In situ hybridization with an antisense ALK probe in a day 12 mouse embryo demonstrating intense signal (bright white grains) in neuronal cells of the trigeminal (V), facial (VII), and acoustic (VIII) ganglia. (B) In situ hybridization with a control ALK sense strand probe in the same region as illustrated in panel A. No background signal is evident. (C) Hybridization of a day 12 embryo using the antisense probe, demonstrating ALK expression in the ventral horns of the spinal cord in the region of the developing motor neurons. (D) Longitudinal section through a day 16 mouse embryo hybridized with the ALK antisense probe. Intense signal along the entire length of the developing spinal cord is evident (anterior cord>>>posterior cord). Note the absence of signal in the lung tissue (top of photo) as well as in the vertebral bodies or peri-vertebral connective tissue. (E) In situ hybridization with the ALK antisense probe on a section of stomach from a day 14 embryo. Clusters of positive cells (arrowhead) between the smooth muscle layers of the gastric wall representing the developing enteric ganglion cells can be seen.

FIGS. 12A–12C NPM/ALK encodes a protein having tyrosine kinase activity. (A) Immune complex kinase assay of anti-ALK immunoprecipitates. Immunoprecipitated proteins were extensively washed, followed by incubation in kinase buffer (25 mM Hepes, 6.5 mM MgCl$_2$ and 12.5 mM MnCl$_2$) containing 20 μCi [γ-$^{32}$P] ATP for 15 min at 30° C. Proteins were resolved by 12.5% SDS-PAGE and exposed to film for 5 min at room temperature. (B) Phosphoamino acid (PAA) analysis. The 72 kDa NPM/ALK protein phosphorylated in vitro (Panel A, SUP-M2) was analyzed. Abbreviations: pS, phosphoserine; pT, phosphothreonine; pY, phosphotyrosine. (C) Antiphosphotyrosine/anti-ALK reciprocal immunoprecipitations and immunoblots of lysates from t(2;5)-negative orpositive lines K562 and SUP-M2, respectively. The positions of NPM/ALK and of two isoforms of tyrosine-phosphorylated SHC (Src homologous and collagen) protein that co-precipitate with NPM/ALK are indicated.

FIGS. 18A–18D Colony formation in soft agar by Fr3T3 that express NPM/ALK. High-power magnification (x 6) of the plates shown in FIG. 17. (A and B) Cells infected with pSRαMSVtkneo/NPM/ALK viral stock. (C) Cells infected with viral stock produced using "empty" pSRαMSVtkneo. (D) Uninfected parental Fr3T3. A single small soft agar colony representative of the low level of spontaneously-arising "background" colonies observed with the Fr3T3 used can be seen in panel D.

DETAILED DESCRIPTION OF THE PREFERRED EMBODIMENTS

Figure 1A:
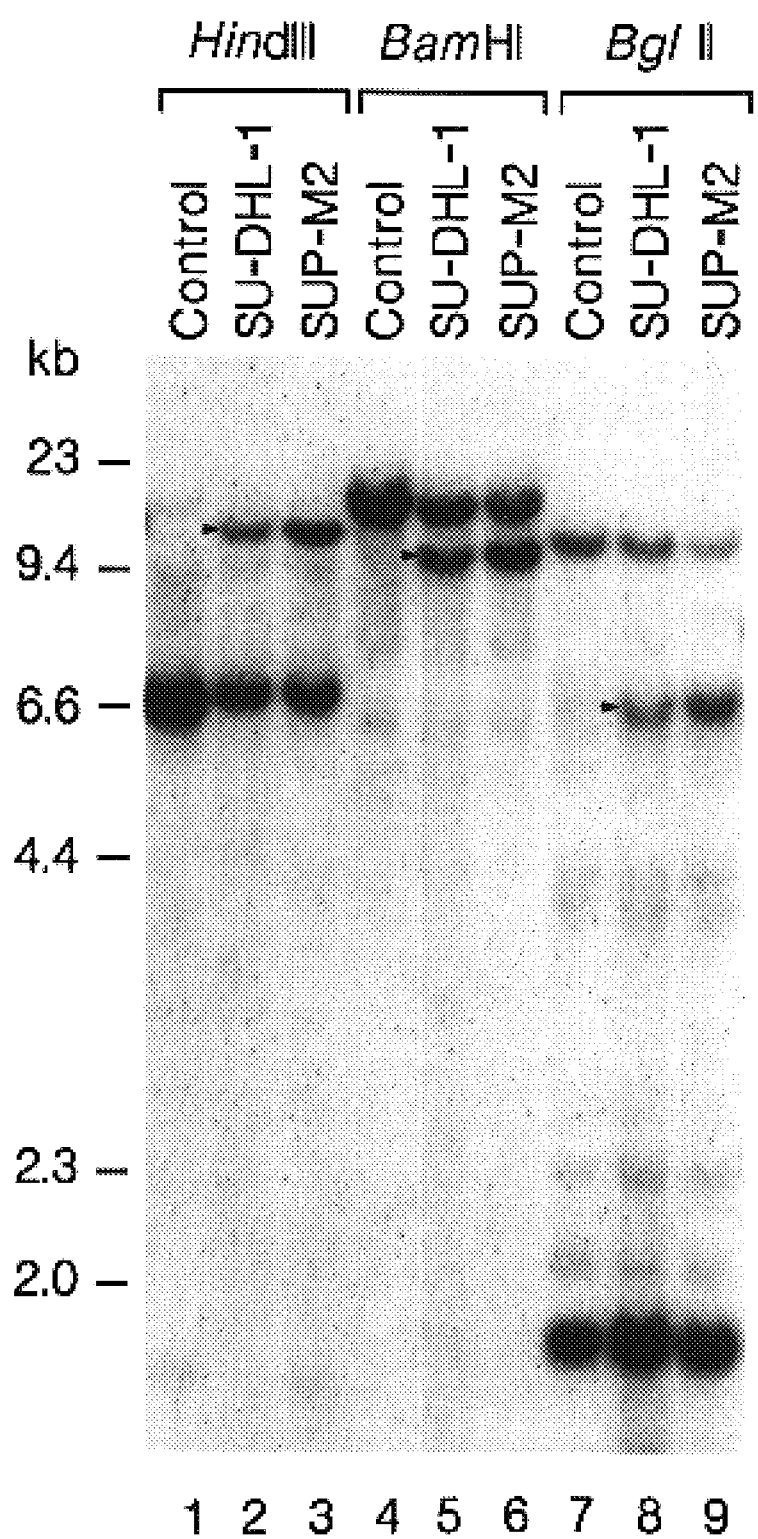
FIGS. 1A–1C (A) Southern blot analysis of DNAs prepared from a karyotypically normal, Epstein-Barr virus-immortalized human lymphocyte cell line (control, lanes 1, 4 and 7) and the t(2; 5)-positive cell lines SU-DHL-1 (lanes 2, 5, and 8) and SUP-M2 (lanes 3, 6, and 9) with the p16–3/1.3S probe. Arrowheads indicate rearranged restriction fragments. (B) Northern blot analysis of RNAs from t(2;5)-negative B-lymphoid (NALM-6, lane 2), T-lymphoid (MOLT4, lane 1; CEM, lane 3) and rhabdomyosarcoma (Rh3O, lane 7) transformed cell lines and the t(2;5)-positive lines SU-DHL-1, SUP-M2 and UCONN-L2 (lanes 4–6) with a 5' NPM cDNA fragment (top panel) and a 3' fragment from the NPM/ALK cDNA (pS1.2) (bottom panel) (The faint, approximately 4 kb bands evident in the t(2;5)-positive cell line RNAs that were hybridized with pS1.2 represent cross-hybridization of this probe with the 28S ribosomal RNA; such bands were not apparent in hybridizations of poly (A)+ RNA). Twenty micrograms of total RNA was loaded in each sample lane, with the exception of Rh30 (8 µg poly (A)+). (C) Analysis of RNAs (2 µg poly (A)+per lane; Clontech, San Diego, Calif.) from various adult and fetal human tissues with a 3' NPM/ALK cDNA probe (pS1.2). Open circles, 6.5 kb ALK transcripts; closed circles, 8.0 kb transcripts; open square, 4.4 kb transcript; arrowheads, 6.0 kb transcripts. Hybridization results obtained with a β-actin cDNA probe are shown in the lower panel. The panels hybridized with pS1.2 represent 6-day autoradiographic exposures; the β-actin hybridizations were exposed for 4 hr.

The present invention is based on the identification and characterization of two nucleic acid sequences: (1) the NPM/ALK fusion gene, which is present as a result of a chromosomal translocation event associated with human t(2;5) lymphoma and (2) a novel gene, ALK, encoding a novel protein tyrosine kinase (the ALK protein) which is located on human chromosome 2p23.

Figure 2C:
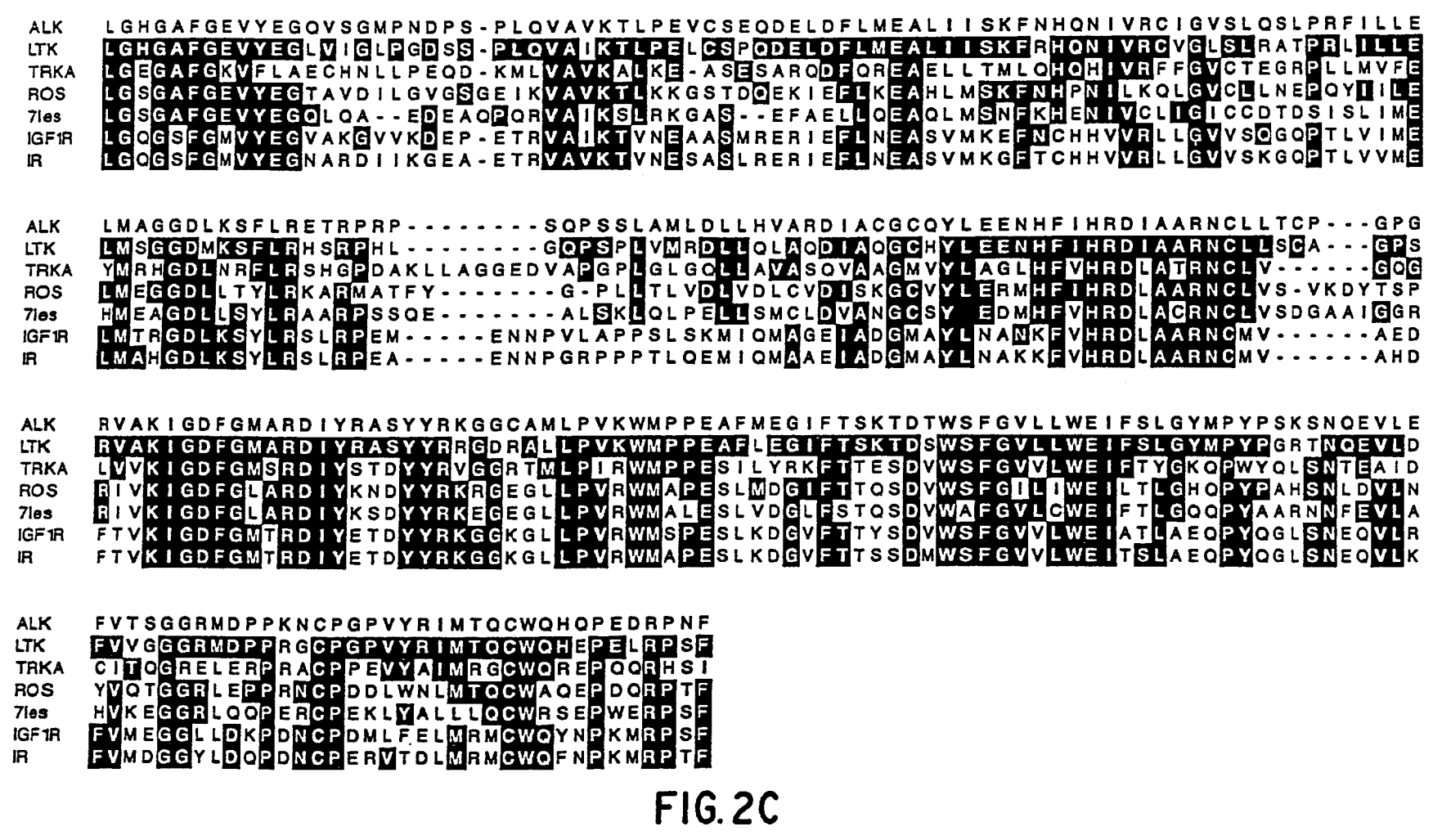

The NPM/ALK fusion gene, present in t(2;5) lymphoma cells, expresses an mRNA containing a fusion of the previously-known nucleolar phosphoprotein gene (NPM) and the novel ALK gene. This mRNA contains an open reading frame that encodes a novel fusion protein product, the NPM/ALK fusion protein. The amino acid sequences of the NPM/ALK fusion protein (SEQ ID NO:4) and of the ALK polypeptide immediately adjacent to the NPM/ALK fusion junction (SEQ ID NO:7) are presented in FIGS. 2(A) and 2(B), respectively.

Based on these observations, one embodiment of the present invention provides a first isolated nucleic acid sequence, ALK (SEQ ID NO:1), which encodes the ALK protein (SEQ ID NO:2) and a second isolated nucleic acid sequence, NPM/ALK (SEQ ID NO:3), which encodes the NPM/ALK fusion protein (SEQ ID NO:4). Clones containing the ALK cDNA and the NPM/ALK cDNA have been deposited under the terms of the Budapest Treaty at the American Type Culture Collection (ATCC) with the accession numbers ATCC 69497 and ATCC 69776, respectively.

By inserting any of the nucleic acid sequences of the present invention into an appropriate vector, one skilled in the art can readily produce large quantities of the specific sequence. Alternatively, the nucleic acid sequences of the present invention can be inserted into an expression vector in order to produce the amino acid sequences of the present invention. There are numerous host/vectors systems available for the propagation of nucleic acid sequences and/or the production of expressed proteins. These include, but are not limited to, plasmid and viral vectors, and prokaryotic and eukaryotic host. One skilled in the art can readily adapt any host/vector system which is capable of propagating or expressing heterologous DNA to produce or express the sequences of the present invention.

Thus, also provided by the present invention are an isolated ALK protein (SEQ ID NO:2) and an isolated NPM/ALK fusion protein (SEQ ID NO:4), which are encoded by their cognate nucleic acids, that is, by SEQ ID NO:1 and SEQ ID NO:3, respectively. Synthetic oligopeptides derived from SEQ ID NO:2 and SEQ ID NO:4 are also provided in this embodiment of the invention.

In Example I(A), the present invention provides evidence that the nucleic acid sequences containing the NPM/ALK fusion sequence are present in patients with t(2;5) lymphoma. Based on this observation, the present invention provides methods of assaying for the presence of nucleic acid sequences containing the NPM/ALK fusion in a sample and thus provides an assay for the detection of t(2;5) lymphoma, as explained in Example I(B).

One example of the assay methods of the present invention which are used to detect NPM/ALK fusions are based on the preferential amplification of sequences within a sample which contain the nucleic acid sequence encoding the NPM/ALK fusion protein. In addition to methods which rely on the amplification of a target sequence, the present invention further provides methods for identifying nucleic acids containing the NPM/ALK fusions which do not require sequence amplification and are based on the known methods of Southern (DNA:DNA) and Northern (DNA:RNA) blot hybridizations, and fluorescence in situ hybridization (FISH) of chromosomal material, using probes derived from the nucleic acid sequences of the invention.

The nucleic acid probes of the present invention include DNA as well as RNA probes, such probes being generated using techniques known in the art (Sambrook et al., eds., *Molecular Cloning,* Cold Spring Harbor Press, Cold Spring Harbor, N.Y. (1989)). A skilled artisan can employ such known techniques using the NPM and ALK nucleotide sequences herein described, or fragments thereof, as probes.

The samples used in the detection methods of the present invention include, but are not limited to, cells or tissues, protein, membrane, or nucleic acid extracts of the cells or tissues, and biological fluids such as blood, serum, and plasma. The sample used in the methods of the invention will vary based on the assay format, nature of the detection method, and the tissues, cells or extracts which are used as the sample. Methods for preparing protein extracts, membrane extracts or nucleic acid extracts of cells are well known in the art and can be readily be adapted in order to obtain a sample which is compatible with the method utilized (see, for example, K. Budelier et al., Chapter 2, "Preparation and Analysis of DNA," M. E. Greenberg et al., Chapter 4, "Preparation and Analysis of RNA" and M. Moos et al., Chapter 10, "Analysis of Proteins," in Ausubel et al., *Current Protocols in Molecular Biology,* Wiley Press, Boston, Mass. (1993)).

One preferred type of sample which can be utilized in the present invention is derived from isolated lymphoma cells. Such cells can be used to prepare a suitable extract or can be used in procedures based on in situ analysis.

The present invention further provides antibodies specific to ALK or NPM/ALK epitopes and methods of detecting ALK proteins, NPM/ALK fusion proteins, or both ALK and NPM/ALK proteins, that rely on the ability of these antibodies to selectively bind to specific portions of ALK or NPM/ALK proteins, as described in detail in Examples I(D) and II(C).

Conditions for incubating an antibody with a test sample vary depending on the format employed for the assay, the detection methods employed, the nature of the test sample, and the type and nature of the antibody used in the assay. One skilled in the art will recognize that any one of the commonly available immunological assay formats (such as radioimmunoassays, enzyme-linked immunosorbent assays, diffusion based ouchterlony, or rocket immunofluorescent assays) can readily be adapted to employ the antibodies of the present invention. Examples of such assays can be found in Chard, T., *An Introduction to Radioimmunoassay and Related Techniques,* Elsevier Science Publishers, Amsterdam, The Netherlands (1986); Bullock, G. R. et al., *Techniques in Immunocytochemistry, Academic Press,* Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

In one embodiment of the immunoassays of the invention, the anti-NPM antibody, the anti-ALK antibody or the anti-NPM/ALK antibody is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling antibodies to such solid supports are well known in the art (see, for example, Weir, D. M. et al., *Handbook of Experimental Immunology,* 4th Ed., Blackwell Scientific Publications, Oxford, England, Chapter 10 (1986)).

Additionally, one or more of the antibodies used in the above described methods can be detectably labeled prior to use. Antibodies can be detectably labeled through the use of radioisotopes, affinity labels (such as biotin, avidin, etc.), enzymatic labels (such as horse radish peroxidase, alkaline phosphatase, etc.) fluorescent labels (such as FITC or rhodamine, etc.), paramagnetic atoms, etc. Procedures for accomplishing such labeling are well-known in the art; see, for example, Sternberger, L. A. et al., *J. Histochem. Cytochem.* 18:315–333 (1970); Bayer, E. A. et al., *Meth. Enzym.* 62:308–315 (1979); Engrall, E. et al., *J. Immunol.* 109:129–135 (1972); Goding, J. W., *J. Immunol. Meth.* 13:215–226 (1976).

The materials used in the above assay methods (both nucleic acid and protein based) are ideally suited for the preparation of a kit. For example, for amplification based detection systems, the invention provides a compartmentalized kit to receive in close confinement, one or more containers which comprises (a) a first container comprising one or more of the amplification primers of the present invention, and (b) one or more other containers comprising one or more of the following: a sample reservoir, amplification reagents, wash reagents, and detection reagents.

For antibody based detection systems, the present invention provides a compartmentalized kit to receive in close confinement, one or more containers which comprises (a) a first container comprising an antibody capable of binding to NPM, (b) a second container comprising an antibody capable of binding to ALK; and (c) one or more other containers comprising one or more of the following: wash reagents and reagents capable of detecting the presence of bound antibodies from the first and the second containers.

The invention further provides a kit compartmentalized to receive in close confinement one or more containers which comprises (a) a first container comprising an antibody capable of binding to an epitope which is present in the fusion junction of the NPM/ALK fusion protein and which is not present in either of the two non-fusion proteins; and (b) one or more other containers comprising one or more of the following: wash reagents and reagents capable of detecting the presence of bound antibodies from the first container.

In detail, a compartmentalized kit includes any kit in which reagents are contained in separate containers. Such containers include small glass containers, plastic containers or strips of plastic or paper. Such containers allow one to efficiently transfer reagents from one compartment to another compartment such that the samples and reagents are not cross-contaminated, and the agents or solutions of each container can be added in a quantitative fashion from one compartment to another. Such containers may include a container which will accept the test sample, a container which contains the antibodies or probes used in the assay, containers which contain wash reagents (such as phosphate buffered saline, Tris-buffers, etc.), and containers which contain the reagents used to detect the bound antibody or the hybridized probe.

For nucleic acid probes, examples of detection reagents include, but are not limited to radiolabeled probes, enzymatic labeled probes (horse radish peroxidase, alkaline phosphatase), and affinity labeled probes (biotin, avidin, or steptavidin). For antibodies, examples of detection reagents include, but are not limited to, labeled secondary antibodies, or in the alternative, if the primary antibody is labeled, the chromophoric, enzymatic, or antibody binding reagents which are capable of reacting with the labeled antibody. One skilled in the art will readily recognize that the antibodies and nucleic acid probes described in the present invention can readily be incorporated into one of the established kit formats which are well known in the art.

The present invention further includes methods for selectively killing cells expressing the NPM/ALK fusion protein by, for example, contacting a cell expressing the NPM/ALK fusion protein with a toxin derivatized antibody, wherein the antibody is capable of binding to the fusion protein but is incapable of binding to non-fusion NPM or ALK protein. Examples of such antibodies are toxin derivatized antibodies which bind to the NPM/ALK fusion junction. As used herein, an antibody is said to be "toxin-derivatized" when the antibody is covalently attached to a toxin moiety. Procedures for coupling such moieties to a molecule are well known in the art. The binding of a toxin derivatized antibody to a cell brings the toxin moiety into close proximity to the cell and thereby promotes cell death. By providing such an antibody molecule to a mammal, the cell expressing the fusion protein can be preferentially killed. Any suitable toxin moiety may be employed; however, it is preferable to employ toxins such as, for example, the ricin toxin, the cholera toxin, the diphtheria toxin, radioisotopic toxins, or membrane-channel-forming toxins.

The antibodies or toxin-derivatized antibodies of the present invention may be administered to a mammal intravenously, intramuscularly, sub-cutaneously, enterally, topically or parenterally. When administering antibodies or peptides by injection, the administration may be by continuous injections, or by single or multiple injections.

The antibodies or toxin-derivatized antibodies of the present invention are intended to be provided to recipient mammal in a "pharmaceutically acceptable form" in an amount sufficient to "therapeutically effective." An amount is said to be therapeutically effective if the dosage, route of administration, etc. of the agent are sufficient to preferentially kill a portion of the cells expressing the NPM/ALK fusion protein. An antibody is said to be in a "pharmacologically acceptable form" if its administration can be tolerated by a recipient patient. The antibodies of the present invention can be formulated according to known methods of preparing pharmaceutically useful compositions, whereby these materials, or their functional derivatives, are combined with a pharmaceutically acceptable carrier vehicle. Suitable vehicles and their formulation, inclusive of other human proteins, e.g., human serum albumin, are described, for example, in *Remington's Pharmaceutical Sciences,* 16th ed., Osol, A., ed., Mack, Easton Pa. (1980). In order to form a pharmaceutically acceptable composition which is suitable for effective administration, such compositions will contain an effective amount of an antibody of the present invention together with a suitable amount of carrier. In addition to carriers, the antibodies of the present invention may be supplied in humanized form. Humanized antibodies may be produced, for example by replacing an immunogenic portion of an antibody with a corresponding, but non-immunogenic portion (i.e., chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al, *Science* 240:1041–1043 (1988); Liu, A. Y. et al., *Proc. Natl. Acad. Sci. USA* 84:3439–3443 (1987); Liu, A. Y. et al., *J. Immunol.* 139:3521–3526 (1987); Sun, L. K. et al., *Proc. Natl. Acad. Sci. USA* 84:214–218 (1987); Nishimura, Y. et al., *Cancer Res.* 47:999–1005 (1987); Wood, C. R. et al., *Nature* 314:446–449 (1985)); Shaw et al., *J. Natl. Cancer Inst.* 80:1553–1559 (1988).

In providing a patient with an antibody or toxin-derivatized antibody, the dosage of administered agent will vary depending upon such factors as the patient's age, weight, height, sex, general medical condition, previous medical history, etc. In general, it is desirable to provide the recipient with a dosage of the antibody which is in the range of from about 1 pg/kg to 10 mg/kg (body weight of patient), although a lower or higher dosage may be administered.

In another embodiment of the present invention, methods are provided for modulating the translation of RNA encoding the NPM/ALK fusion protein in the cell. Specifically, such methods comprise introducing into a cell a DNA sequence which is capable of transcribing RNA which is complimentary to the mRNA encoding the NPM/ALK fusion protein. By introducing such a sequence into a cell, antisense RNA will be produced that will hybridize to NPM/ALK mRNA and block the translation of the NPM/ALK fusion protein. Antisense cloning has been described elsewhere in more detail by Methis et al., *Blood* 82:1395–1401 (1993); Stein et al., *Science* 261:1004–1012 (1993); Mirabella et al., *Anti-Cancer Drug Design* 6:647–661 (1991); Rosenberg et al., *Nature* 313:703–706 (1985); Preiss et al., *Nature* 313:27–32 (1985), Melton, *Proc. Natl. Acad. Sci. USA* 82:144–148 (1985) and Kim et al., *Cell* 42:129–138 (1985). Transcription of the introduced DNA will result in multiple copies of the antisense RNA being generated. By controlling the level of transcription of antisense RNA, and the tissue specificity of expression via promoter selection or gene targeting of the antisense expression sequence, one skilled in the art can regulate the level of translation of the NPM/ALK fusion protein and/or the ALK protein in specific cells within a patient. In a related method, one or more synthetic antisense oligonucleotides that are complementary to the NPM/ALK and/or ALK coding sequences of the invention, optionally including chemical modifications designed to stabilize the oligonucleotide or enhance its uptake into cells, are administered to cells of a patient by known methods (see, for example, R. W. Wagner, *Nature* 372:333–335 (1994); J. Lisziewicz et al., *Proc. Natl. Acad. Sci. (USA)* 90:3860–3864 (1993); S. Fitzpatrick-McElligott, *Bio/Technology* 10: 1036–1040 (1992); E. Uhlmann et al., *Chemical Reviews* 90:543–583 (1990); and B. Tseng et al., *Cancer Gene Therapy* 1:65–71 (1994)).

The level of expression of the NPM/ALK fusion protein can also be controlled through the use of ribozyme technology (for example, see Shore et al., *Oncogene* 8:3183–3188 (1993); Sarver et al., *Science* 247:1222–1225 (1990); and Cech, T., *JAMA* 260:303–3034 (1988)). Using known procedures, ribozymes specific for the NPM/ALK fusion mRNA can be generated and either supplied to or expressed within a cell. The supplying or expression of the ribozyme results in the cleavage of the mRNA encoding the NPM/ALK fusion protein.

In another embodiment of the present invention, methods are provided for identifying agents which are capable of binding to the NPM/ALK fusion protein herein described. Such methods comprise (a) contacting an agent with NPM/ALK fusion protein, or fragment thereof, and (b) determining whether the agent binds to the fusion protein. Using this method, agents which can be used to modulate the activity of the NPM/ALK fusion protein can be identified.

In another embodiment of the present invention, methods are provided for identifying agents which are capable of binding to the ALK fusion herein described, comprising (a) contacting an agent with ALK protein, or a fragment thereof, and (b) determining whether the agent binds to the ALK protein. Using this method, agents which can be used to modulate the activity of the ALK protein, including agonists and antagonists, can be identified. In addition, this method can be used to identify the natural ligand(s) of the ALK protein.

There are numerous variations of the above assays which can be used by a skilled artisan without the need for undue experimentation in order to isolate agonists, antagonists, and ligands of the ALK protein; see, for example, Burch, R. M., in *Medications Development: Drug Discovery, Databases, and Computer-Aided Drug Design,* NIDA Research Monograph 134, NIH Publication No. 93-3638, Rapaka, R. S., and Hawks, R. L., eds., U.S. Dept. of Health and Human Services, Rockville, Md. (1993), pages 37–45. For example, an idiotypic antibody to ALK can be used to co-precipitate ALK-bound agents in the purification and characterization of such agents. Harlow, E., et al., Chapter 11 in *Antibodies: A Laboratory Manual,* Cold Spring Harbor Laboratories, Cold Spring harbor, N.Y. (1988), pages 421–470. Further, an anti-idiotypic antibody to ALK can be used to design synthetic ALK ligands. Ertl, H., et al., *Vaccine* 6:80–84 (1988); Wolff, M. E., in *Medications Development: Drug Discovery, Databases, and Computer-Aided Drug Design,* NIDA Research Monograph 134, NIH Publication No. 93-3638, Rapaka, R. S., and Hawks, R. L., eds., U.S. Dept. of Health and Human Services, Rockville, Md. (1993), pages 46–57. In addition, an anti-idiotypic antibody to ALK, the ALK protein, or an ALK fragment containing the active (ligand binding) site of ALK, can be used to screen an expression library for genes encoding proteins which bind ALK. Alternatively, cells expressing ALK proteins on their surfaces can be used to screen expression libraries or synthetic combinatorial oligopeptide libraries. Cwirla, S. E., et al., *Proc. Natl. Acad. Sci. (USA)* 87:6378–6382 (1990); Houghten, R. A., et al., *Nature* 354:84–86 (1991); Houghten, R. A., et al., in *Medications Development: Drug Discovery, Databases, and Computer-Aided Drug Design,* NIDA Research Monograph 134, NIH Publication No. 93-3638, Rapaka, R. S., and Hawks, R. L., eds., U.S. Dept. of Health and Human Services, Rockville, Md. (1993), pages 66–74. In particular, cells that have been genetically engineered to express and display ALK protein via the use of the ALK nucleic acids of the invention are preferred in such methods, as host cell lines may be chosen which are devoid of related receptors. Hartig, P. R., in *Medications Development: Drug Discovery, Databases, and Computer-Aided Drug Design,* NIDA Research Monograph 134, NIH Publication No. 93-3638, Rapaka, R. S., and Hawks, R. L., eds., U.S. Dept. of Health and Human Services, Rockville, Md. (1993), pages 58–65.

The agents screened in the above assay can be, but are not limited to, peptides, carbohydrates, or vitamin derivatives. The agents can be selected and screened at random or rationally selected or designed using protein modeling techniques. For random screening, agents such as peptides or carbohydrates are selected at random and are assayed for their ability to bind to the pseudogene peptide. Alternatively, agents may be rationally selected or designed. As used herein, an agent is said to be "rationally selected or designed" when the agent is chosen based on the configuration of the pseudogene peptide. For example, one skilled in the art can readily adapt currently available procedures to generate peptides capable of binding to a specific peptide sequence in order to generate rationally designed antipeptide peptides, see, for example, Hurby et al., "Application of Synthetic Peptides: Antisense Peptides," in *Synthetic Peptides: A User's Guide, W. H. Freeman, New York* (1992), pp. 289–307; and Kaspczak et al., *Biochemistry* 28:9230–2938 (1989).

Using the above procedures, the present invention provides agents capable of binding to the NPM/ALK fusion protein, produced by a method comprising the steps of (a) contacting said agent with NPM/ALK fusion protein, or a fragment thereof, and (b) determining whether said agent binds to said NPM/ALK fusion protein.

Using the above procedures, the present invention provides agents capable of binding to the ALK protein, produced by the steps of (a) contacting said agent with the ALK protein, or a fragment thereof, and (b) determining whether said agent binds to said ALK protein.

The present invention further provides methods of generating transgenic animals which contain the NPM/ALK gene fusion and/or the ALK gene. Such animals are useful as animal models for human t(2;5) lymphoma and for studying ALK function and activity. In general, methods of generating transgenic animals are well known in the art (for example, see Grosveld et al., *Transgenic Animals,* Academic Press Ltd., San Diego, Calif. (1992)). Using the sequences disclosed herein for the NPM/ALK fusion or the ALK protein, a skilled artisan can readily generate a transgenic animal which contains and expresses the NPM/ALK fusion protein and/or the ALK protein. Transgenic animals (such as mice and pigs) which express the NPM/ALK fusion can be used as an animal model for human t(2;5) lymphoma. Transgenic animals which express the ALK protein are useful for studying ALK function and activity. Such animals serve as models for the development of alternative therapies for t(2;5) lymphoma.

In addition to transgenic non-human mammals which have been altered to contain the human ALK gene or the NPM/ALK fusion gene, the present invention further provides non-human transgenic mammals which have been altered to "knock-out" the expression of the normal non-human mammalian homologue of the ALK gene. Specifically using procedures of gene targeting described elsewhere, a skilled artisan can employ the ALK gene of the present invention to inactivate (knock out) a homologous gene in a non-human mammal (Mansour et al., *Nature* 336:348–352 (1988)). The "knock out" procedure has been successfully employed in a number of mammalian systems (see, for example, Lui et al., *Cell* 75:59–72 (1993)). Because of the high degree of conservation of the ALK gene, the human ALK sequence can be employed to isolate the non-human ALK nucleic acid sequences required for standard knock out procedures.

Other features and advantages of the invention will be apparent from the Examples and from the claims. Without further elaboration, it is believed that one skilled in the art can, using the preceding description, utilize the present invention to its fullest extent. The entire text of all publications cited herein is hereby incorporated by reference.

EXAMPLE 1

NPM/ALK Fusion Gene and Protein

A. Molecular Structure of the t(2;5) Translocation

In order to clone the genes altered by the t(2; 5), a positional strategy based on fluorescence in situ hybridization (FISH) ordering of regionally derived cosmid clones was used. In contrast to the majority of leukemia- and lymphoma-associated chromosomal translocations that have been molecularly characterized, the t(2;5) does not involve immunoglobulin or T-cell receptor genes, nor other cloned genes that have been previously localized to the breakpoint regions. Thus, to identify the breakpoint on chromosome 5, microdissection clones from bands 5q34-q35 were isolated and used to identify 39 cosmid clones (Saltman, D., et al., *Nucleic Acids Res.* 20:1401–1404 (1992)), which then were oriented relative to the breakpoint by FISH analysis of metaphase chromosomes from the SUP-M2 and SU-DHL-1 t(2;5)-positive cell lines (Morgan, R., et al., *Blood* 73:2155–2164 (1989)). Seventeen clones mapped centromeric and 22 clones telomeric to the breakpoint; clones from these groups were oriented relative to one another by two-color metaphase FISH analysis. FISH was performed as previously described (Morris, S., et al., *Blood* 78:2013–2020 (1991); Saltman, D., et al., *Genomics* 16:726–732 (1993)).

The genomic distance between the two cosmids that flanked the breakpoint most closely, designated cos47C12 (centromeric) and cos191E7 (telomeric), was 290 kb as estimated by interphase FISH analysis (Lawrence, J., et al., *Science* 249:928–932 (1990); Trask, B., et al., *Am. J. Hum. Genet.* 48:1–15 (1991)) in cells containing a normal chromosome 5. However, despite their proximity to the chromosome 5 breakpoint, probes prepared from these cosmids did not detect rearranged restriction fragments by Southern blot analysis of pulsed-field gels prepared from DNA of t(2;5)-containing cell lines.

Bidirectional chromosome walks were performed from cosmids, approximately 290 kb apart, that flanked the breakpoint on chromosome 5; each walk spanned a genomic region of 150 kb. Using as a genomic probe the isolated 70 kb from the telomeric cosmid, rearranged restriction fragments in DNAs of two cell lines containing the t(2;5) were detected (FIG. 1(A)). Approximately 70 kb toward the breakpoint from the telomeric flanking clone, chromosome 5-specific genomic probes (p16-3/1.2S and p21-3/3E) were isolated that identified rearranged fragments with multiple enzymes in Southern blot analysis of DNAs from t(2;5)-positive cell lines. The genomic fragment p16-3/1.2S is located immediately centromeric to the chromosome 5 breakpoint, whereas p21 -3/3E lies just telomeric to the break. Both probes identified a 1.6 kb transcript in Northern analysis of RNAs prepared from t(2;5)-positive and negative cell lines; in addition, p16-3/1.2S hybridized to a 2.4 kb transcript found only in t(2;5)-positive RNAs.

One of the probes (p21-3/3E) was hybridized to a cDNA library prepared from the polyadenylated RNA of the UOC-B 1 pro-B leukemia cell line, which lacks the t(2;5) translocation. Multiple cDNA clones were isolated that hybridized to a ubiquitously expressed 1.6 kb mRNA, which was predicted by sequence analysis to encode nucleophosmin (NPM; also known as B23 or numatrin), a highly conserved nucleolar phosphoprotein that shuttles ribosomal components between the nucleolus and the cytoplasm in the later stages of ribosome assembly (Chan, W. Y., et al., *Biochemistry* 28:1033–1039 (1989); Borer, R. A., et al., *Cell* 56:379–390(1989)). Probing of RNAs prepared from cell lines with or without the t(2;5), using a subclone from the 5' end of the NPM cDNA, identified both the normal NPM transcript and a 2.4 kb transcript restricted to t(2;5)-positive cell lines (FIG. 1(B), top). In contrast, a subclone containing 3' untranslated sequences detected only the normal 1.6 kb NPM transcript.

By screening a cDNA library prepared from the mRNA of the SU-DHL-1 t(2;5)-containing cell line, more than 20 clones that hybridized to 5' but not 3' NPM probes were isolated. Sequences from the 5' ends of the three longest clones were identical to 5' NPM cDNA sequences but diverged after the codon for Val-117. NPM sequences 3' of this codon were replaced by the 3' 1,689 nucleotides of an open reading frame derived from chromosome 2 (subsequently designated ALK), resulting in a fused open reading frame (subsequently designated NPM/ALK) composed of a total of 2,040 nucleotides encoding a polypeptide composed of 680 amino acid residues (FIG. 2(A); SEQ ID NOS:3 and 4).

Figure 1B:
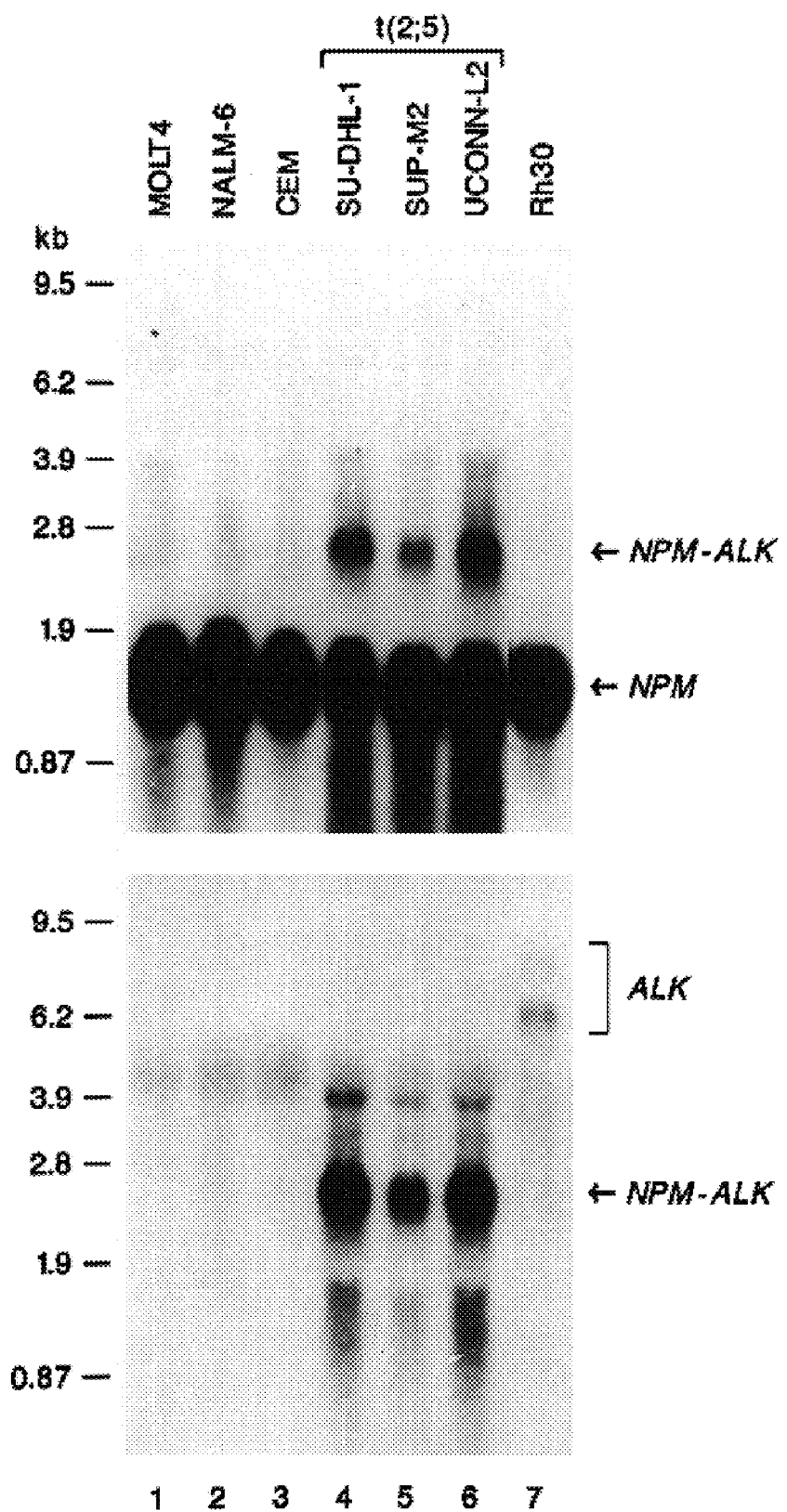
Figure 3A:
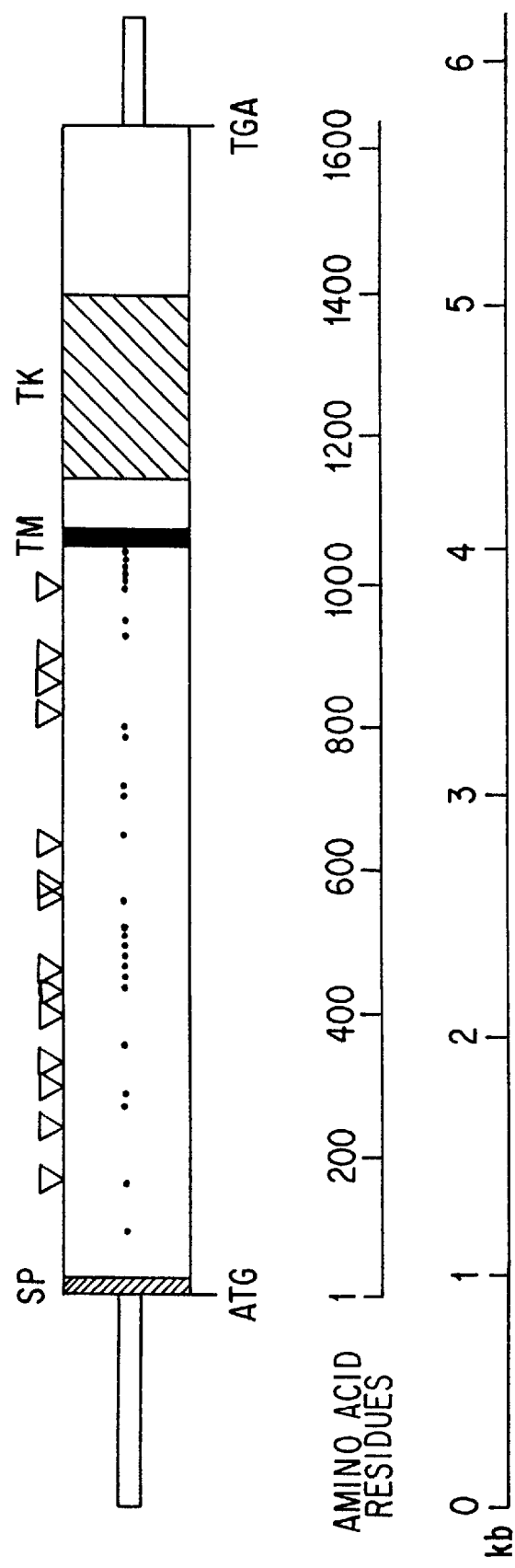

A probe prepared from the 3' end of the fusion cDNA (pS1.2) identified the same 2.4 kb transcript that had been detected with the 5' NPM probe in RNAs from t(2;5)-positive cells (FIG. 1(B), bottom). This fragment was localized to band p23 of chromosome 2 by hybridization to DNAs of human x rodent somatic cell hybrids and by metaphase FISH analysis, indicating that the 2.4 kb mRNA is encoded by a fused gene created by the t(2;5). The 3' portion of the chimeric t(2;5) cDNA encodes conserved residues characteristic of the catalytic domain of members of the protein-tyrosine kinase (PTK) gene family (Hanks, S. K., et al., *Science* 241:42–52 (1988); Taylor, S. S., et al., *Annu. Rev. Cell Biol.* 8:429–462 (1992)). (FIG. 2(C)). This newly identified PTK gene (SEQ ID NO:1), encoding the polypeptide sequence shown in FIG. 3(B) (SEQ ID NO:2) and diagramed in FIG. 3(A) is named ALK (Anaplastic Lymphoma Kinase).

Figure 1C:
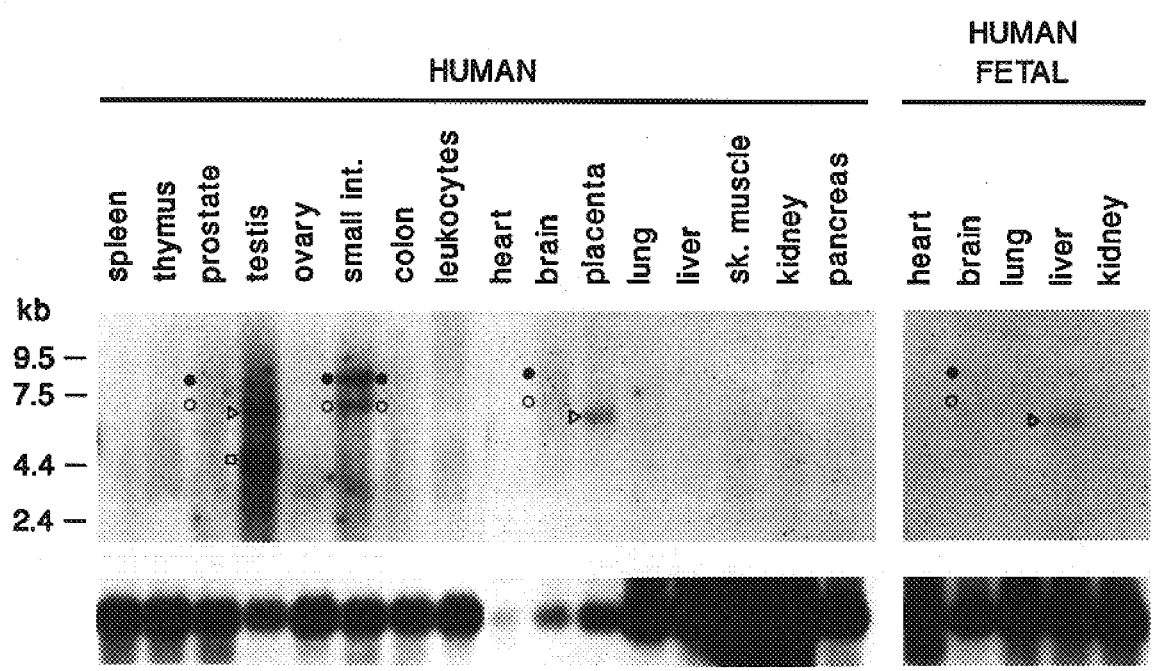

When a 3' NPM-ALK cDNA (pS1.2) is used as a probe in Northern blot analysis of mRNAs from specific normal human tissues (small intestine, fetal and adult brain, colon, prostate, testis, placenta, and fetal liver), four different ALK transcripts of 4.4, 6.0, 6.5, and 8.0 kb are observed (FIG. 1(C)). All four mRNAs are also detected with a probe containing only 3' untranslated ALK sequences, demonstrating that they represent differentially spliced ALK mRNAs.

FISH mapping indicated that NPM and ALK are transcribed in centromeric to telomeric orientations on chromosomes 5 and 2, respectively, with the 2.4 kb fusion transcript arising from the derivative 5 translocated chromosome. Northern blot analysis provided no evidence for expression of a reciprocal ALK/NPM chimeric transcript, which could have been generated from the derivative 2 chromosome.

The Oncogenic Role of the NPM/ALK Fusion

The frequency of the t(2;5) in anaplastic large cell lymphomas indicates that the NPM/ALK product has a major role in the pathogenesis of these neoplasms. The normal NPM protein is a nonribosomal nucleolar phosphoprotein involved in the assembly of preribosomal particles into both small and large ribosomal subunits (W. Y. Chan et al., *Biochemistry* 28:1033–1039 (1989); R. A. Borer et al., *Cell* 56:379–390 (1989); M. S. Schmidt-Zachmann et al., *EMBO J.* 6:1881–1890 (1987); M. S. Schmidt-Zachmann et al., *Chromosoma.* 96:417–426 (1988); D. Hemandez-Verdun, *J. Cell. Sci.* 99:465–471 (1991)). It binds cooperatively with high affinity to single-stranded nucleic acids, exhibits RNA helix-destabilizing activity, and is found in association with the most mature nucleolar preribosomal ribonucleoproteins (T. S. Dumbar et al., *Biochemistry* 28:9495–9501 (1989)). The relative abundance of NPM transcripts and protein is cell cycle regulated. NPM transcription and translation peak just prior to the entry of cells into S phase, with a decline to baseline just before the onset of G2 phase (N. Feuerstein et al., *J. Immunol.* 139:1818–1822 (1987); N. Feuerstein et al., *J. Biol. Chem.* 262:11389–11397 (1987); N. Feuerstein et al., *J. Biol. Chem.* 263:10608–10612(1988); N. Feuerstein et al., *J. Cell Biol.* 107:1629–1642 (1988); N. Feuerstein et al., *Exp. Cell Res.* 194:289–296 (1991)).

Sequences encoding most of the known structural domains of NPM are not incorporated into the fusion transcript (W. Y. Chan et al., *Biochemistry* 28:1033–1039 (1989); R. A. Borer et al., *Cell* 56:379–390 (1989); M. Peter et al., *Cell* 60:791–801 (1990); P. K. Chan et al., *Biochem. J.* 270:549–552 (1990); R. Beckmann et al., *Eur. J. Biochem.* 210:45–51 (1992)) (FIG. 5(C)). One possibility is that the NPM gene contributes an active promoter to drive expression of the ALK catalytic domain in lymphoma cells containing the t(2;5). This role for NPM would appear to be crucial, because the ALK promoter is normally silent in lymphoid cells. An oncogenic role, if any, for the amino-terminal NPM coding sequences incorporated into NPM/ALK, including those encoding potential protein kinase C phosphorylation sites (Ser-43 and Thr-78) and a potential C-$X_5$-H-$X_4$-H metal binding motif (residues 104–115), remains to be established.

The contribution of aberrantly activated receptor tyrosine kinases to malignant transformation is well recognized (J. Schlessinger et al., *Neuron* 9:383–391 (1992); T. Pawson, *Curr. Opin. Genet. Dev.* 2:4–12 (1992)). For example, malignant activation of TRKA can occur through gene fusions similar to NPM/ALK, in which the enzyme's extracellular domain is replaced by amino acids encoded by other genes, including those for nonmuscle tropomyosin and the ribosomal protein L7a (D. Martin-Zanca et al., *Nature* 319:743–748 (1986); F. Coulier et al., *Mol. Cell. Biol.* 9:15–23 (1989); R. Oskam et al., *Proc. Natl. Acad. Sci. USA* 85:2964–2968 (1988); S. C. Kozma et al., *EMBO J.* 7:147–154 (1988); A. Ziemiecki et al., *EMBO J.* 9:191–196 (1990)). A consistent feature of oncogenic TRKA fusion proteins as well as other tyrosine kinase oncogenes, including BCR-ABL, EGFR, HER2/NEU and CSF-1R, is that much of their potency can be attributed to mutations or gene fusions that lead to a constitutively active catalytic domain (J. Schlessinger et al., *Neuron* 9:383–391 (1992); T. Pawson, *Curr. Opin. Genet. Dev.* 2:4–12 (1992); D. Martin-Zanca et al., *Nature* 319:743–748 (1986); F. Coulier et al., *Mol. Cell. Biol.* 9:15–23 (1989); R. Oskam et al., *Proc. Natl. Acad. Sci. USA* 85:2964–2968 (1988); S. C. Kozma et al, *EMBO J.* 7:147–154 (1988); A. Ziemiecki, et al., *EMBO J.* 9:191–196 (1990)). Thus, in NPM/ALK fusion proteins, one would predict that the truncated ALK kinase is deregulated and phosphorylates intracellular substrates to trigger malignant transformation. Because anaplastic large cell lymphomas arise from activated T lymphocytes, which depend on IL-2 for growth and viability (K. A. Smith, *Science* 240:1169–1176 (1988)), NPM/ALK may phosphorylate substrates that are normally phosphorylated in response to IL-2 receptor-mediated signals (E. M. Saltzman et al., *J. Biol. Chem.* 263:6956–6959 (1988); D. K. Ferris et al., *J. Immunol.* 143:870–876 (1989); I. D. Horak et al., *Proc. Natl. Acad. USA* 88:1996–2000 (1991); M. Hatakeyama et al., *Science* 252:1523–1528 (1991); N. Kobayashi et al., *Proc. Natl. Acad. Sci USA* 90:4201–4205 (1993)), leading to constitutive activation of this signal transduction pathway.

These findings stand in marked contrast to previous molecular genetic studies of T-cell lymphomas and leukemias arising in cells with an immature (thymic) immunophenotype. Chromosomal translocations in lymphoblastic T-cell malignancies consistently affect enhancers included in the TCR β-chain locus on chromosome 7, band q34, or the α/δ locus on chromosome 14, band q11 (M. L. Cleary, *Cell* 66:619–622 (1991); T. H. Rabbitts, *Cell* 67:641–644 (1991)). In each case, these enhancers, which are highly active in T-cell progenitors, cause dysregulated expression of developmentally regulated transcription factor genes (e.g., TAL/SCL, LYL1, RHOMB/TTG and HOX11) located at breakpoints on the reciprocal chromosomes. The observations in large cell lymphoma described herein suggest that the pathways leading to malignant transformation in mature T lymphocytes differ from those responsible for the differentiation arrest and altered growth of thymic progenitors.

B. Detection of NPM/ALK Nucleic Acid Sequences and Expression of the NPM/ALK Gene In Vivo Hybridization Assays The methods of Southern and Northern blot hybridization (Sambrook et al., eds., *Molecular Cloning,* Cold Spring Harbor Press, Cold Spring Harbor, N.Y. (1989)) are employed using probes derived from the nucleic acid sequences of the invention to determine, for example, if a sample contains the NPM/ALK nucleic acid fusion sequence.

For example, one such method comprises the steps of (a) contacting a sample with two nucleic acid probes, wherein the first nucleic acid probe is capable of hybridizing to the nucleic acid sequence encoding NPM, and the second nucleic acid probe is capable of hybridizing to the nucleic acid sequence encoding ALK, and (b) detecting the presence of a nucleic acid sequence in the sample which hybridizes to both the first and the second nucleic acid probes.

Alternatively, a single nucleic acid probe which spans the NPM/ALK fusion junction is used in place of the two separate probes in step (a) of the above method in order to detect nucleic acids having NPM/ALK fusion sequences. Specifically, such a method comprises the steps of (a) contacting a sample with a single nucleic acid probe, wherein the nucleic acid probe is capable of hybridizing to the fusion junction of the NPM/ALK fusion gene, and (b) detecting the presence of nucleic acid sequences in the sample which hybridize to the nucleic acid probe.

Alternatively, a single probe can be designed which is based on either the ALK, NPM or NPM/ALK fusion sequence. Such a probe will correspond to a restriction enzyme fragment of NPM or ALK whose size is altered as a result of the rearrangement (restriction fragment length polymorphism, RFLP analysis).

A probe or probes capable of hybridizing to a portion of the nucleic acid sequence encoding ALK which is not found in the NPM/ALK fusion are used in step (a) of the above methods to specifically detect nucleic acids having ALK sequences. In order to determine the ratio of ALK and NPM/ALK sequences in a sample, a probe or probes capable of hybridizing to a portion of the nucleic acid sequence encoding ALK which is found in the NPM/ALK fusion are used in step (a) of the above methods.

Any method known in the art can be utilized to label the probes used in the above assay methods. In the two probe embodiment, the first and the second probe can be labeled with different radioisotopes, enzymes or chromophores.

Using the differently labeled probes, one can identify DNA sequences which bind one or both of the probes. In another application, the first and the second probe can be labeled in such a fashion that a signal is produced when the probes hybridize to the same nucleic acid fragment. One example of such a procedure is provided in U.S. Pat. No. 4,820,630.

In one application of the above described methods, one of the nucleic acid probes is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

Detection of NPM/ALK Sequences by FISH

Figure 4A:
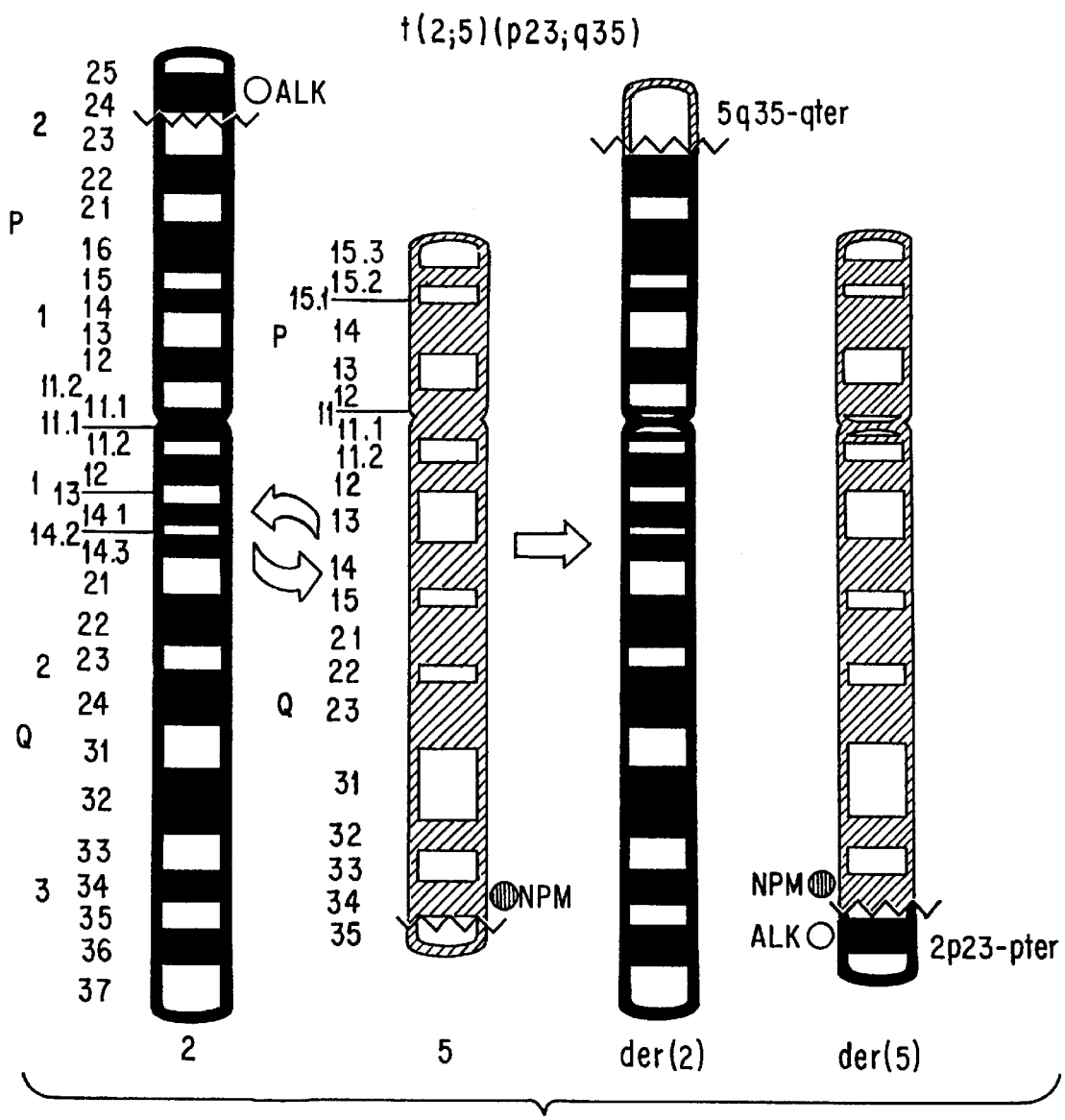
FIGS. 4A–4B Schematic representation of two-color NPM/ALK FISH assay. (A) The locations of the NPM and ALK FISH probes on normal metaphase chromosomes 2 and 5, respectively (left), and their location on the derivative chromosome 5 produced by t(2;5) (right) are shown. (B) The random distribution of NPM and ALK hybridization signals in normal interphase nuclei is shown diagramatically (left); in contrast, specific pairing of NPM and ALK signals is observed in nuclei of t(2;5)-positive lymphoma cells (right).
Figure 4B:
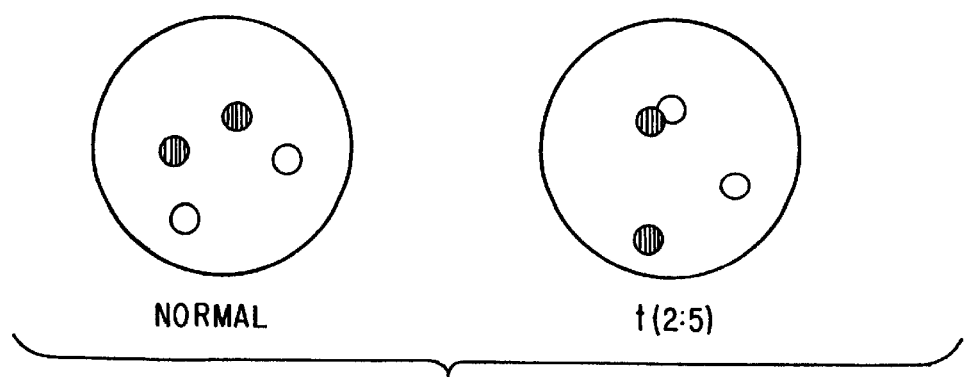

A scheme for detecting NPM/ALK fusions by fluorescence in situ hybridization (FISH) method is shown in FIG. 4. Purified DNAs from chromosome 5 cosmid clones 13, 15-2, and 47 C12, which are located immediately centromeric to the NPM gene locus, were labeled with digoxigenin-11-UTP (Boehringer Mannheim, Indianapolis, Ind.) and the ALK P1 clone 2638 was labeled with biotin-dUTP (Bethesda Research Laboratories, Gaithersburg, Md.) by nick translation. Labeled probes were combined with sheared human DNA and hybridized as differently labeled pairs to fixed interphase nuclei derived from anaplastic large cell lymphomas in a solution containing 50% formamide, 10% dextran sulfate, and 2× SSC. Specific probe signals were detected by incubating the hybridized slides in fluorescein-conjugated sheep antidigoxigenin antibodies (Boehringer Mannheim, Indianapolis, Ind.) and Texas red avidin (Vector Laboratories, Burlingame, Calif.). The slides were then counterstained with 4,6-diamidino-2-phenylindole (DAPI) and analyzed with a triple band pass filter set (Chroma Technologies, Brattleboro, Vt.). The presence of translocation t(2;5) was determined by observing consistently paired red and green signals in the interphase nuclei of t(2;5)-positive lymphoma cells.

Detection of NPM/ALK fusions by FISH allows for the identification of non-consensus fusion junctions, i.e., those not having the nucleotide sequence of SEQ ID NO:3. Thus, FISH detection will reveal all typical NPM/ALK fusions, as well as the occasional variant NPM/ALK fusions that have been identified (Downing, J. R., et al., *Blood* 85:3416–3422 (1995)), some of which are not detectable by the RNA-PCR methods described herein.

PCR Assays

In general, an amplification reaction such as the polymerase chain reaction (PCR) is used to amplify either the mRNA encoding the NPM/ALK fusion protein, or the genomic DNA which contains the t(2;5) translocation.

Specifically, utilizing the sequences of the identified fusion gene, the present invention provides methods of identifying the presence of a nucleic acid sequence in a sample which contains the NPM/ALK fusion sequence comprising the steps of (a) contacting a sample with two nucleic acid amplification primers, wherein a first nucleic acid amplification primer is capable of hybridizing to the nucleic acid sequence encoding NPM or a complementary sequence thereof, and a second nucleic acid amplification primer which is capable of hybridizing to the nucleic acid sequence encoding ALK or a complementary sequence thereof, (b) amplifying the primed nucleic acid sequences in the sample, and (c) detecting the presence of amplified nucleic acid sequence in the sample which contains the NPM/ALK fusion sequence.

As used herein, an amplification primer is any short DNA sequence which can hybridize to a target sequence and allow the target sequence to be amplified when incubated with the appropriate reagents under the appropriate condition. (See, for example, P. Liang et al., Chapter 15, "The Polymerase Chain Reaction," in Ausubel et al., *Current Protocols in Molecular Biology*, Wiley Press, Boston, Mass. (1993), pp. 15.0.1–15.8.8). Amplification requires the use of two primers which flank the region which is to be amplified. One primer hybridizes to the target sequence while the other primer hybridizes to a sequence complementary to the target sequence. In order to achieve specific priming for amplification reactions, it is generally necessary that amplification primers be from about 18 to about 30 nucleotides in length (M. A. Innis et al., "Optimization of PCRs," Chapter 1, and R.K. Saiki., "Amplification of Genomic DNA," Chapter 2, in *PCR Protocols: A Guide to Methods and Applications*, M. A. Innis et al., eds., Academic Press, San Diego, Calif. (1990), pp. 3–20); Privitera et al., *Blood* 79:1781–1788 (1992)).

In the present invention, one of the amplification primers is derived from the sequence of NPM gene while the second primer is derived from the sequence of the ALK gene. Any fragment of the NPM or ALK gene sequences can be used to generate the appropriate amplification primers so long as the fragments of the sequence which are chosen are present in the NPM/ALK fusion gene. A skilled artisan can readily employ techniques known in the art to prepare fragments of the NPM and ALK genes that can be used as primers in PCR reactions.

The target sequence which is to be amplified can either be the mRNA which encodes the NPM/ALK fusion protein or can be genomic DNA which contains the t(2;5) translocation. A skilled artisan can readily employ techniques known in the art to prepare a sample containing the appropriate target molecule.

As used herein, amplification refers to the process of generating multiple copies of a target sequence. Various methods and enzymes are available to accomplish this goal. In the preferred embodiment, Taq-1 DNA polymerase is used in the method known as PCR to amplify the target sequence. However, a skilled artisan can substitute other enzymes for the Taq-1 polymerase so long as the amplification goal is achieved. In general the preferred conditions are characterized as being high stringency conditions. A skilled artisan can readily determine the appropriate conditions (M. A. Innis et al., eds., *PCR Protocols: A Guide to Methods and Applications*, Academic Press, San Diego, Calif. (1990); H. A. Erlich, ed., *PCR Technology: Principles and Applications for DNA Amplification*, Stockton Press, New York, N.Y. (1989)).

As used herein, detecting the amplified target sequence refers to any method which can be employed to determine the presence or absence of an amplified nucleic acid sequence of a given size or a particular sequence. In one application, the amplification product is subjected to agarose or acrylamide gel electrophoresis to resolve the various sizes of nucleic acids which are present in the amplified sample. The resulting gel can then be analyzed visually using a nucleic acid stain, for example ethidium bromide, to determine if an appropriately sized nucleic acid molecule is present in the amplified sample. Alternatively, a detectably labeled probe can be employed to determine if the sample contains the amplified sequence. Such a probe can be used following the above described electrophoresis, or can be used in a dot blot or in situ assay method.

Utilizing the sequences of the NPM/ALK fusion gene, the present invention provides methods of identifying the presence of nucleic acids having the NPM/ALK fusion sequence in a sample which comprises the steps of (a) contacting a sample with two nucleic acid amplification primers, wherein the first nucleic acid amplification primer is capable of hybridizing to the nucleic acid sequence encoding NPM or a reverse complementary sequence thereof, and the second nucleic acid primer is capable of hybridizing to a nucleic acid sequence encoding a portion of ALK present in NPM/ALK or a reverse complementary sequence thereof, (b) amplifying the nucleic acid sequences in the sample which hybridize to the two primers, and (c) detecting the presence of amplified nucleic acid sequences which contain the NPM/ALK fusion.

In a related assay, a third nucleic acid amplification primer is additionally introduced into step (a) of the above method, wherein the third nucleic acid amplification primer is capable of hybridizing to a portion of ALK which is not present in NPM/ALK, or a reverse complementary sequence thereof. In this assay, both ALK and NPM/ALK sequences are amplified and detected and, if desired, the relative concentrations of ALK and NPM/ALK sequences in the sample may be compared.

Alternatively, in order to detect ALK sequences but not NPM/ALK sequences in a sample, two nonidentical nucleic acid amplification primers are used in the above method, wherein the nucleic acid amplification primers are capable of hybridizing to the nucleic acid sequence encoding a portion of ALK not present in NPM/ALK or a reverse complementary sequence thereof.

Detection of NPM/ALK Sequences by RNA-PCR

Figure 5A:
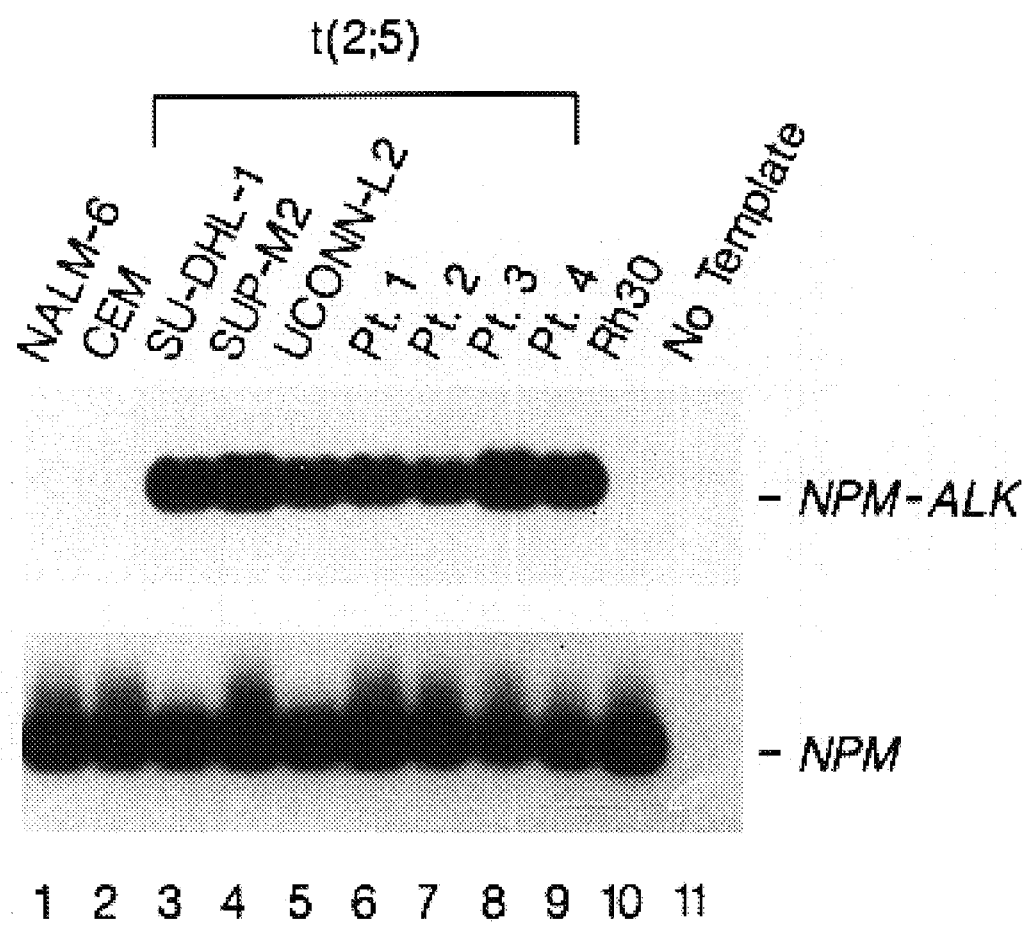
Figure 5C:
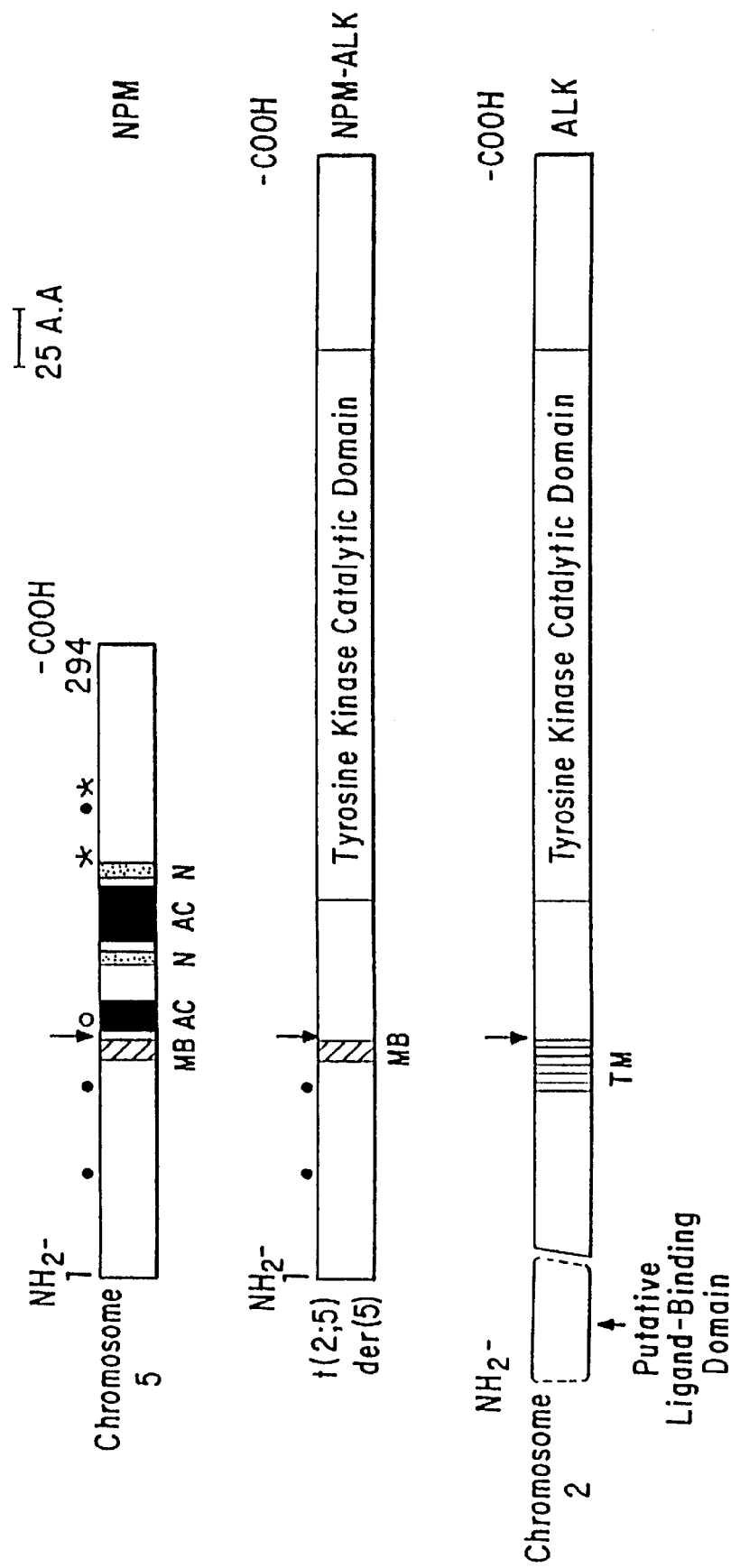

An RNA-based polymerase chain reaction (RNA-PCR) method confirmed the specificity of the fusion junctions in chimeric transcripts expressed in lymphomas harboring the t(2;5) (FIGS. 5(A) and 5(B)). RNA-PCR was performed as previously described (Privitera, E., et al., *Blood* 79:1781–1788 (1992)). Reactions were performed simultaneously with oligonucleotide primers specific for the chimeric NPM/ALK transcript (see FIG. 5(B)) and with a primer pair derived from the ubiquitously expressed NPM gene as a control for reverse transcription and amplification. A 3' NPM primer,

5'-GCTACCACCTCCAGGGGCAGA-3', SEQ ID NO:8, was used with the 5' NPM primer,

5'-TCCCTTGGGGGCTTTGAAATAACACC-3', SEQ ID NO:5, shown in FIG. 5(B) for the control amplifications. The resulting 185 bp NPM product was detected by hybridization with an end-labeled oligonucleotide homologous to normal NPM sequences from the region of the fusion junction,

5'-AGCACTTAGTAGCTGTGGAGGAAG-3', SEQ ID NO:9.

NPM/ALK fusion RNA-PCR products generated from amplifications using oligonucleotide primers corresponding to SEQ ID NO:5 and the reverse complement of SEQ ID NO:6 were detected with an end-labeled oligonucleotide that spans the fusion junction,

5'-AGCACTTAGTAGTGTACCGCCGGA-3', SEQ ID NO:10, shown in FIG. 5(B). Stringent post-hybridization washes were performed at 62° C. in 2×SSC/0.1% SDS for both the NPM/ALK and the NPM detection oligonucleotides.

Conversely, fusion transcripts were not detected in cell lines lacking the t(2;5), including several rhabdomyosarcoma lines that expressed ALK transcripts. NPM/ALK junction sequences were found in the RNAs of all seven t(2;5)-positive samples, including the SU-DHL-1, SUP-M2 and UCONN-L2 cell lines and diagnostic samples from four patients with anaplastic large cell lymphomas, wherein the patient samples (three lymph node biopsies, one pleural effusion) were each shown by cytogenetic analysis to contain lymphoma cells bearing the t(2;5). The sequence of the RNA-PCR products from cells of patients 2 and 4 was determined and found to be identical to the cDNA sequence obtained from the SU-DHL-1 cell line (FIG. 5(B)).

The breakpoints of the 2;5 translocation therefore appear to consistently involve the same introns of the NPM and ALK genes, leading to identical junctions in spliced mRNAs arising from the fused gene. Because of the difficulties in cytogenetic analysis of lymphoma biopsy samples, molecular detection of NPM/ALK fusion mRNAs by RNA-PCR should markedly improve the identification of these tumors.

Figure 6:
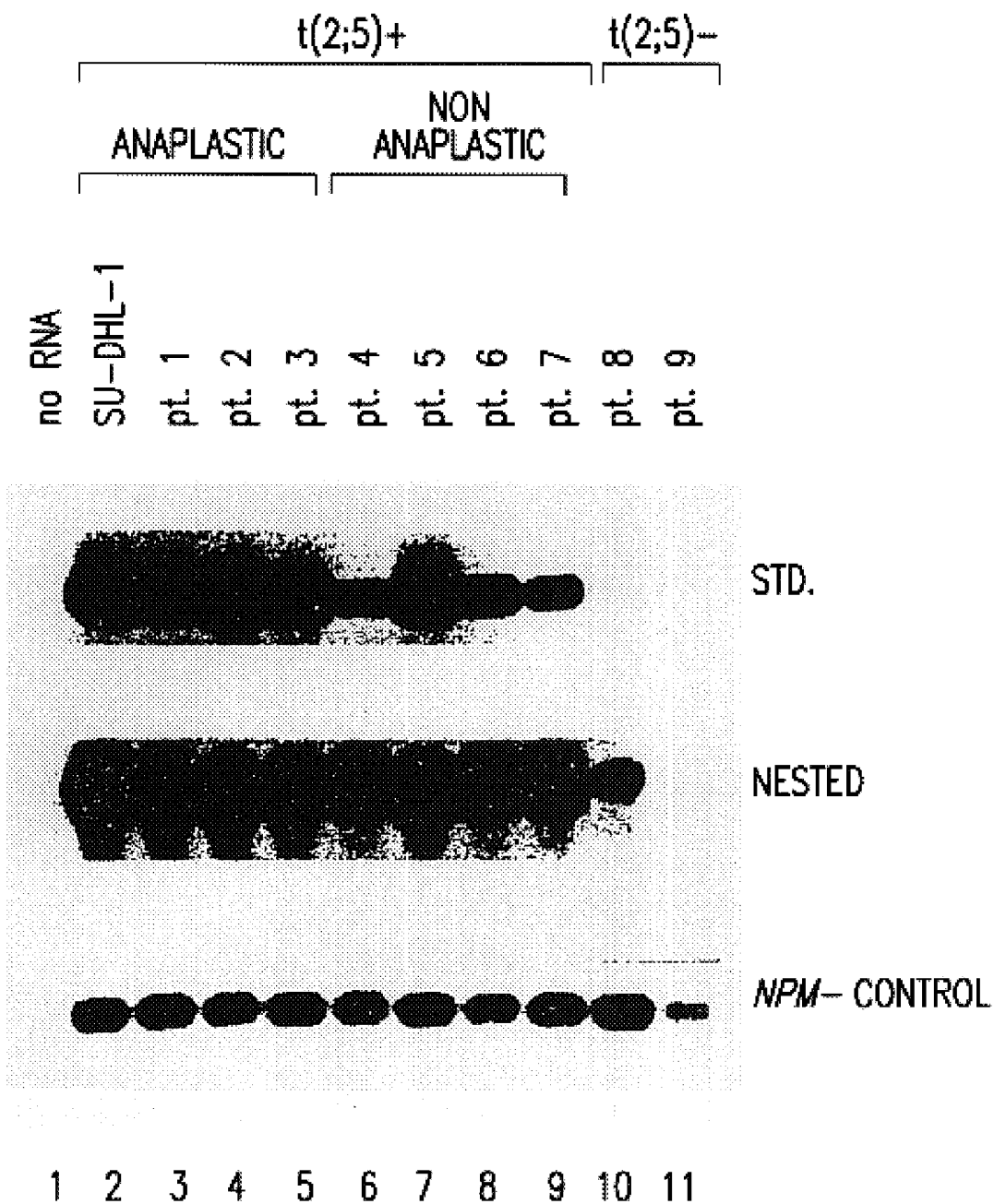
FIG. 6: RT-PCR analysis of NHL biopsy samples for detection of the NPM/ALK fusion transcript. Total RNAs (1 µg) prepared from the Ki-1 ALCL cell line SU-DHL-1 or from NHL samples were subjected to RT-PCR using primers homologous to NPM or ALK sequences immediately flanking the NPM/ALK fusion junction ("Std." and "Nested"), or a primer pair homologous to sequences of the ubiquitously expressed normal NPM gene as a control for RNA integrity and RT-PCR techniques ("NPM/control"). Southern hybridizations of the NPM/ALK RT-PCR products using an end-labeled 24-mer homologous to DNA sequences at the fusion junction, or of the NPM products with a 24-mer that hybridizes to normal NPM sequences, are shown. Note that all cytogenetically positive cases and one of two cytogenetically negative cases express NPM/ALK and that all fusion junctions are identical.

The molecular characterization of the t(2;5) has allowed the development of a reverse transcriptase-polymerase chain reaction (RT-PCR) assay for rapid and sensitive detection of the NPM/ALK transcript. To better define the spectrum of lymphomas that contain the t(2;5), 50 cases of large cell NHL were analyzed for expression of the NPM/ALK message using this assay (FIG. 6). NPM/ALK transcripts were detected in 16/16 cases of NHL that contained the t(2;5) by cytogenetic analysis and 5/34 cases that either lacked evidence of the translocation or had unsuccessful cytogenetic studies. Histologically, these NPM/ALK-positive cases included 10 anaplastic large cell lymphomas (ALCLs), 8 immunoblastic lymphomas, and 3 diffuse large cell lymphomas. In all cases, the NPM/ALK PCR products were of identical size and sequence, suggesting that the genomic chromosome breaks were clustered in a single intron in both NPM and ALK.

Interestingly, in one case in which cytogenetics revealed clonal chromosomal structural abnormalities but failed to identify abnormalities of chromosomes 2 or 5, NPM/ALK transcripts were identified. Thus, cytogenetic studies are inadequate for identification of t(2;5) in some cases. These data demonstrate that the methods and oligonucleotide primers of the invention allow for the detection of the NPM/ALK message reproducibly in clinical material.

C. Expression Constructs Containing NPM/ALK Genes and Recombinant Production of NPM/ALK Proteins The nucleic acid sequences of the present invention can be inserted into an expression vector in order to produce proteins having the amino acid sequences of the present invention. There are numerous host/vector systems available for the propagation of nucleic acid sequences and the production of expressed proteins (see, for example, Sambrook et al., eds., *Molecular Cloning: A Laboratory Manual*, Cold Spring Harbor Press, Cold Spring Harbor, N.Y. (1989); P. Liljeström et al., Chapter 16, "Protein Expression," in *Current Protocols in Molecular Biology*, F. M. Ausubel et al., eds., John Wiley & Sons, Boston, Mass. (1994), pp. 16.0.1–16.20.16)). As this Example illustrates, one skilled in the art can readily adapt any host/vector system which is capable of propagating or expressing heterologous DNA to express the genetic sequences of the present invention. An entire NPM/ALK protein can be generated in this manner. Alternatively, fragments of NPM/ALK may be prepared either by genetic expression in an appropriate host/vector system, or by in vitro synthesis, and used for a variety of purposes, such as the generation of antibodies specific for that fragment. Similarly, NPM/ALK may be fused with known polypeptide sequences to generate novel fusion proteins, such as NPM/ALK derivatives having an affinity tag, for example. Expression constructs containing NPM/ALK sequences are also used to create cells or transgenic non-human animals which express NPM/ALK proteins in vivo; such cells and animals are in turn used in further embodiments of the invention (see Example 3(G)).

D. Antibodies to NPM/ALK Proteins

Figure 9:
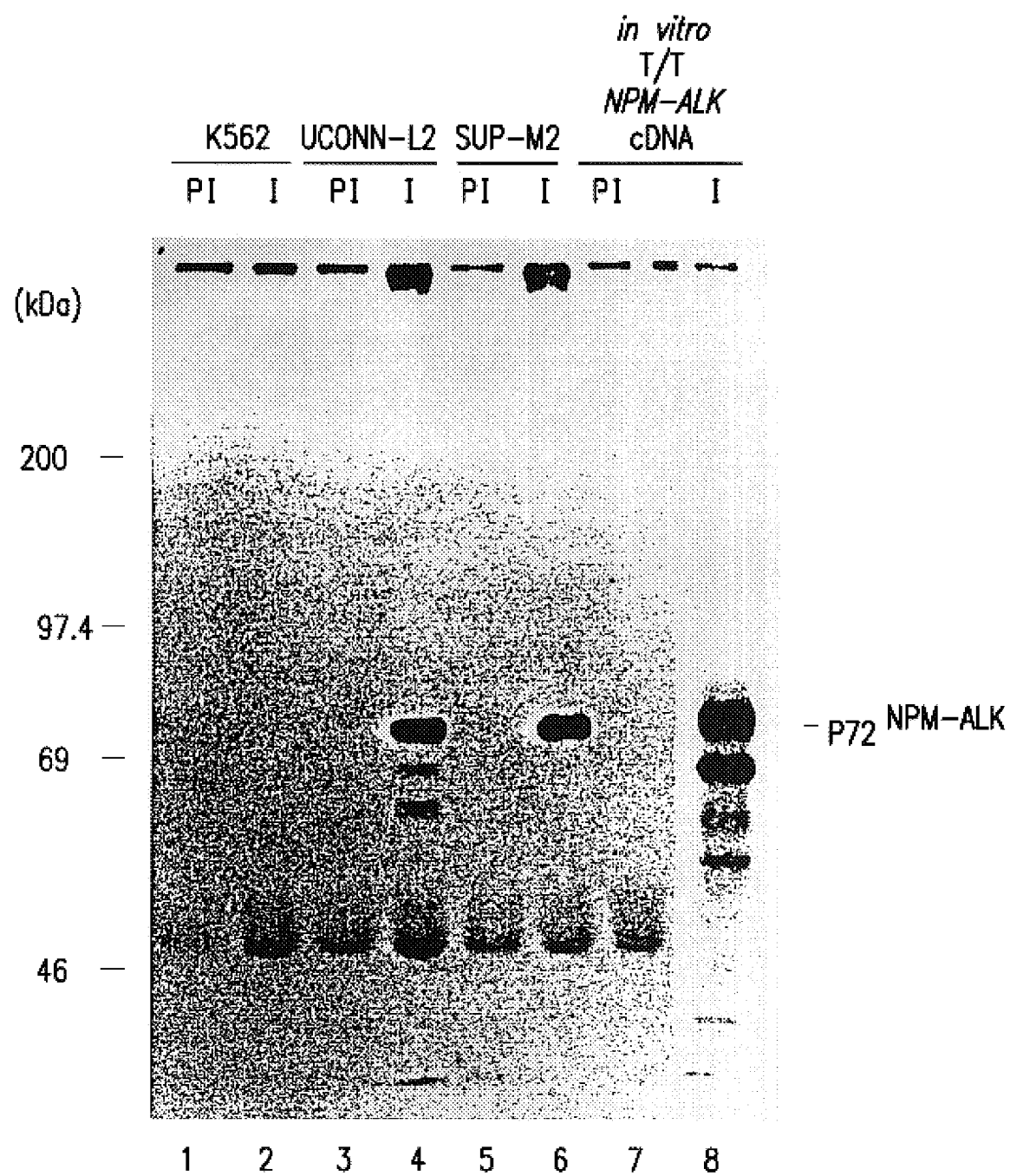
FIG. 9: Detection of the NPM/ALK product from lysates of t(2;5)-positive lymphoma cell lines UCONN-L2 and SUP-M2, and from in vitro transcription/translation of a NPM/ALK cDNA clone, using ALK-specific antiserum. An anti-ALK IP/Western of lysates of the lymphoma cell lines, together with the t(2;5)-negative K562 cell line, is shown. The immunoprecipitated [$^{35}$S]Met-labeled NPM/ALK protein produced in vitro (lane 8) was electrophoresed on the same gel but visualized directly by autoradiography subsequent to membrane transfer. The bands seen below the 72 kDa NPM/ALK protein in lane 4 represent proteolytic degradation products.

The present invention further provides methods of detecting the presence of the NPM/ALK fusion which are based on antibody detection systems. Specifically, because a NPM/ALK fusion protein is expressed in t(2;5) lymphoma cells, antibodies which identify the fusion protein can be used to detect the presence of the NPM/ALK fusion protein as an indication that such cells are present in a sample (FIG. 9).

For example, the NPM/ALK fusion protein can be detected by a method comprising the steps of (a) contacting a sample with two antibodies, wherein a first antibody is capable of binding to NPM, and a second antibody is capable of binding to ALK and (b) detecting the presence of a protein in the sample which binds both the first and the second antibodies.

Alternatively, due to the unique nature and sequence of the fusion protein created by the NPM/ALK fusion, a single antibody which binds selectively the fusion protein can be generated and used to identify the NPM/ALK fusion protein. Further, antibodies may be generated which are specific for either unique structural regions of the NPM/ALK protein or a component of the fusion protein not normally present in the cell type being assayed for NPM/ALK expression. For example, since the ALK protein is not normally expressed in t(2;5) hematopoietic cells (FIG. 5(A)), antibodies specific for this protein can be used to detect the presence of the NPM/ALK fusion protein in such cells.

In one embodiment, a NPM/ALK fusion protein is detected using two sets of antibodies, one set comprising an antibody capable of binding to the NPM protein and the other set comprising an antibody capable of binding to the ALK protein. Specifically, such a method comprises the steps of (a) contacting a sample with two antibodies, wherein a first antibody is capable of binding to NPM, and a second antibody is capable of binding to ALK, and (b) detecting the presence of proteins in the sample which bind to both the first and the second antibody.

In another example of the above methods, the antibodies are labeled such that a signal is produced when the two antibodies bind to the same molecule. One such system is described in U.S. Pat. No. 4,663,278.

In another embodiment of an antibody based detection system, a single antibody is employed which is capable of binding to an epitope which is present at the fusion junction of the NPM/ALK fusion protein but which is not present in the non-fusion NPM or ALK proteins. The fusion junction of the NPM/ALK fusion protein is described in FIG. 2(A). A skilled artisan can readily employ the amino acid sequence of the fusion junction to generate peptide antigens for use in the above described methods of generating antibodies.

The antibodies utilized in the above methods can be polyclonal, monospecific or monoclonal antibodies, as well fragments of these antibodies. In general, techniques for preparing monoclonal antibodies are well known in the art (Campbell, A. M., *Monoclonal Antibody Technology: Laboratory Techniques in Biochemistry and Molecular Biology*, Elsevier Science Publishers, Amsterdam, The Netherlands (1984); St. Groth et al., *J. Immunol. Methods* 35:1–21 (1980)). For example, an antibody capable of binding the NPM or ALK protein can be generated by immunizing an animal with a polypeptide whose sequence is obtained from a region of the NPM or ALK proteins which are present in the NPM/ALK fusion protein.

Monospecific Antibodies to Residues 419–520 of the NPM/ALK Protein

A 303 bp AccII/PstI restriction fragment derived from the NPM/ALK cDNA which encodes ALK-specific residues 419–520 of the NPM/ALK fusion protein (SEQ ID NO:4), corresponding to residues 1359–1460 of the normal ALK protein (SEQ ID NO:2), was ligated in-frame into the pQE bacterial expression vector (QIAexpress Expression System, Qiagen, Chatsworth, Calif.) in order to produce an ALK polypeptide containing an amino-terminal tag of six consecutive histidine residues for binding to nickel-nitriloacetic acid (Ni-NTA) agarose. The resultant expression construct is named pQE-ALK$_{419-520}$. The vector construct pQE-ALK$_{419-520}$ has an in-frame fusion of NPM/ALK residues 419–520 to a vector-encoded amino-terminal 6xHis affinity tag. The ALK$_{419-520}$-6xHis protein was expressed in M15 (pREP4) *E. coli* cells and purified by metal chelate affinity chromatography using Ni-NTA agarose columns (Qiagen, Chatsworth, Calif.), essentially according to the manufacturer's instructions.

NPM/ALK-binding (and ALK-binding) monospecific antiserum was raised by immunizing rabbits with the purified ALK$_{419-520}$-6xHis protein according to standard methods (Chapter 5, "Immunizations," in E. Harlow et al., *Antibodies: A Laboratory Manual*, Cold Spring Harbor Press, Cold Spring Harbor, N.Y. (1988), pp. 53–137; H. M. Cooper et al., in *Current Protocols in Molecular Biology*, F. M. Ausubel et al., eds., John Wiley & Sons, Boston, Mass. (1994), pp. 11.12.1–11.12.6). Serum from rabbits bled prior to immunization was used for preimmune controls. High titer serum was obtained that specifically immunoprecipitates and immunoblots the NPM/ALK protein from lysates of t(2;5)-containing lymphoma lines and immunoprecipitates [$^{35}$S]Met-labeled NPM/ALK produced by in vitro transcription/translation of a cDNA clone (FIG. 9).

NPM/ALK monospecific antiserum identifies a 72 kDa protein unique to the t(2;5)-positive cell lines (FIG. 9, lanes 4 and 6) that is of the size predicted by the deduced amino acid content of the NPM/ALK cDNA and that co-migrates with the immunoprecipitated in vitro transcription/translation product of this clone (FIG. 9, lane 8). The identity of this protein as NPM/ALK was further confirmed by immunoprecipitation and immunoblotting experiments using NPM-specific antibodies (e.g., see FIG. 11).

EXAMPLE 2

ALK Tyrosine Kinase/Receptor

A. Molecular Structures of Normal ALK Genes and Proteins

A cDNA library was prepared from a rhabdomyosarcoma cell line, Rh30 (Douglass, E. C., et al., *Cytogenet. Cell Genet.* 45:148–155 (1987)), in the vector λgt22A (GIBCO/BRL, Gaithersburg, Md.). The Rh30 cDNA library was screened for ALK-positive members using the pS1.2 ALK clone as a probe. Analysis of the nucleotide sequences of the inserts of the two largest ALK-positive clones, pRMS4 and pRMS17-2, revealed 3' ALK sequences identical to those in the NPM/ALK fusion gene cDNA.

Overlapping ALK-positive clones were sequenced in order to determine a full-length normalALK cDNA sequence. Double-strand DNA templates were sequenced using dye-terminators and Taq sequencing methods as recommended by the manufacturer (Perkin Elmer/Applied Biosystems, Inc, Norwalk, Conn.). Samples were electrophoresed and analyzed on PE/ABI 373 and 373 Stretch DNA sequencers. Contig assembly was performed using Staden's X-windows software and the consensus sequence was analyzed using the Wisconsin Package v. 8.0 software (Genetics Computer Group, Inc., Madison, Wis.) and National Center for Biotechnology resources (BLAST, FARFETCH, etc.).

Analysis of the nucleotide sequence (SEQ ID NO: 1) of the 6,226 bp insert of RMS 17-2 identified an ATG codon at nucleotides 912–914 which initiates an open reading frame that is composed of a total of 4,860 bp and encodes a 1,620 amino acid polypeptide with a predicted molecular weight of approximately 177 kilodaltons (kDa). The nucleotide sequence surrounding the ATG encoding the ALK initiator methionine (GGCGGGA TGG) (SEQ ID NO:42) is in agreement with the consensus translation initiation sequence reported by Kozak (*Nucleic Acids Research* 15:8125–8132 (1987)) and is preceded by two in-frame termination codons within 45 bp upstream of this site. A 455 bp 3' untranslated region terminates in a poly (A) tail that is preceded, 20 bp upstream, by the canonical polyadenylation signal AATAAA.

No mutations, other than the translocation which generated the fusion gene, have been observed in the chimeric NPM/ALK gene when compared to the normal NPM and ALK sequences. Sequences of ALK immediately upstream of the NPM/ALK junction encode a 28 hydrophobic amino acid stretch typical of a transmembrane domain (FIG. 2(B); SEQ ID NO:7) flanked on its cytoplasmic side by basic amino acid residues typical for the junction between transmembrane and cytoplasmic domains. Sequences 5' from this region encode a 1,030 amino acid putative extracellular domain containing an amino-terminal 26 amino acid hydrophobic region consistent with known signal peptide sequences. The presence of these sequences indicates that the normal ALK product is a membrane-spanning tyrosine kinase receptor. Significantly, the transmembrane segment and putative extracellular ligand binding domain are not included in the NPM/ALK fusion protein.

Comparison of ALK with known PTK family members indicates greatest homology to members of the insulin receptor kinase subfamily, including leukocyte tyrosine kinase (LTK; 57% amino acid identity with ALK residues 605–1,509), and a lesser degree of homology, restricted to the region of the kinase domain, with other family members including TRKA (38%), ROS (37%) and its Drosophila homologue Sevenless (35%), the β-chain of the insulin-like growth factor-1 receptor (IGF1R; 37%) and the β-chain of the insulin receptor (IR; 36%) (J. J. Krolewski et al., *EMBO J*. 10:2911–2919 (1991); H. Toyoshima et al., *Proc. Natl. Acad. Sci. USA* 90:5404–5408 (1993); D. Martin-Zanca et al., *Nature* 319:743–748 (1986); H. Matsushime et al., *Mol. Cell. Biol.* 6:3000–3004 (1986); J. M. Chen et al., *Oncogene.* 6:257–264 (1991); K. Basler et al., *Cell* 54:299–311 (1988); D. D. Bowtell et al., *Genes and Development* 2:620–634 (1988); A. Ullrich et al., *EMBO J*. 5:2503–2512 (1986); A. Ullrich et al., *Nature* 313:756–761 (1985); Y. Ebina et al., *Cell* 40:747–758 (1985)).

The normal ALK receptor is a member of the insulin receptor (IR) kinase family, containing in its kinase domain the paired tyrosine residues that form the major regulatory autophosphorylation site unique to the members of this group (Hanks, S. K., et al., *Science* 241:42–52 (1988)). These PTKs include a number of proto-oncogenes that were initially isolated because of their ability to transform rodent fibroblasts in transfection experiments with genomic DNAs extracted from malignant human tissue (e.g., MET, TRK and AXL) (O'Bryan, J. P. et al., *Mol. Cell. Biol.* 11:5016–5031 (1991)). Within the IR kinase family, ALK shows the greatest homology to leukocyte tyrosine kinase (LTK). This relationship suggests that NPM-ALK could function in lymphomagenesis in part as a dysregulated LTK. LTK is expressed mainly in hematopoietic cells including pre-B lymphocytes, some mature B and T cells, and leukemic cells of the lymphoid, erythroid, or myeloid lineage; however, its characterization to date (Ben-Neriah, Y. and Bauskin, A. R., *Nature* 333:672–676 (1988); Bernards, A. and de la Monte, S. M., *EMBO J*. 9:2279–2287 (1990); Toyoshima, H. et al., *Proc. Natl. Acad. Sci. U.S.A.* 90:5404–5408 (1993)) offers few clues to its likely role in hematopoiesis. Analysis of LTK has been complicated by the identification of multiple alternatively spliced LTK messages, together with the inability of numerous investigators to identify LTK protein(s) in vivo, presumably because of low levels of expression. Differently spliced LTK cDNAs predict cytoplasmic isoforms, a transmembrane receptor with or without a kinase domain, and a soluble receptor protein; it is unknown which of these forms may be functionally relevant (Toyoshima, H. et al., *Proc. Natl. Acad. Sci. U.S.A.* 90:5404–5408 (1993)). Based on their relatedness, it appears that ALK and LTK are members of an RTK subclass within the IR family similar to the IR/IGF-1R, the TRK receptors, and the MET/RON/SEA receptor subgroups.

Comparisons of the cysteine-rich domain of the IGF-I receptor, known to determine ligand specificity (Gustafson, T. A. and Rutter, W. J., *J. Biol. Chem.* 265:18663–18667 (1990)), and of the ligand-binding domain of the IGF-II receptor, to the extracellular portion of ALK indicate that neither IGF-I nor IGF-II are likely to be ligands for ALK. Similar comparisons of the extracellular portion of the other insulin receptor (IR) family members for which a cognate ligand has been identified, TRK (nerve growth factor) and MET (hepatocyte growth factor/scatter factor), also indicate that the ALK ligand is likely to be unique.

B. Detection of ALK Nucleic Acid Sequences and Expression of ALK Genes In Vivo

Hybridization Assays

The methods of Southern and Northern blot hybridization (Sambrook et al., eds., *Molecular Cloning*, Cold Spring Harbor Press, Cold Spring Harbor, N.Y. (1989)) are employed using probes derived from the nucleic acid sequences of the invention to determine if a sample contains an ALK nucleic acid sequence. Methods of detecting ALK sequences are necessary for some embodiments of the invention; for example, to identify and isolate ALK sequences from non-human animals, or to identify cells or non-human animals genetically engineered to contain and express the human ALK gene. Moreover, mutations (e.g., restriction fragment length polymorphisms (RFLPs), insertions, deletions) in ALK genes can be detected by such methods for diagnostic or screening (risk assessment) purposes.

One such method comprises the steps of (a) contacting a sample with a nucleic acid probe, wherein the nucleic acid probe is capable of hybridizing to a nucleic acid sequence encoding ALK, and (b) detecting the presence of nucleic acid hybrids in the sample which comprise the nucleic acid probe hybridized to the nucleic acid sequence encoding ALK. A probe capable of hybridizing to a 5' portion of the nucleic acid sequence encoding ALK which is not found in the NPM/ALK fusion is used in step (a) of this method to specifically detect nucleic acids having ALK sequences.

Any method known in the art can be utilized to label the probes used in the above assay methods. In the two probe embodiment, the first and the second probe can be labeled with different radioisotopes, enzymes or chromophores. Using the differently labeled probes, one can identify DNA sequences which bind one or both of the probes. In another application, the first and the second probe can be labeled in such a fashion that a signal is produced when the probes hybridize to the same nucleic acid fragment. One example of such a procedure is provided in U.S. Pat. No. 4,820,630.

In one application of the above described methods, one of the nucleic acid probes is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

Detection of ALK Sequences by Northern Assays

ALK mRNAs of 6.5 kb and 8.0 kb were readily identified in small intestine and rhabdomyosarcoma cell lines, and were weakly expressed in brain (fetal and adult), colon and prostate (FIGS. 1(B) and (C)). Abundant amounts of 4.4 kb and 6.0 kb mRNAs were detected in testis, whereas placenta and fetal liver each expressed a single 6.0 kb transcript. All four mRNAs were also detected with a probe that contains only 3' untranslated ALK sequences, suggesting that they represent differentially spliced ALK mRNAs, not cross-hybridizing transcripts of other PTK genes. ALK transcripts were not detected in normal spleen, thymus, peripheral blood leukocytes, B-lymphoblastoid cell lines, phytohemagglutinin-stimulated T lymphocytes or t(2;5)-negative leukemia/lymphoma cell lines of myeloid or B- or T-lymphoid derivation, implying that they are not normally expressed in hematopoietic cells.

Detection of ALK Sequences by In Situ Hybridization

Murine developmental expression of Alk was examined by in situ hybridization analysis using the reverse complement of the sequence of the murine Alk juxtamembrane exon (that is, the reverse complement of SEQ ID NO:11) as a probe (FIG. 7). In a day 12 mouse embryo, Alk mRNA (i.e., antisense-binding RNA) is demonstrable in the ventral horns of the spinal cord, and in the trigeminal, facial, and acoustic ganglia, but a control Alk sense strand probe (the coding strand sequence of the murine Alk juxtamembrane exon; SEQ ID NO:11) yields no detectable signal. A day 16 mouse embryo hybridized with the Alk antisense probe results in an intense signal along the entire length of the developing spinal cord.

PCR Assays

In general, an amplification reaction such as the polymerase chain reaction (PCR) is used to amplify either a mRNA molecule encoding the ALK protein, or a genomic DNA molecule containing ALK sequences. Specifically, utilizing the sequences of the identified ALK genes, the present invention provides methods of identifying the presence of a nucleic acid sequence in a sample which contains the ALK sequence comprising the steps of (a) contacting a sample with two nucleic acid amplification primers, wherein the first nucleic acid amplification primer is capable of hybridizing to a specific sequence on the nucleic acid "sense" (ALK-encoding) strand and the second nucleic acid amplification primer is capable of hybridizing to a specific sequence on the nucleic acid "antisense" (reverse complement) strand of ALK, (b) amplifying the primed nucleic acid sequences in the sample, and (c) detecting the presence of amplified nucleic acid sequence in the sample which contains ALK sequences.

As used herein, an amplification primer is any short DNA sequence which can hybridize to a target sequence and allow the target sequence to be amplified when incubated with the appropriate reagents under the appropriate condition. (See, for example, P. Liang et al., Chapter 15, "The Polymerase Chain Reaction," in Ausubel et al., *Current Protocols in Molecular Biology*, Wiley Press, Boston, Mass. (1993), pp. 15.0.1–15.8.8). Amplification requires the use of two primers which flank the region which is to be amplified. One primer hybridizes to the target sequence while the other primer hybridizes to a sequence complementary to the target sequence. In order to achieve specific priming for amplification reactions, it is generally necessary that amplification primers be from about 18 to about 30 nucleotides in length (M. A. Innis et al., "Optimization of PCRs," Chapter 1, and R. K. Saiki., "Amplification of Genomic DNA," Chapter 2, in *PCR Protocols: A Guide to Methods and Applications*, M. A. Innis et al., eds., Academic Press, San Diego, Calif. (1990), pp. 3–20); Privitera et al., *Blood* 79:1781–1788 (1992)). A skilled artisan can readily employ techniques known in the art to prepare fragments of the ALK genes that can be used as primers in PCR reactions.

The target sequence which is to be amplified can either be the mRNA which encodes the ALK protein, cDNA generated therefrom, or genomic DNA which contains ALK sequences. A skilled artisan can readily employ techniques known in the art to prepare a sample containing the appropriate target molecule (see, e.g., Chapters 7–9 in Sambrook et al., eds., *Molecular Cloning*, Cold Spring Harbor Press, Cold Spring Harbor, N.Y. (1989); and Chapters 2, 4 and 10 in Ausubel et al., eds., *Current Protocols in Molecular Biology*, Wiley Press, Boston, Mass. (1993)).

As used herein, amplification refers to the process of generating multiple copies of a target sequence. Various methods and enzymes are available to accomplish this goal. In the preferred embodiment, Taq-1 DNA polymerase is used in the method known as PCR to amplify the target sequence. However, a skilled artisan can substitute other enzymes for the Taq-1 polymerase so long as the amplification goal is achieved. In general the preferred conditions are characterized as being high stringency conditions. A skilled artisan can readily determine the appropriate conditions (M. A. Innis et al., eds., *PCR Protocols: A Guide to Methods and Applications*, Academic Press, San Diego, Calif. (1990); H. A. Erlich, ed., *PCR Technology: Principles and Applications for DNA Amplification*, Stockton Press, New York, N.Y. (1989)).

As used herein, detecting the amplified target sequence refers to any method which can be employed to determine the presence or absence of an amplified nucleic acid sequence of a given size or a particular sequence. In one application, the amplification product is subjected to agarose or acrylamide gel electrophoresis to resolve the various sizes of nucleic acids which are present in the amplified sample. The resulting gel can then be analyzed visually using a nucleic acid stain, for example ethidium bromide, to determine if an appropriately sized nucleic acid molecule is present in the amplified sample. Alternatively, a detectably labeled probe can be employed to determine if the sample contains the amplified sequence. Such a probe can be used following the above described electrophoresis, or can be used in a dot blot or in situ assay method.

Figure 8A:
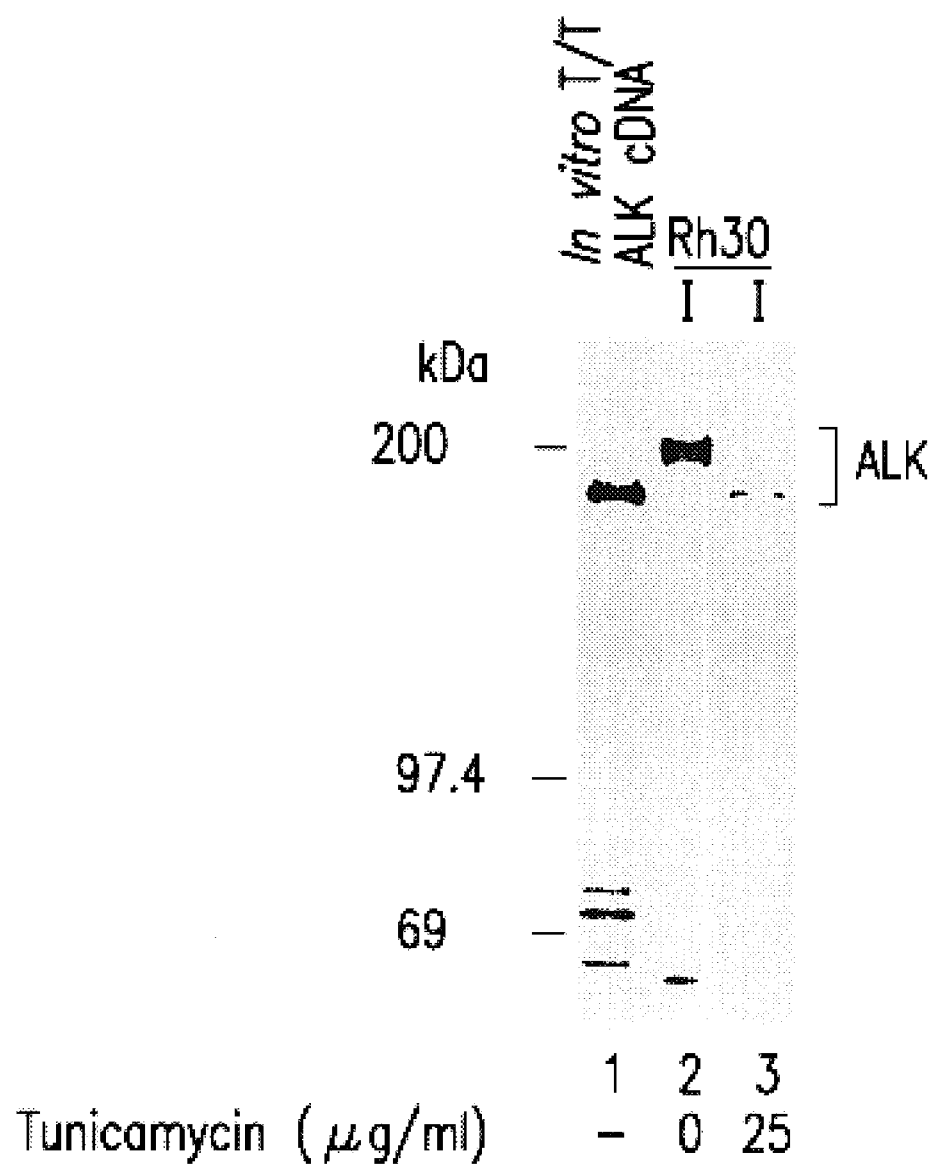
FIGS. 8A–8C Expression of the normal ALK receptor tyrosine kinase in COS-7 cells and in the Rh3O rhabdomyosarcoma cell line. (A) Comparison of the in vitro transcription/translation product of a normal ALK cDNA (lane 1) with the endogenous ALK protein expressed by the Rh30 cell line (lanes 2 and 3). The Rh30 cells analyzed in sample lane 3 were incubated with 25 µg/ml tunicamycin for 30 minutes prior to, and for the 30 minute period of, [$^{35}$S]Met-labeling to inhibit glycosylation of ALK. Proteins were resolved by 6% SDS-PAGE under reducing conditions, then exposed to film overnight at −80° C. Fifteen microliters of a 50 microliter in vitro transcription/translation reaction was loaded directly in sample lane 1; sample lanes 2 and 3 each represent the protein immunoprecipitated from the lysate of a single confluent 100 mm culture dish of Rh30 cells using anti-ALK serum (I). (B) The mature ALK receptor exists as a glycosylated single chain polypeptide with a molecular weight of ~200 kDa. Anti-ALK immunoprecipitates from detergent lysates of [$^{35}$S]Met-labeled cells were resolved by 7.5% SDS-PAGE under reducing (lanes 1–5) or non-reducing (lanes 6 and 7) conditions on the same gel. Reduced and non-reduced samples were separated by multiple lanes to avoid diffusion of β-mercaptoethanol; visualization of non-reduced immunoglobulin in lanes 6 and 7 of the Coomassie-stained gel served as an internal control to exclude diffusion. COS-7/pcDNA3—COS-7 cells electroporated with the "empty" mammalian expression vector pcDNA3 (Invitrogen, San Diego, Calif.); COS-7/pcDNA3-ALK-COS-7 electroporated with an ALK cDNA clone inserted downstream of the CMV major intermediate early promoter/enhancer in pcDNA3; Rh30—Rh30 rhabdomyosarcoma cell line. PI-pre-immune serum; I-anti-ALK serum. Note that the ALK cDNA product expressed in COS-7 cells appears to be correctly modified post-translationally and co-migrates with the endogenous Rh30 ALK receptor. Also note that the relative mobility of ALK in SDS-PAGE is the same under reducing and non-reducing conditions. The faster migrating bands in lanes 3 and 5 immediately below the 200 kDa ALK protein represent the products of proteolytic degradation. (C) Cell surface biotinylation experiments indicate that the ALK protein produced by pcDNA3-ALK in COS-7 cells is correctly inserted into the cell membrane. Intact COS-7 cells previously electroporated with either the pcDNA3 mammalian expression vector alone (lane 1), or a pcDNA3 construct containing the RMS17-2 ALK cDNA (lanes 2 and 3), were surface-labeled by biotinylation and the cells lysed in RIPA buffer subsequent to quenching of the labeling reaction. The lysates were incubated with preimmune (PI) or anti-ALK (I) serum, proteins were resolved by 7.5% polyacrylamide SDS-PAGE, transferred to a PVDF membrane, and detected by chemiluminescence.

C. Expression Constructs Containing ALK Genes and Recombinant Production of ALK Proteins ALK Expression Constructs A molecular weight of ~177 kDa for the normal ALK protein is predicted from the ALK nucleotide sequence and a protein product, having an apparent molecular weight of 177 kDa in SDS-PAGE, is produced by in vitro transcription/translation of the full-length ALK clone pRMS17-2 (FIG. 8(A)). To confirm that the ALK cDNA encodes a full-length receptor, the complete 6,226 bp SalI/NotI ALK cDNA insert from RMS/7-2 was subcloned into the EcoRV/NotI-digested CMV promoter-based mammalian expression vector pcDNA3 (Invitrogen, San Diego, Calif.) following Klenow polymerase fill-in of the SalI overhang. The resultant expression construct is designated pcDNA3-ALK. In vitro transcription and translation with this construct was performed using the $T_NT$ coupled reticulocyte lysate system (Promega, Madison, Wis.) and T7 polymerase. Transient expression studies of this ALK plasmid and pcDNA3 "empty" vector (as a negative control) in COS7 monkey kidney epithelial cells were performed by electroporation in 0.4 cm cuvettes (960 $\mu$F, 250V). Cells were used for experiments at 72-96 hours post-electroporation.

Figure 8B:
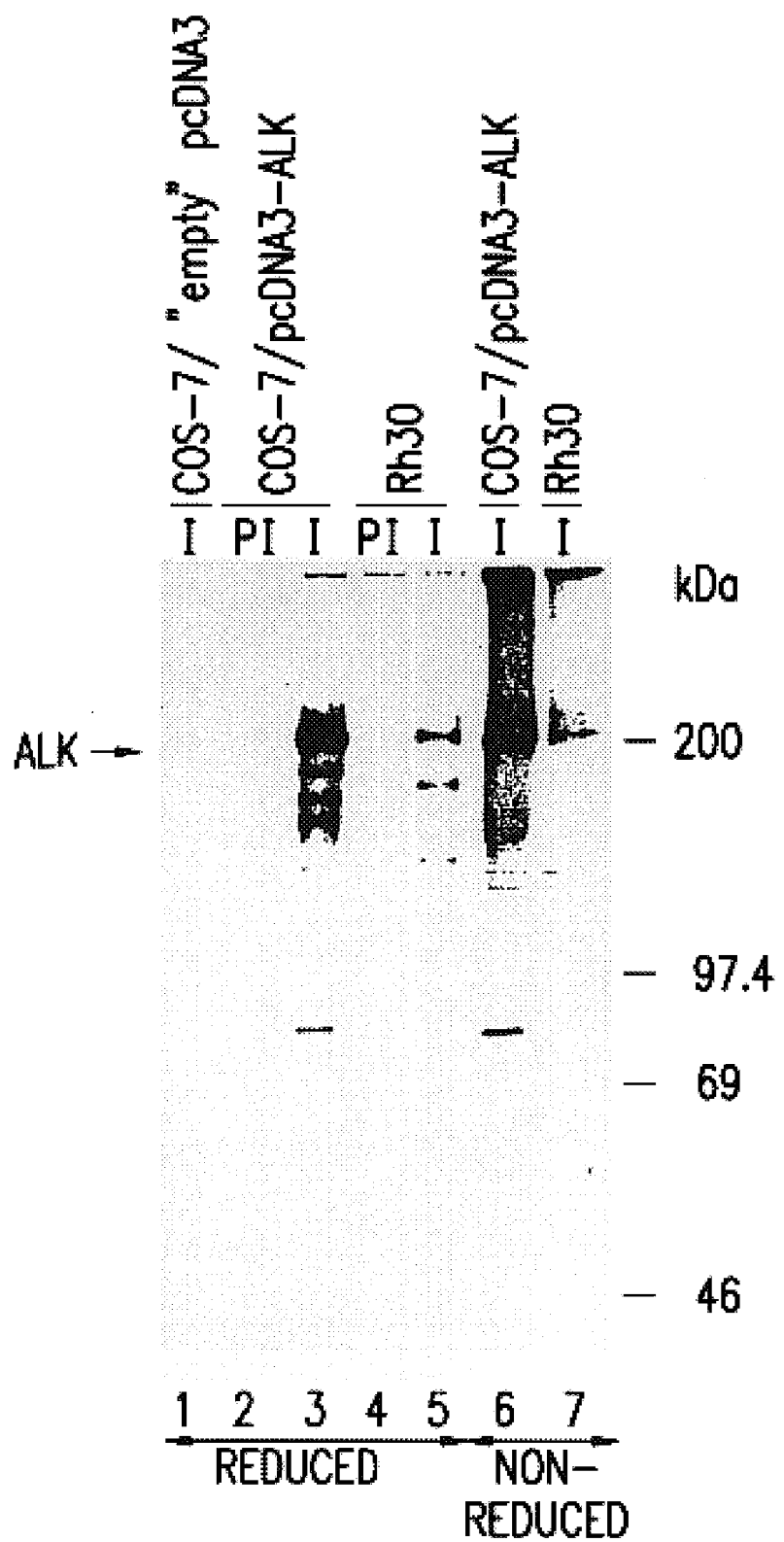

Plasmid pcDNA3-ALK was electroporated into COS-7 and, seventy-two hours post-electroporation, these cells were metabolically labeled with [$^{35}$S]methionine and subjected to immunoprecipitation analysis using polyclonal ALK antibody (Example 2(D)). Expression of pcDNA3-ALK in COS-7 results in the production of a single immunoreactive protein of approximately 200 kDa, slightly larger than the 177 kDa in vitro transcription and translation product derived from ALK cDNA clone RMS17-2 but identical in size to the endogenous ALK protein immunoprecipitated from the Rh30 rhabdomyosarcoma cell line (FIG. 8(B)). This 200 kDa protein ($gp200^{ALK}$) is not detected in COS-7 cells electroporated using "empty" pcDNA3 vector, nor in control immunoprecipitations from lysates of either COS-7 electroporated with pcDNA3-ALK or from Rh3O cells using preimmune serum.

Glycosylation of ALK Protein

The difference in the size of the ALK protein identified in vivo compared with the ALK product resulting from in vitro transcription/translation of the RMS17-2 clone suggested that post-translational modifications of the ALK polypeptide backbone occur during the synthesis of the mature receptor. Because the deduced amino acid sequence of ALK contains multiple sites for potential N-linked glycosylation, experiments were conducted to determine whether the mature 200 kDa receptor is a glycoprotein by performing metabolic labeling experiments using the glycosylation inhibitor tunicamycin (FIG. 8(A)). Pre-incubation of Rh30 cells with a concentration of tunicamycin expected to totally inhibit glycosylation (25 µg/ml) revealed the presence of a single immunoreactive polypeptide identical in size to the 177 kDa in vitro transcription/translation product of the ALK cDNA. Thus, it appears that the size difference between the ALK polypeptide core and the mature receptor results from the addition of carbohydrate moieties.

To further examine the in vivo processing of ALK, a series of pulse-chase labeling experiments using Rh30 cells were performed as follows. Following incubation for 30 minutes in growth media lacking methionine, these cells were pulse-labeled with [$^{35}$S]methionine for 15 minutes, then chased with media containing excess cold methionine and lysed for immunoprecipitation analysis at various time points. Glycosylated 200 kDa ALK protein was identified even immediately after the end of the 15 minute [$^{35}$S]methionine-labeling period. Because no proteins of lower molecular mass were recognized by our polyclonal ALK antiserum, it is likely that nascent polysome-bound ALK polypeptides become glycosylated during their synthesis while being transported into the endoplasmic reticulum. Further oligosaccharide processing of ALK within the Golgi apparatus then presumably occurs prior to transit to the cell membrane, resulting in a mature ALK glycoprotein of essentially identical molecular mass as the immature ER glycoprotein form. The possibility exists that ALK may undergo a very prolonged ER/Golgi transit period that exceeds the five hour chase duration used in these studies. However, the production of late-appearing, Golgi-processed, glycosylated forms of the receptor that are of significantly different molecular mass compared to the 200 kDa molecules identified in these [$^{35}$S]methionine-labeling experiments can be excluded because only the 200 kDa receptor form is identified in cell surface labeling experiments (detailed in the immediately following subsection), immunocomplex kinase assays (Example 3(C)), and anti-ALK immunoblots that would detect steady-state levels of any ALK receptors that were further glycosylated.

Other receptors in the insulin RTK subfamily have been shown to possess varied structural characteristics of their mature forms, although each is initially translated as a single polypeptide produced from a single gene locus. For example, the insulin and insulin-like growth factor-1 receptors possess a disulfide-linked heterotetrameric $\alpha_2\beta_2$ structure, the MET and RON RTKs exist as $\alpha\beta$ disulfide-linked heterodimers, and the mature TRK RTKs (TRK-A, -B, and -C) are present in the cell membrane as monomeric proteins. As noted above, the ALK receptor immunoprecipitated in metabolic labeling studies from both COS-7 cells electroporated with the pcDNA3-ALK expression construct and from the Rh30 cell line is present as an apparently single prominent 200 kDa glycoprotein when analyzed in SDS-PAGE under reducing conditions; no larger precursor molecules that might subsequently be post-translationally cleaved into subunit proteins, nor smaller bands that could represent subunit fragments that are normally linked via disulfide bonds, were seen in either steady-state or pulse-chase labeling studies. Further evidence that the mature ALK receptor does not possess a disulfide-linked multi-subunit structure (as found with the IR, IGF-1R, MET, and RON RTKs) was provided in metabolic labeling experiments in which the ALK receptor observed under non-reducing conditions co-migrated with the 200 kDa glycoprotein identified in the reduced state (FIG. 8(B)). These observations indicate that, like the TRK RTKs, ALK exists in its mature form as a single chain receptor with a single (based upon its amino acid sequence) membrane-spanning segment.

ALK is a Membrane-Spanning Receptor

In order to provide biochemical evidence for the hypothesis that ALK encodes a membrane-spanning receptor, biotinylation of COS-7 cells that had been electroporated with pcDNA3-ALK was performed to selectively label cell surface proteins. Lysates from cells analyzed in surface biotinylation experiments were prepared using radioimmunoprecipitation assay (RIPA) buffer (150 mM NaCl, 1% NP-40, 0.5% DOC, 0.1% SDS, 50 mM Tris, pH 7.2) containing 0.5% aprotinin, 1 mM PMSF, 2 mM EDTA, and 1 mM $Na_3VO_4$. Cell lysates were clarified of insolubles by a two-minute centrifugation at 14,000 RPM in a microfuge, then incubated for two hours at 4° C. with a 1:100 dilution of either preimmune serum or anti-ALK rabbit serum. Immunoprecipitates were collected by a one hour incubation at 4° C. with 40 microliters (µl) of a 1:1 (vol:vol) slurry of protein A-Sepharose (CL-4B; Pharmacia, Piscataway, N.J.) in phosphate-buffered saline, and were extensively washed with RIPA buffer before suspension in Laemmli's sample buffer with 5% 2-mercaptoethanol. The protein samples were then analyzed by SDS-polyacrylamide gel electrophoresis (PAGE) on 7.5% polyacrylamide gels.

Biotinylation of cell surface proteins was performed as described by Meier et al. (*Analytical Biochemistry* 204:222–226 (1992)), with minor modifications. Briefly, cells were washed twice with warm phosphate-buffered saline, once in room temperature biotinylation buffer (10 mM Na borate, pH 8.8; 150 mM NaCl), then incubated for 15 minutes at room temperature in biotinylation buffer containing 50 µg/ml D-biotinyl-$\Sigma$-aminocaproic acid N-hydroxysuccinimide ester (biotin-CNHS-ester) (Boehringer-Mannheim Corp., Indianapolis, Ind.). The labeling reaction was stopped by addition of $NH_4Cl$ to a final concentration of 10 mM, and the cells were washed extensively in wash buffer (50 mM Tris-HCl, pH 7.4, 25 mM KCl, 5 mM $MgCl_2$, and 1 mM EGTA) prior to lysis in RIPA buffer. Immunoprecipitations were performed exactly as detailed above except that lysates were pre-cleared prior to the addition of preimmune or immune serum by incubating with 40 µl of 1:1 protein A-Sepharose: phosphate-buffered saline for 2 hours at 4° C. Proteins were resolved by 7.5% SDS-PAGE, transferred to polyvinylidene difluoride (PVDF) membrane filters (Immobilon-P, Millipore, Bedford, Mass.) using a semidry blotting system (SemiPhor Transfer unit, Hoefer Scientific Instruments, San Francisco, Calif.). PVDF membranes were incubated for 1 hour at room temperature in blocking reagent (PBS containing 0.1% Tween-20 and 3% non-fat dry milk), followed by three 15 minute room temperature washes with PBS containing 0.1% Tween-20. The membranes were then incubated in streptavidin-biotin-horseradish peroxidase complex diluted 1:100 in PBS containing 0.1% Tween-20 for 1 hour at room temperature, washed in PBS and 0.1% Tween-20 five times for 15 minutes each, and the biotinylated proteins detected by enhanced chemiluminescence (ECL kit, Amersham Life Sciences, Inc., Arlington Heights, Ill.).

Figure 8C:
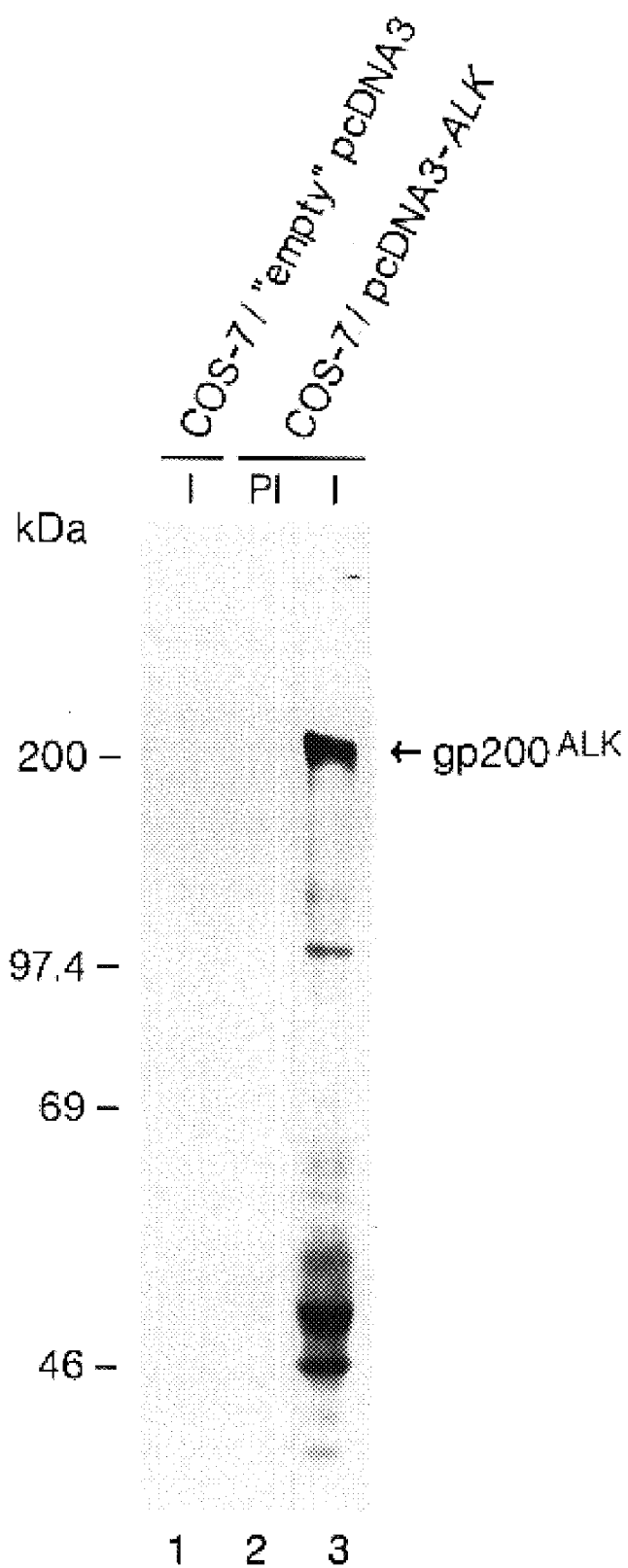

Intact COS-7 cells in tissue culture dishes were biotinylated with biotin-CNHS-ester using conditions previously shown to label cell surface-exposed proteins only, the biotinylation reaction quenched, and the cells lysed. Immunoprecipitation of the lysates prepared from these cells using polyclonal ALK antibody readily detected the mature 200 kDa ALK glycoprotein (FIG. 8(C), indicating that the ALK receptor encoded by pcDNA3-ALK is correctly inserted through the cell membrane with the expected ligand-binding domain exposed extracellularly.

D. Antibodies to ALK Proteins

The present invention further provides methods of detecting ALK proteins which are based on antibody detection systems. For example, the ALK protein can be detected by a method comprising the steps of (a) contacting a sample with an antibody capable of binding to ALK and (b) detecting the presence of an antibody:ALK protein complex in the sample.

The antibodies utilized in the such methods can be polyclonal, monospecific or monoclonal antibodies, as well as fragments of these antibodies. In general, techniques for preparing monoclonal antibodies are well known in the art (Campbell, A. M., *Monoclonal Antibody Technology: Laboratory Techniques in Biochemistry and Molecular Biology*, Elsevier Science Publishers, Amsterdam, The Netherlands (1984); St. Groth et al., *J. Immunol. Methods* 35:1–21 (1980)). For example, an antibody capable of specifically binding the ALK protein can be generated by immunizing an animal with a polypeptide whose sequence is obtained from a region of the ALK protein which is not present in the NPM/ALK fusion protein.

Polyclonal Antibodies

Any animal (mouse, rabbit, etc.) which is known to produce antibodies can be utilized to produce antibodies with the desired specificity. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide selected, and the site of injection. The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or P-galactosidase) or through the inclusion of an adjuvant during immunization. For polyclonal antibodies, antibody containing antisera is isolated from the immunized animal and is screened for the presence of antibodies with the desired specificity.

For a description of one type of polyclonal antiserum, i.e., ALK-binding monospecific antiserum (raised to residues 1359–1460 of ALK), see Example 1(D)).

Monoclonal Antibodies

For generating monoclonal antibodies, spleen cells from the immunized animals are removed, fused with myeloma cells, such as SP2/0-Ag 14 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)). Hybridomas secreting the desired antibodies are cloned and the class and subclass are determined using procedures known in the art (Campbell, A. M., *Monoclonal Antibody Technology: Laboratory Techniques in Biochemistry and Molecular Biology*, Elsevier Science Publishers, Amsterdam, The Netherlands (1984); Chapter 6, "Monoclonal Antibodies," and Chapter 7, "Growing Hybridomas," in E. Harlow et al., *Antibodies: A Laboratory Manual*, Cold Spring Harbor Press, Cold Spring Harbor, N.Y. (1988), pp. 139–281; H. M. Cooper et al., in *Current Protocols in Molecular Biology*, F. M. Ausubel et al., eds., John Wiley & Sons, Boston, Mass. (1994), pp. 11.4.1–11.4.5).

E. ALK Sequences from Non-Human Animals

The human ALK sequence can be employed to identify and isolate ALK sequences from non-human animals. For example, the human ALK sequence is used as a probe to screen cDNA libraries prepared from non-human animals such as *Drosophila melanogaster,* amphibians, mice, cats, dogs, cows, sheep, primates and the like. Once the sequences of two or more ALK genes have been determined, amplification primers based on stretches of conserved sequences are used to amplify ALK sequences from other animals.

For example, a "Southern" assay is used to identify clones from a library of murine cDNA sequences using human ALK DNA sequences as a radiolabeled probe. These ALK-positive clones are isolated, and the nucleotide sequence of the mouse cDNA inserted into the vector in these clones is determined using any standard method of nucleotide sequencing known to those of skill in the art. The human ALK and murine Alk nucleotide sequences are aligned by computer program or by hand, and regions of identical or, at least well-conserved, nucleotide sequence between the ALK genes of the two species are identified. These identical/conserved sequences are used to design oligonucleotides which function as ALK-specific primers to be used in PCR amplifications in which the template DNA is genomic DNA or cDNA from a third mammal (i.e., one which is neither a mouse nor a human) in order to obtain ALK DNA, that can be cloned and sequenced, from said third mammal. Alternatively, human ALK or murine Alk sequences, or oligonucleotides derived therefrom, are labeled and used as probes to identify Alk-positive clones in libraries prepared from genomic DNA or cDNA from a third mammal. In like fashion, Alk sequences from any mammal can be prepared and tested for use in any appropriate embodiment of the present invention. Libraries of cDNA sequences from a variety of mammals may be prepared by methods known in the art or commercially purchased (from, e.g., Stratagene, La Jolla, Calif.) for the purpose of screening for and identifying Alk sequences from non-human, non-murine sources.

Murine Alk Sequences

In order to isolate a genomic murine Alk clone, low stringency screening of a murine genomic library prepared from the CCE embryonic stem cell line was performed using a radiolabeled human ALK cDNA restriction fragment (the SacI fragment extending from bp 2561–4505) as a probe.

A 186 bp murine ALK cDNA fragment that represents the exon encoding the juxtamembrane cytoplasmic residues of the ALK receptor was amplified by PCR using a genomic murine ALK clone as a template. The 186 bp insert (SEQ ID NO:11) was subcloned into pBluescript SK+(Stratagene, La Jolla, Calif.) to produce vector construct pJM$^{Alk}$. The insert in pJM$^{Alk}$ has 91% nucleotide identity to the corresponding segment of human ALK, identifies all ALK transcripts observed in human tissue Northern blots, and produces a single-copy gene pattern in Southern hybridizations of mouse DNA performed at low stringency. Thus, this probe should identify all murine ALK transcripts regardless of alternative splicing and will likely not cross-hybridize with other gene mRNAs.

To obtain additional clues regarding the normal function of the ALK receptor, the chromosomal location of the murine homologue of ALK was determined (Mathew et al., *Cytogenet. Cell. Genet.* 70:143–144 (1995)). The murine Alk locus was assigned to distal chromosome 17 within a region known to be homologous to human chromosome 2p21-p23. To date, this region of mouse chromosome 17 lacks any catalogued mutations that would be likely candidates for involvement by the Alk locus.

EXAMPLE 3

Biological Functions of ALK and NPM/ALK Proteins

A. Intracellular Location of NPM/ALK Proteins

Cell fractionation and immunofluorescence experiments were performed to determine the location of NPM/ALK fusion proteins within cells. Cell fractionation using the t(2;5)-positive line SUP-M2 was performed by briefly incubating cells in a 0.5% NP40-containing isotonic buffer (140 mM NaCl, 1.5 mM $MgCl_2$, 10 mM Tris, pH 7.4) to lyse cellular membranes, followed by a low speed pelleting of intact nuclei (e.g., 2,000 rpm for 5 m at 4° C. in an RT-6000 desktop centrifuge (Sorvall-DuPont, Wilmington, Del.)). The supernatant (membrane/cytosol fraction) and nuclear pellet (washed extensively in phosphate-buffered saline (137 mM NaCl, 2.7 mM KCl, 4.3 mM $Na_2HPO_4.7H_2O$, 1.4 mM $KH_2PO_4$) were solubilized in 1× Laemmli sample buffer and equal amounts of protein (~25 μg each) were resolved by SDS-PAGE, blotted to a membrane, and probed with anti-ALK antibodies produced as described above.

Figure 10A:
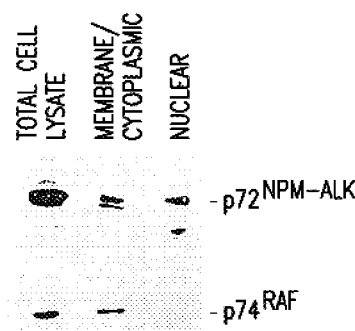
FIGS. 10A–10B NPM/ALK is localized within both the cytosol and nucleus of t(2;5)-positive lymphoma cells. (A) Immunoblot analysis of subcellular fractions of the t(2;5)-positive cell line SUP-M2 using anti-ALK (top panel) or anti-RAF (bottom panel). The identity of the lower band in the membrane/cytoplasmic lane of the anti-ALK blot is unknown, but it may represent partial phosphorylation or proteolytic degradation of NPM/ALK. (B) Immunofluorescent sublocalization of NPM/ALK.

Results from three independent experiments performed in this manner indicated that NPM/ALK is located within both the membrane/cytoplasmic and nuclear fractions, with roughly equal distribution of the total cellular protein between the two (FIG. 10(A)). To exclude membrane/cytosolic contamination of the nuclear fraction, aliquots of each were also immunoblotted with anti-p74RAF; p74RAF is a cytoplasmic protein that can also localize with p21RAS to the inner cell membrane (D. Stokoe, *Science* 264:1463–1467 (1994)).

FIG. 10(A) illustrates that even when four-fold more nuclear fraction (~100 μg protein) as compared to membrane/cytosolic fraction was loaded, little RAF signal was present in the nuclear fraction, indicating minimal membrane/cytosolic contamination. SUP-M2 and UCONN-L2 cell fractionations using a hypotonic cell lysis method without detergent (M. Barbacid et al., *J. Virology* 40:812–821 (1981)), followed by ultracentrifugation through a sucrose cushion yielded identical results.

Figure 10B:
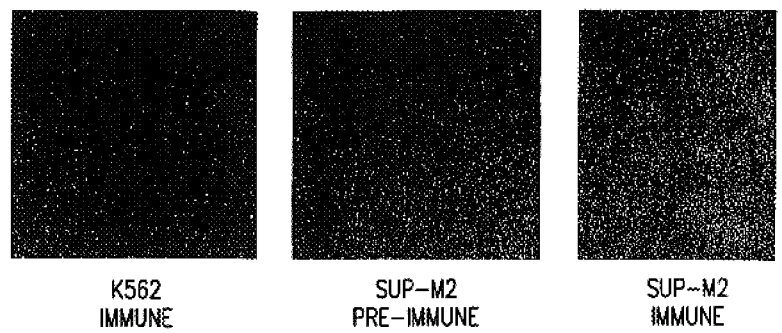

Immunofluorescent studies of NPM/ALK localization in the SUP-M2 lymphoma cell line performed with the IgG fraction of anti-ALK antiserum revealed intense cytoplasmic and nuclear staining with sparing of the nucleoli (FIG. 10(B)). Control experiments using pre-immune IgG with SUP-M2 or anti-ALK IgG with the t(2;5)-negative cell line K562 showed only background staining.

B. Association of NPM and NPM/ALK Proteins

The partial localization of NPM/ALK within the nucleus was unexpected, given that the NPM nuclear localization motifs are not retained in the fusion product. NPM has been shown to homo-oligomerize in the cell, associated in a head-to-head/tail-to-tail fashion as a hexamer. Thus, it is possible that NPM/ALK could physically associate with wild-type NPM via an N-terminal oligomerization motif and be shuttled into the nucleus as a result (M. S. Schmidt-Zachmann et al., *EMBO J.* 6:1881–1890 (1987); R.A. Borer et al., *Cell* 56:379–390 (1989); B. Y. Yung et al., *Biochim. Biophys. Acta.* 925:74–82 (1989); P. K. Chan, *Cancer. Res.* 49:3271–3275 (1989)).

To determine if NPM/ALK and wild-type NPM do in fact physically interact within the cell, co-immunoprecipitation experiments using anti-ALK and anti-NPM antibodies were performed (FIG. 11) essentially according to E.

Harlow et al., Chapter 11 in *Antibodies: A Laboratory Manual,* Cold Spring Harbor Laboratory, Cold Spring harbor, N.Y. (1988), p. 443. Proteins were resolved by 7.5% SDS-PAGE under reducing conditions, then immunoblotted with an anti-NPM polyclonal antibody prepared using the recombinant full-length protein as an immunogen (anti-NPM antibodies were a gift of Dr. P. K. Chan, Baylor University School of Medicine, Houston, Tex.).

Figure 11:
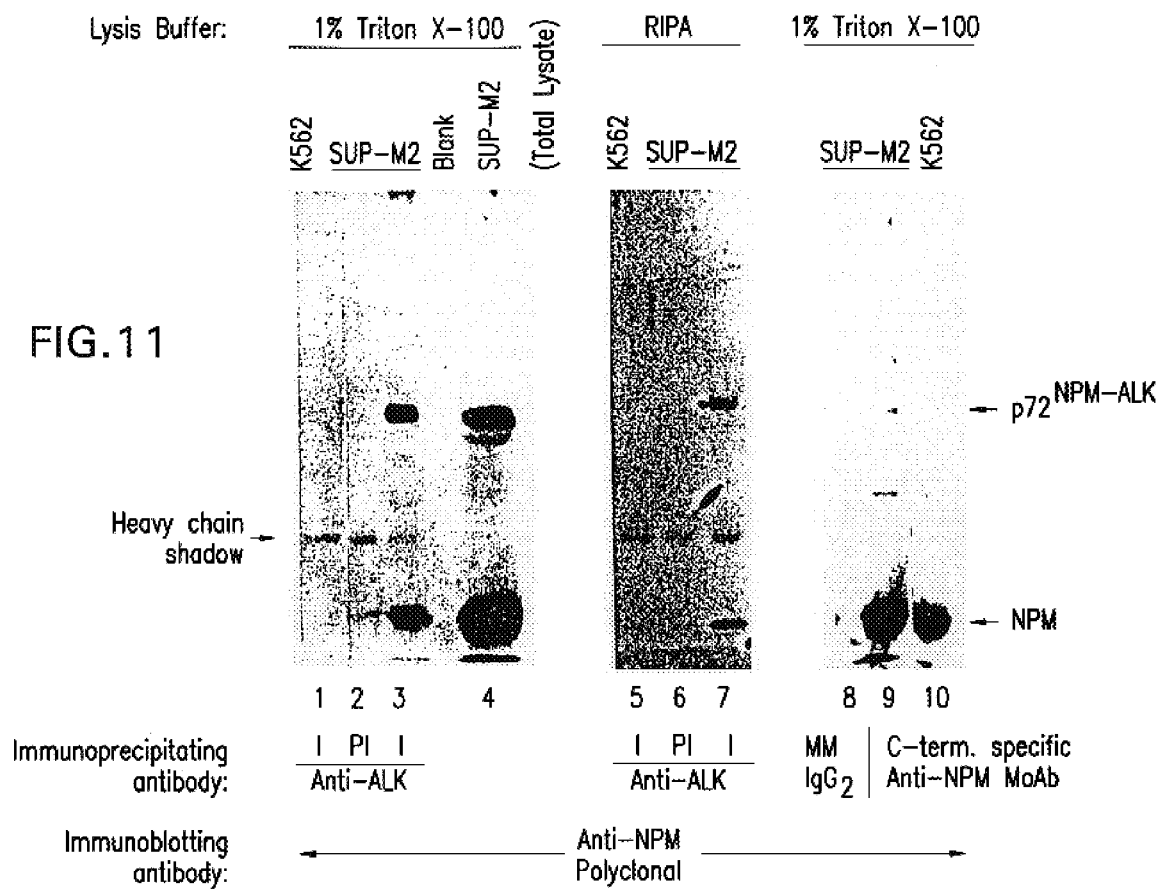
FIG. 11: NPM/ALK is physically associated with wild-type NPM in t(2;5)-positive lymphoma cells. Proteins were resolved by 7.5% SDS-PAGE under reducing conditions, then immunoblotted with an anti-NPM polyclonal antibody prepared using the recombinant full-length protein as an immunogen. The immunoprecipitating antibody used for lanes 9 and 10 is an anti-NPM monoclonal prepared with a C-terminal NPM peptide composed of residues that are not present in NPM/ALK. Purified mouse myeloma IgG$_2$ (MM IgG$_2$) served as an isotype-matched negative control (lane 8). Anti-NPM antibodies were a gift of Dr. P. K. Chan (Baylor University School of Medicine, Houston, Tex.).

In anti-ALK immunoprecipitations, co-precipitation of wild-type NPM was readily demonstrated in 1% Triton X-100 detergent lysates (FIG. 11, lane 3) and under more stringent detergent conditions using RIPA buffer lysates (FIG. 11, lane 7). Because RIPA buffer contains SDS, sodium deoxycholate and, in addition, Triton X-100, NP-40, or a similar mild detergent (E. Harlow et al., Chapter 11 in *Antibodies: A Laboratory Manual,* Cold Spring Harbor Laboratory, Cold Spring harbor, N.Y. (1988), p. 447), proteins that remain complexed under these conditions are tightly associated.

The association of NPM/ALK with NPM occurred with high stoichiometry, approaching a 1:1 ratio, suggesting that most of the cellular NPM/ALK is bound to NPM. Although only a small fraction of the very abundant NPM protein is complexed with NPM/ALK, their co-immunoprecipitation using a C-terminal epitope-specific NPM monoclonal antibody was easily demonstrated (FIG. 11, lane 9).

C. NPM/ALK and ALK Encode Proteins Having Tyrosine Kinase Activity

Tyrosine Kinase Activity of NPM/ALK and ALK Proteins

To determine whether the ALK portion of the NPM/ALK gene encodes a tyrosine kinase, in vitro kinase assays (J. B. Konopka et al., *Mol. Cell. Biol.* 5:3116–3123 (1985)) of anti-ALK precipitates from detergent lysates of the three t(2;5)-containing lines UCONN-L2, SU-DHL-1, and SUP-M2 were performed as follows. Cells were lysed in NP-40 lysis buffer (1% NP-40, 150 mM NaCl, 25 mM Tris, pH 7.4) containing protease inhibitors and $Na_3VO_4$ in concentrations identical to those noted above (Example 2(C)). Immunocomplexes were washed three times in this buffer and twice in kinase buffer (25 mM Hepes, pH 7.4, 12.5 mM $MnCl_2$, 6.5 mM $MgCl_2$) prior to resuspension in 10 μl kinase buffer containing 20 μCi of [γ-$^{32}$P]ATP (6000 Ci/mM, NEN) and 0.1 mM $Na_3VO_4$. Reactions were performed at 37° C. for 30 minutes, and stopped by boiling in the presence of 10 μl of 2× Laemmli's sample buffer, prior to SDS-PAGE on 7.5% polyacrylamide gels. Phosphoamino acid analysis of in vitro [γ-$^{32}$P] ATP-labeled NPM/ALK was carried out as previously described by Shih et al. (*J. Biol. Chem.* 257:11767–11773 (1982)). Briefly, labeled ALK protein was eluted from the gel, extensively digested with TPCK-trypsin, and hydrolyzed in 6 N HCl for 1 hour at 100° C. Following lyophilization, phosphoamino acids were resolved by thin-layer electrophoresis in two dimensions (pH 1.9 followed by pH 3.5).

Figure 12C:
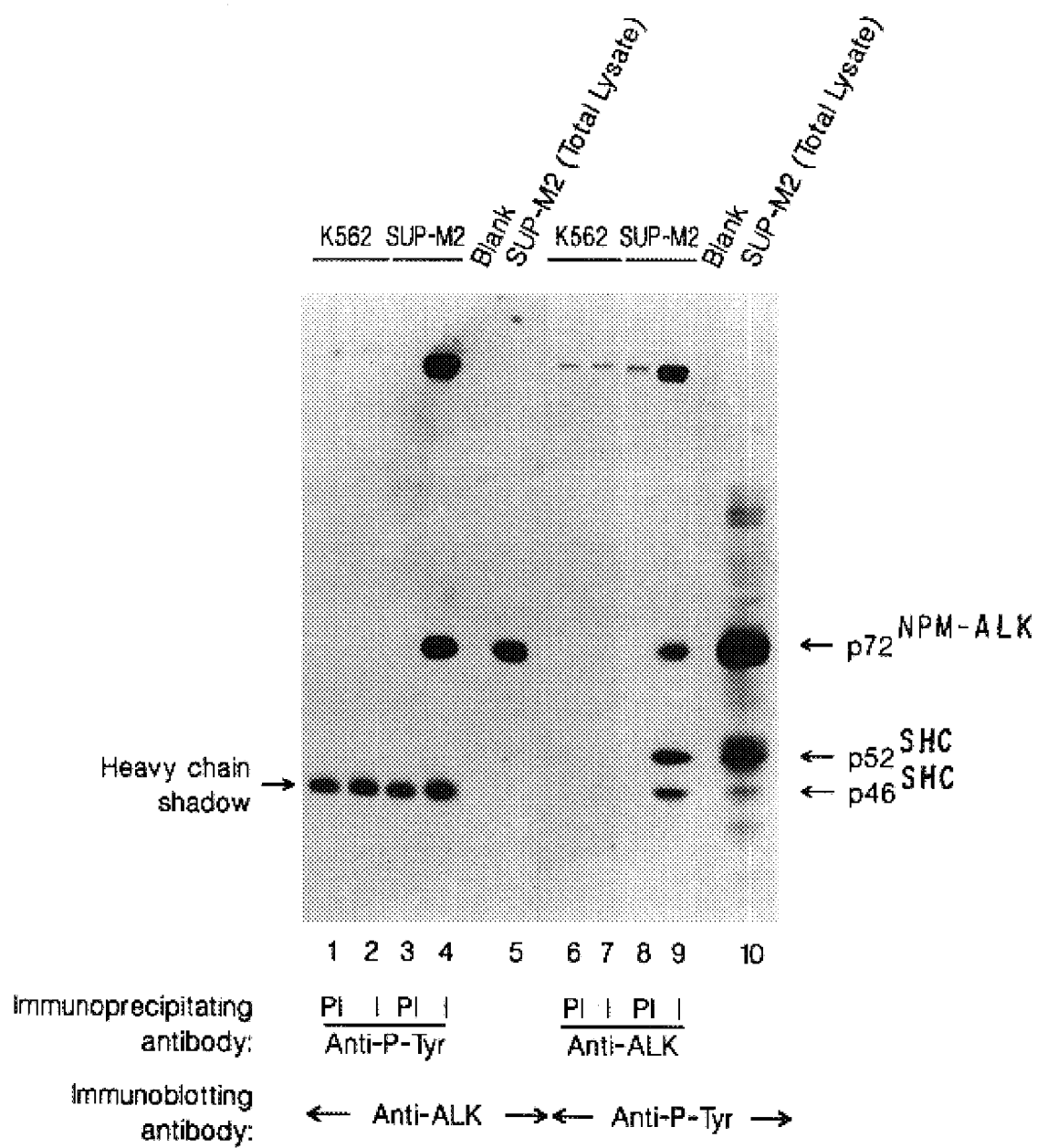

The 72 kDa NPM/ALK protein from the immunoprecipitates exhibited strong autokinase activity (FIG. 12(A)). This NPM/ALK autophosphorylation was resistant to alkali treatment, suggesting that the observed phosphorylation was present, at least in part, on tyrosine residues. This finding was confirmed by phosphoamino acid analysis of the NPM/ALK protein that showed in vitro phosphate incorporation restricted to tyrosine (FIG. 12(B)). Constitutive activation of NPM/ALK in t(2;5) lymphoma cells was demonstrated in immunoprecipitation/immunoblotting experiments using anti-ALK and anti-phosphotyrosine sera (FIG. 12(C)).

Figures 13A, 13B:
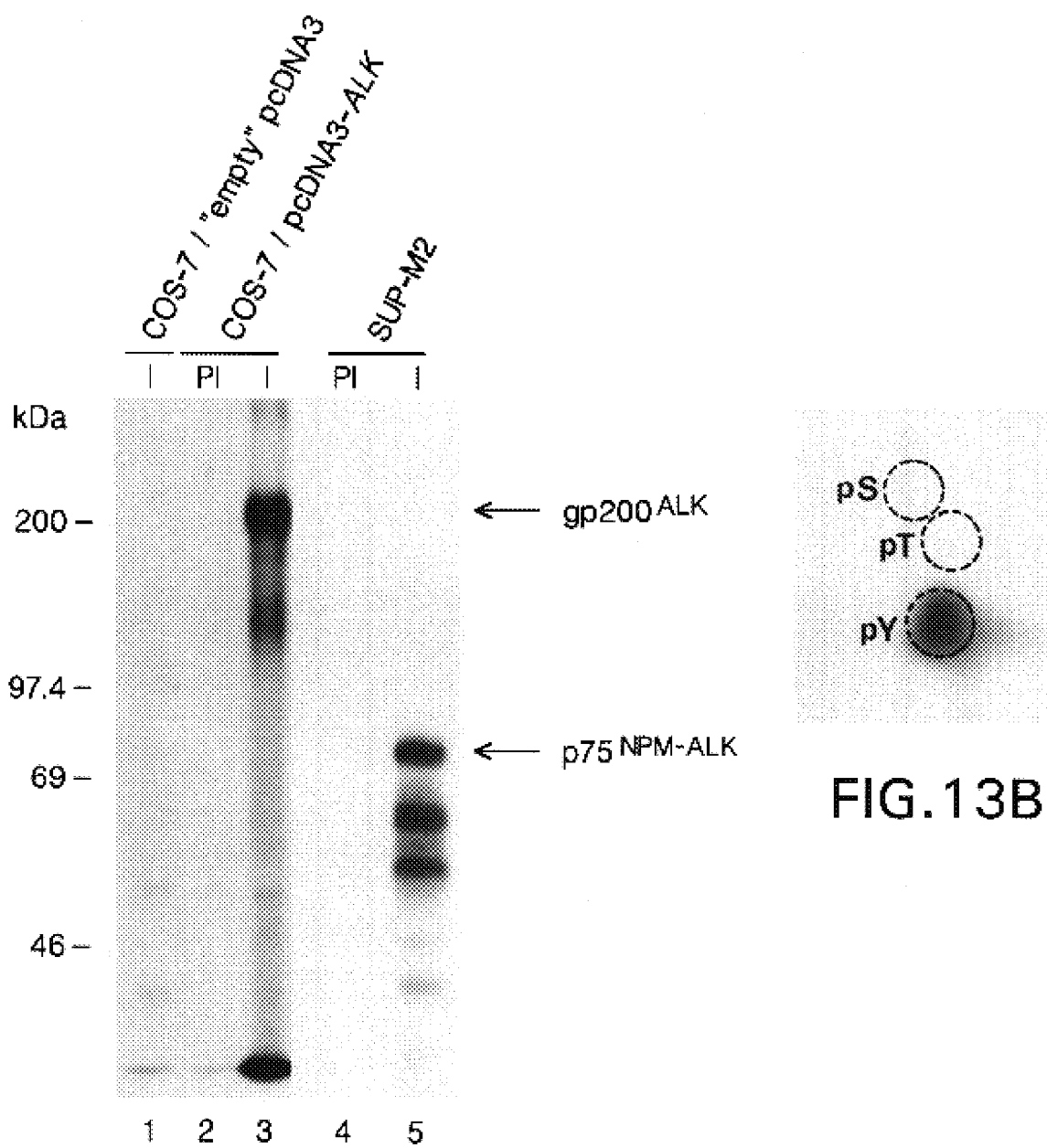
FIGS. 13A–13B ALK encodes a protein having tyrosine kinase activity. (A) Kinase activity in immunoprecipitates obtained by incubating lysates from COS-7 cells electroporated with either pcDNA3 vector alone (lane 1) or pcDNA3-ALK (lanes 2 and 3), or the t(2;5)-positive lymphoma cell line SUP-M2 that expresses NPM-ALK (lanes 4 and 5) with preimmune (PI) or immune (I) anti-ALK serum. Immunocomplexes were incubated with [γ-$^{32P}$P]ATP and analyzed by 7.5% polyacrylamide SDS-PAGE performed under reducing conditions as described in Material and Methods. A one minute autoradiographic exposure performed at room temperature is shown. The identity of the two phosphorylated proteins with faster mobility relative to p$_{75}$NPM-ALK are unknown but they may represent NPM-ALK proteolytic degradation fragments and/or proteins that are known to be associated with, and phosphorylated by, NPM-ALK such as SHC (S. W. Morris, unpublished data). (B) In vitro phosphorylated gp200$^{ALK}$ was cut from the polyacrylamide gel and eluted, and its phosphoamino acid composition determined by two-dimensional thin-layer electrophoresis. Abbreviations: pS, phosphoserine; pT, phosphothreonine; pY, phosphotyrosine.

Activation of the catalytic kinase function of RTKs is typically induced by ligand-mediated dimerization of the receptors, resulting in intermolecular cross-phosphorylation (Ullrich and Schlessinger, Cell 61:203–212 (1990)). This process can be mimicked by receptor-specific antibody, as has been demonstrated in in vitro immunocomplex kinase assays for a number of RTKs. To assess whether the ALK protein is a functional kinase, recombinant gp200$^{ALK}$ (Example 2(C)) immunoprecipitated from COS-7 cells was incubated with [$\gamma$-$^{32}$P]ATP in the presence of Mn and Mg ions. As shown in FIG. 13(A), ALK is efficiently autophosphorylated in the in vitro kinase conditions used. Assays using endogenous ALK protein immunoprecipitated from Rh30 cells produced similar results (data not shown). Phosphoamino acid analysis demonstrated that the in vitro autophosphorylation of ALK was restricted to tyrosine residues (FIG. 13(B)).

Association of NPM/ALK Protein with PTK Substrates

To determine if NPM/ALK may function at least partly via known PTK cytoplasmic substrates, the ability of the fusion protein to physically engage three well-characterized SH2 and SH3 domain-containing PTK substrates (phosphatidylinositol 3-kinase (PI3-K), phospholipase-C$\gamma$ (PLC-$\gamma$), and the Src homologous and collagen (SHC) protein was determined. PI3-K (composed of an 85 kDa adaptor protein and a 110 kDa catalytic subunit) is a lipid kinase that phosphorylates the D3 position of phosphatidylinositol (Parker & Waterfield, Cell Growth Differ. 3:747–752 (1992)). Changes in PI3-K activity correlate with cell proliferation but the downstream effectors involved in its signaling remain unclear, although recent evidence suggests that PI3-K may mediate PTK-induced phosphorylation of the ribosomal protein S6 via the 70 kDa S6 kinase (Chung, J. et al., Nature 370:71–75 (1994)). PLC-$\gamma$ is a 148 kDa phosphodiesterase that hydrolyzes phosphatidylinositol-4,5-bisphosphate to inositol trisphosphate and diacylglycerol--second messengers that increase intracellular calcium and activate the serine/threonine-specific protein kinase C, respectively (Nishizuka, Y., Science 258:607–614 (1992)). SHC, expressed as two proteins of 46 and 52 kDa, has been shown to associate with activated PTKs and to complex with growth factor receptor-bound substrate-2 (GRB2) and the guanine nucleotide exchange factor mSOS1, resulting in RAS pathway activation (Rozakis-Adcock, M. et al., Nature 360:689–692 (1992)).

Although these substrates represent only three of the multiple PTK substrates now identified, these proteins are thought to be intermediates in distinct PTK mitogenic signaling pathways. Demonstration of their association with NPM/ALK, suggesting activation of their pathway(s), provides at least a partial insight into how the constitutively activated fusion protein might transform cells.

Figure 14A:
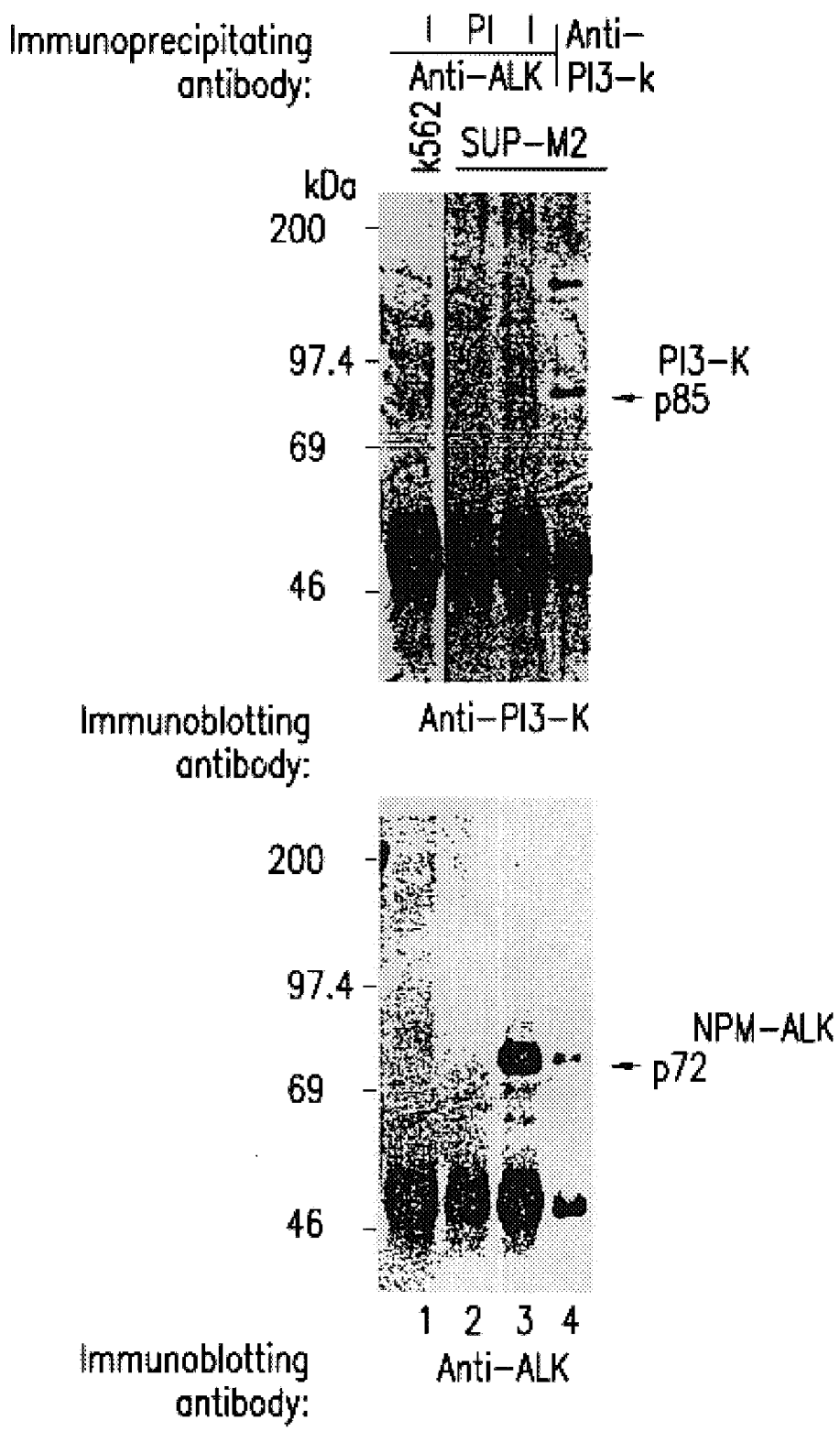
FIGS. 14A–14C NPM/ALK associates with cytoplasmic PTK substrates in t(2;5)-positive lymphoma cells. Cell lysates were incubated with the indicated antibodies for immunoprecipitation, resolved by 6.5% SDS-PAGE, then immunoblotted using antibodies directed against (A) the 85 kDa subunit of PI3-K, (B) phospholipase-Cγ (PLC-γ), or (C) SHC (top panels). The membranes were then stripped and hybridized with ALK-specific antibody (bottom panels). Total cell lysates of Epidermal Growth Factor (EGF)-stimulated A43 1 human epidermoid carcinoma cells (PLC γ blot) and SUP-M2 (SHC blot) served as positive controls. While the interaction of SHC with NPM/ALK protein immunoprecipitated using anti-ALK was readily demonstrated (lane 12), this association was not apparent with the anti-SHC polyclonal antibody (lane 13), which is directed against epitopes in the SHC SH2 domain that are probably masked in SHC molecules bound to NPM/ALK.
Figure 14B:
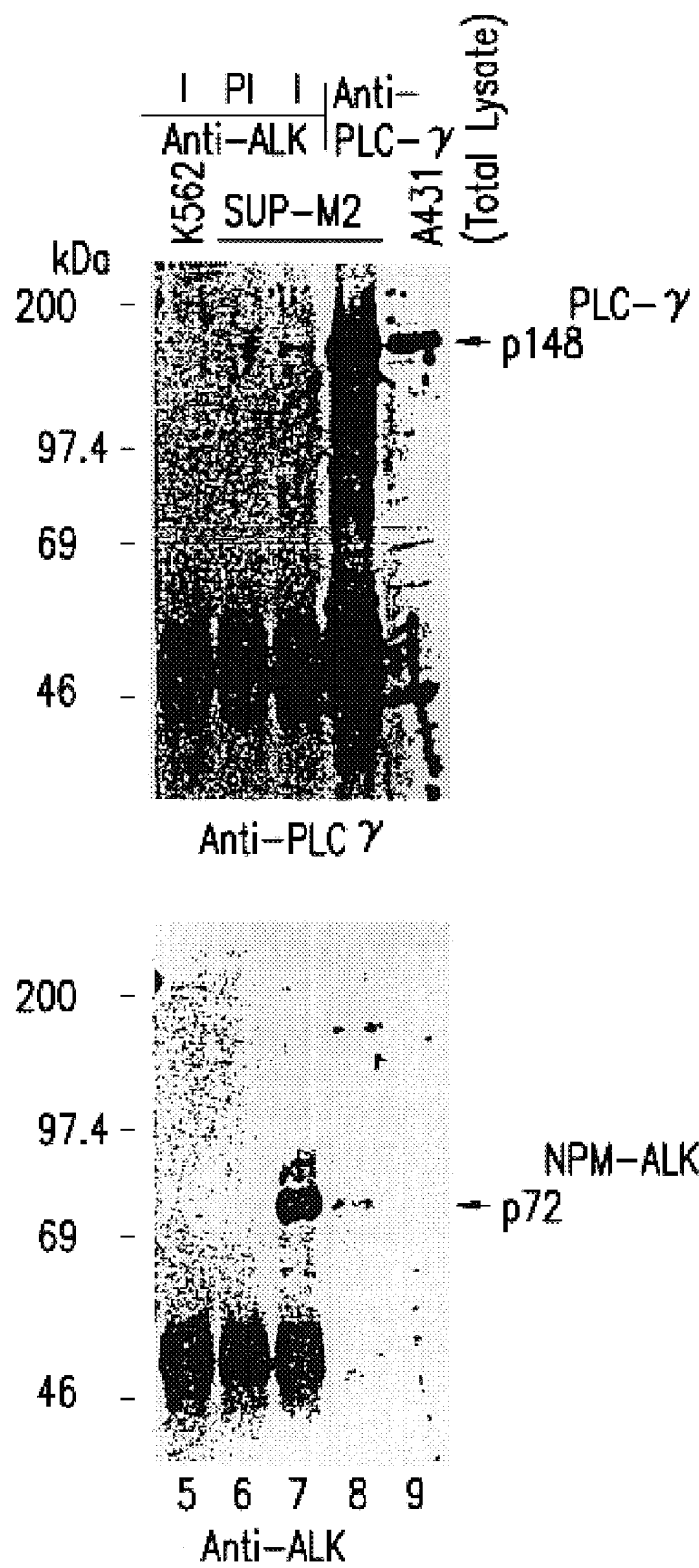
Figure 14C:
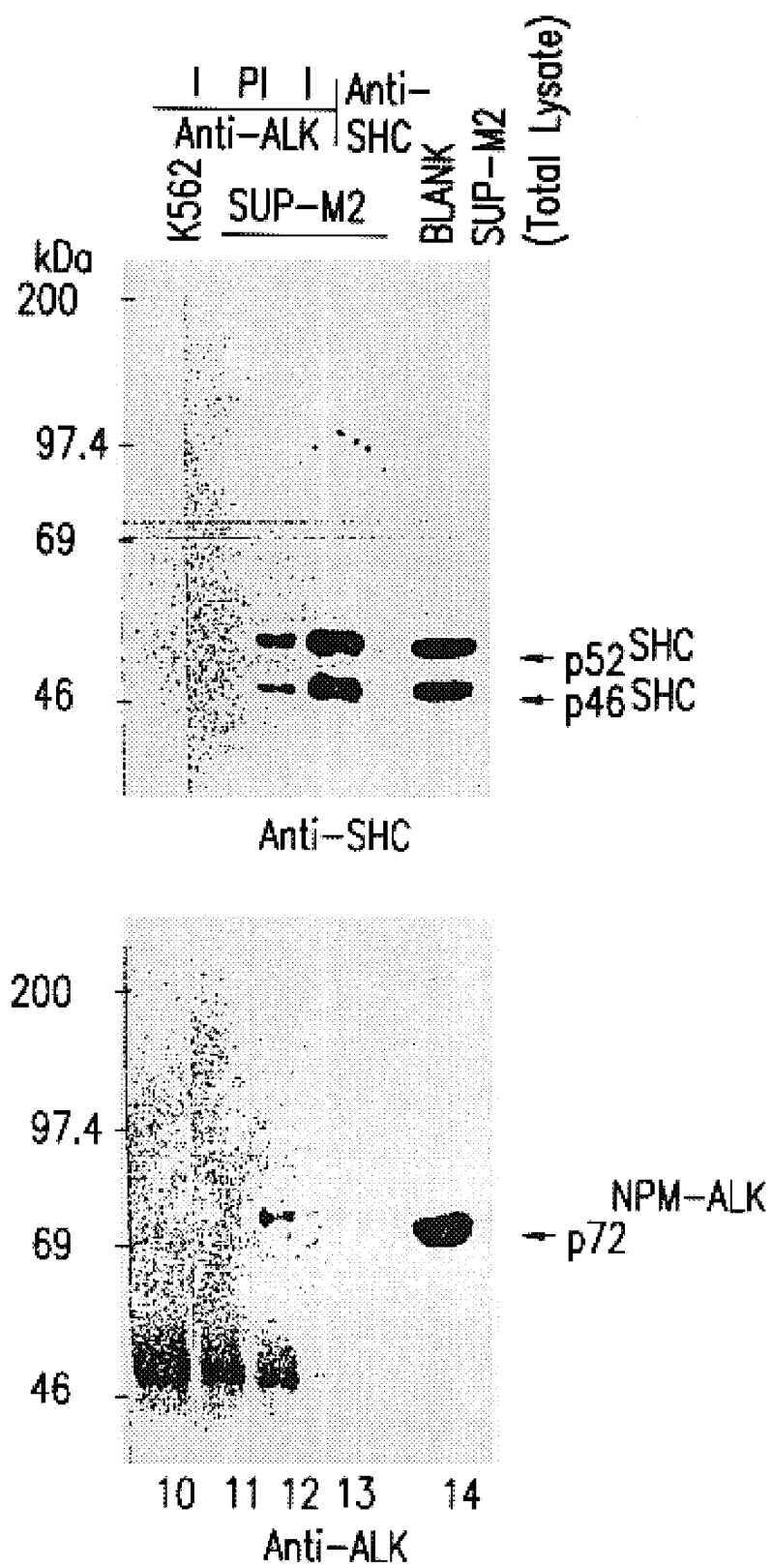

Association of these substrates with NPM/ALK was readily demonstrable in anti-ALK immunoprecipitates from 1% Triton X-100 lysates of the t(2;5)-positive line SUP-M2 (FIG. 14(A)–(C)). The percentage of the total cellular amount of these substrates bound to NPM/ALK ($\sim$1% of the p85PI3-K or PLC$\gamma$ pools; $\sim$10% of intracellular SHC) parallels that observed with other PTKs; likewise, the NPM/ALK bound to each substrate (<5% of the total cell pool) is similar to the amount of other PTKs bound to these substrates (Soler, C. et al., J. Biol. Chem. 269:12320–12324 (1994)). In other experiments, the portion of each of these proteins that co-precipitated with NPM/ALK was found to contain phosphorylated tyrosine residues (e.g., see FIG. 12(C) for data regarding SHC).

Although it is possible that NPM/ALK biologic activity may be explained solely by signaling mediated via these three (and possibly other yet-to-be defined) cytoplasmic pathways, the finding that NPM/ALK is localized within both the cytoplasm and nucleus of t(2;5)-positive lymphoma cells suggests that it may generate growth regulatory signals within both cellular compartments. Because the prototypical PTKs are localized at or span the plasma membrane, PTK-mediated signaling has classically been thought of as occurring only via cytoplasmic substrates. However, recent experimental data support a role for nuclear PTKs and PTK substrates in RNA processing and trafficking, transcriptional control of gene expression, and possibly other nuclear processes; in addition, several "cytoplasmic" PTKs including SRC, FER, and FGR are now known to localize in part to the nucleus in some cells or under certain conditions (reviewed in Wang, J. Y., Trends. Biochem. Sci. 19:373–376 (1994)).

D. Biological Activity of NPM/ALK Proteins

NPM/ALK Renders IL-3-Dependent Cell Lines Factor-Independent

A full-length NPM/ALK cDNA restriction fragment (5' NotI/3' EcoRV) was cloned into the mammalian expression vector pcDNA3 (Invitrogen, San Diego, Calif.) that had been restricted initially with XbaI, filled in with Klenow fragment, and finally restricted with NotI. In the resulting vector construct, pcDNA3-NPM/ALK, NPM/ALK is expressed from the cytomegalovirus (CMV) major intermediate early promoter/enhancer.

Figure 15:
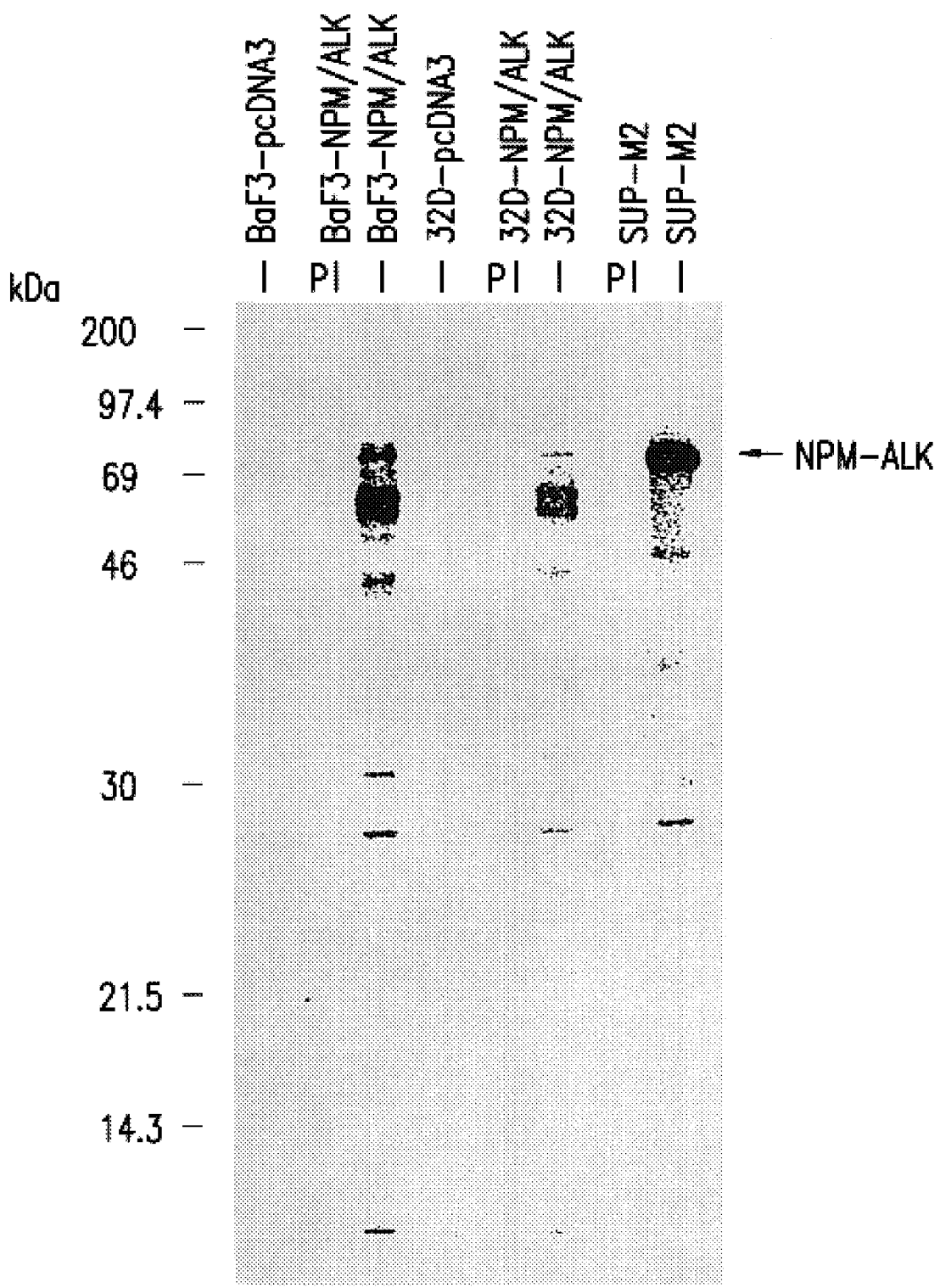
FIG. 15: Measurement of p72$^{NPM/ALK}$ kinase activity in factor-independent hematopoietic cells. An in vitro kinase assay was performed on anti-ALK immunoprecipitates from whole cell extracts of 3×10⁷ cells per sample from pooled populations of BaF3 and 32D electroporated with the "empty" pcDNA3 vector (BaF3-pcDNA3 and 32D-pcDNA3) grown in IL-3-containing medium with G418 and from factor-independent cells that had been electroporated with the pcDNA3-NPM/ALK construct (BaF3-NPM/ALK and 32D-NPM/ALK). The factor-independent cells were tested 4 weeks following withdrawal of IL-3. The t(2;5)-positive lymphoma line SUP-M2 (3×10⁷ cells per sample) was included as a positive control. The autoradiograph shown is of a 12.5% SDS-PAGE that was exposed to film for 5 minutes at room temperature with an intensifying screen. PI-pre-immune serum; I-anti-ALK serum.
Figure 16B:
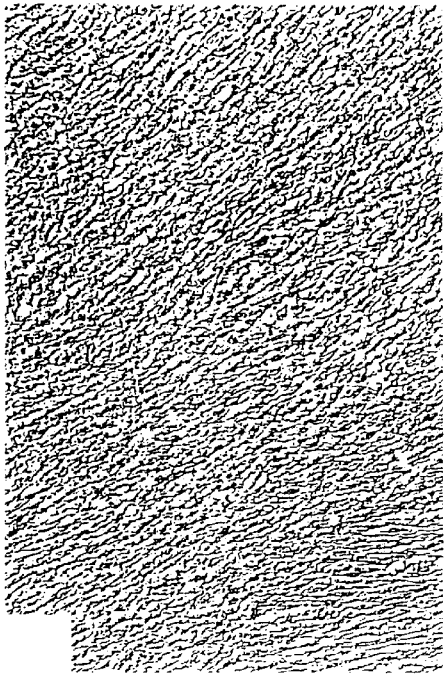
FIGS. 16A–16D Morphologic alterations induced by expression of $p_{72}^{NPM/ALK}$ in Fischer rat 3T3 (Fr3T3) fibroblasts. Photomicrographs of fibroblasts infected with (A and B) pSRαMSVtkneo/NPM/WALK viral stock, or with (C) viral stock prepared using "empty" pSRαMSVtkneo. (D) Parental Fr3T3. Photographs were taken 2½ weeks post-infection. Magnification, x 10.
Figure 16D:
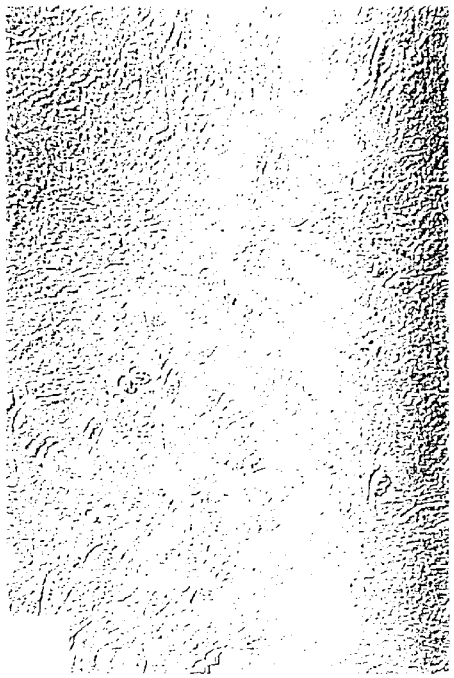
Figure 16A:
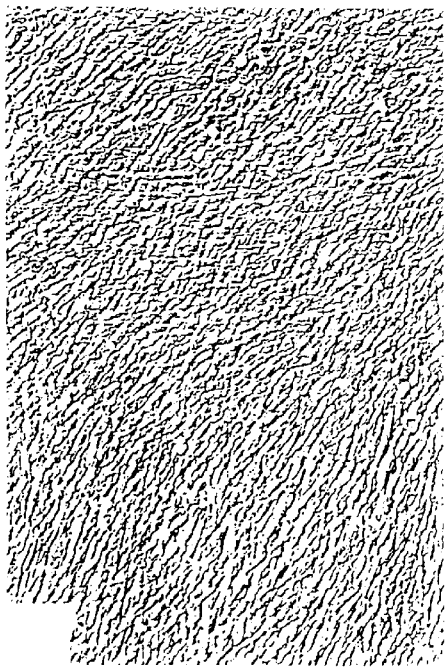
Figure 16C:
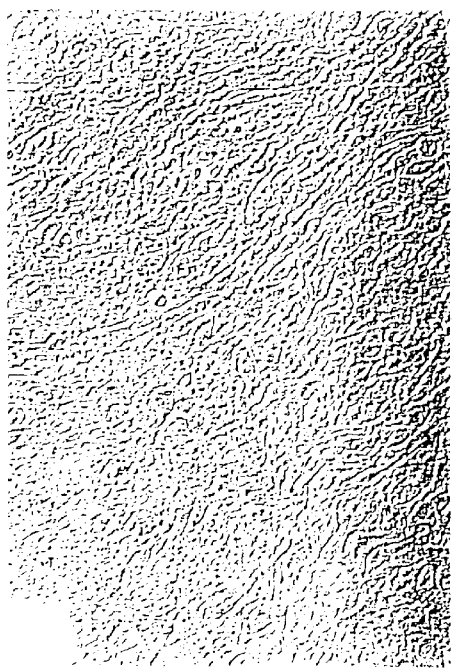
Figure 17A:
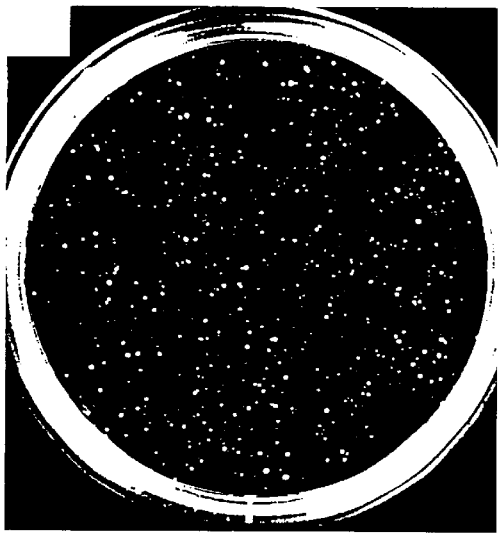
FIG. 17 (Panels A–D): Anchorage-independent growth of Fr3T3 due to expression of NPM/ALK. Equivalent numbers of cells (5×10³) were seeded in soft agar 2 days following infection with viral stock produced using (A) pSRαMSVtkneo/NPM/ALK, (B) "empty" pSRαMSVtkneo, or (D) the retroviral construct pSM-FeSV which expresses the highly transforming McDonough strain of v-fms. (C) Uninfected parental Fr3T3. The soft agar colonies were photographed 2 weeks after plating. Results are representative of three independent experiments.
Figure 17B:
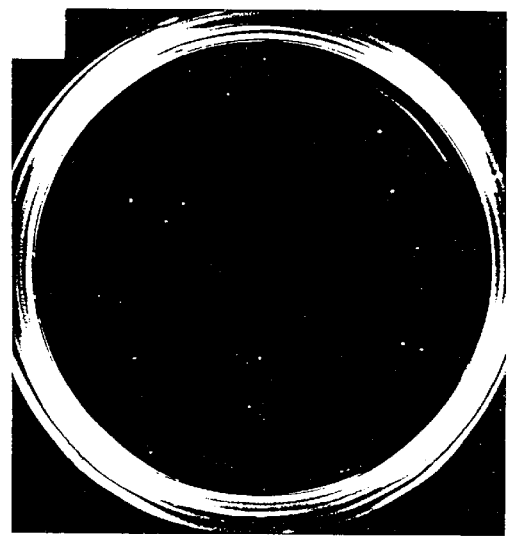
Figure 17C:
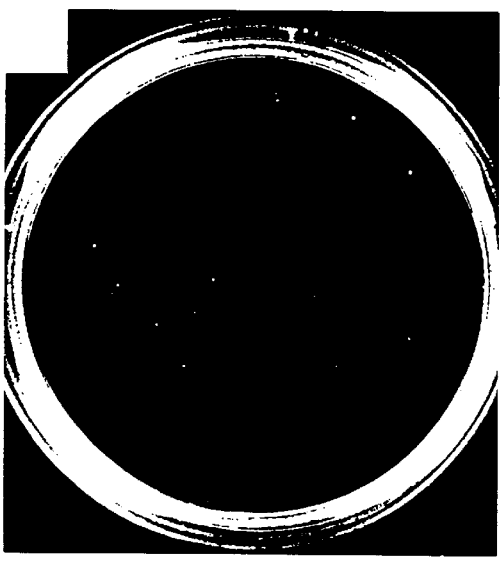
Figure 17D:
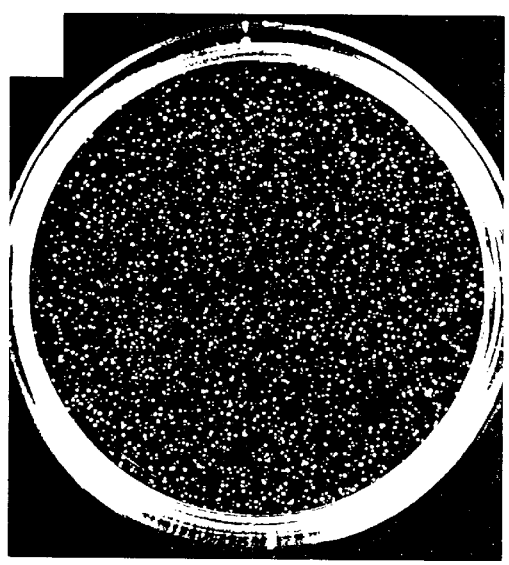

In initial experiments to determine the biological activity of NPM/ALK, expression of the fusion protein was found to render the IL-3-dependent myeloid cell line 32D, as well as the pro-B lymphoid line BaF3, factor-independent. Both of these cell lines are normally strictly dependent on IL-3 for proliferation and survival and are non-tumorigenic in nude mice. With both of these cell lines, multiple factor-independent clones emerged within 3 weeks of growth in IL-3 under G418 selection following the introduction of pcDNA3-NPM/ALK by electroporation. These factor-independent clones continue to grow in the absence of IL-3 for more than 2 months. Although electroporation of "empty" pcDNA3 into these lines produced comparable numbers of G418-resistant clones, none were IL-3-independent, suggesting that the spontaneous development of factor-independence of the cells used in these studies is rare. Furthermore, the observation that all individual G418-resistant clones from the two lines (14 for 32D; 21 for BaF3) that had been electroporated with the NPM/ALK construct grow in the absence of IL-3 suggests that it is unlikely that cooperating mutations are needed for the development of factor-independence. The expression of functional NPM/ALK protein in a mixed population of IL-3-independent cells derived from each parenteral cell line was confirmed, as judged by the ability of the protein to autophosphorylate in in vitro kinase assays (J. B. Konopka et al., Mol. Cell. Biol. 5:3116–3123 (1985); FIG. 15).

The demonstration that NPM/ALK expression induces IL-3-independent proliferation of 32D and BaF3 indicates that the NPM/ALK cDNA clone encodes a functional protein and provides an easily reproducible biological assay system with which to assess the biological effects of the NPM/ALK mutants. In addition, the ability of NPM/ALK to induce factor-independence of 32D cells, which lack both insulin receptor substrate-1 (IRS-1) and the IRS-1-like substrate 4PS (IL-4-induced phosphotyrosine substrate) (Wang, L. et al., *Science* 261:1591–1592 (1993)), indicates that NPM/ALK signaling does not involve these cytoplasmic substrates. Because the normal ALK cDNA clone pRMS17-2 contains a sequence identical to the portion of the ALK receptor present in the NPM/ALK fusion protein, normal ALK protein is expected to have similar biological effects.

Retroviral Expression of NPM/ALK and Cellular Transformation

To demonstrate the effect of in vivo expression of the NPM/ALK fusion protein on fibroblast cells, a "wildtype" NPM/ALK retroviral construct derived from the expression vector pSRαMSVtkneo was prepared as follows. Oligonucleotides having the HindIII restriction sequence (5'-AAGCTT) were ligated onto a blunt-ended restriction fragment containing the full NPM/ALK gene. This NPM/ALK-containing restriction fragment was then treated with HindIII restriction enzyme and cloned into the unique HindIII site in pSRαMSVtkneo. This expression vector drives transcription of inserted cDNAs from the Moloney leukemia virus LTR (A. J. Muller et al., *Mol. Cell. Biol.* 11:1785–1792 (1991)). Helper-free retroviral stocks, prepared by co-transfection of 293T human embryonic kidney cells with pSRαMSVtkneo/NPM/ALK and a Ψ2 packaging plasmid, were used to infect rodent fibroblasts essentially as described by C. Cepko, "Transduction of Genes Using Retrovirus Vectors" in Chapter 9, *Current Protocols in Molecular Biology*, F. M. Ausubel et al., eds., John Wiley & Sons, Boston, Mass. (1994), pp. 9.10.1–9.14.3. Retroviral stocks prepared using "empty" pSRαMSVtkneo and the construct pSM-FeSV (which expresses the McDonough strain of the feline sarcoma virus oncogene v-fms), served as negative and positive transformation controls, respectively (A. Hampe et al., *Proc. Natl Acad. Sci. (USA)* 81:85–89 (1984); J. M. Heard et al., *Cell* 51:663–673 (1987)).

Fibroblast infections were performed using equalized numbers of infectious virus for each of these three viral stocks. Forty-eight hours post-infection the cells were plated in tissue culture dishes containing Dulbecco's modified Eagle's media (DMEM) with 10% fetal calf serum and observed for a 2½-week period. In addition, equivalent numbers of cells infected with each viral stock were seeded per 60 mm culture dish in soft agar. Whereas Fischer rat 3T3 fibroblasts (Fr3T3) infected with viral stock prepared using "empty" pSRαMSVtkneo grew as a contact-inhibited monolayer identical to parental cells, the cells infected with NPM/ALK retroviral stock formed multiple foci of densely packed, morphologically transformed cells that coalesced upon further growth to form confluent sheets of abnormal cells (FIG. 16).

Figure 19:
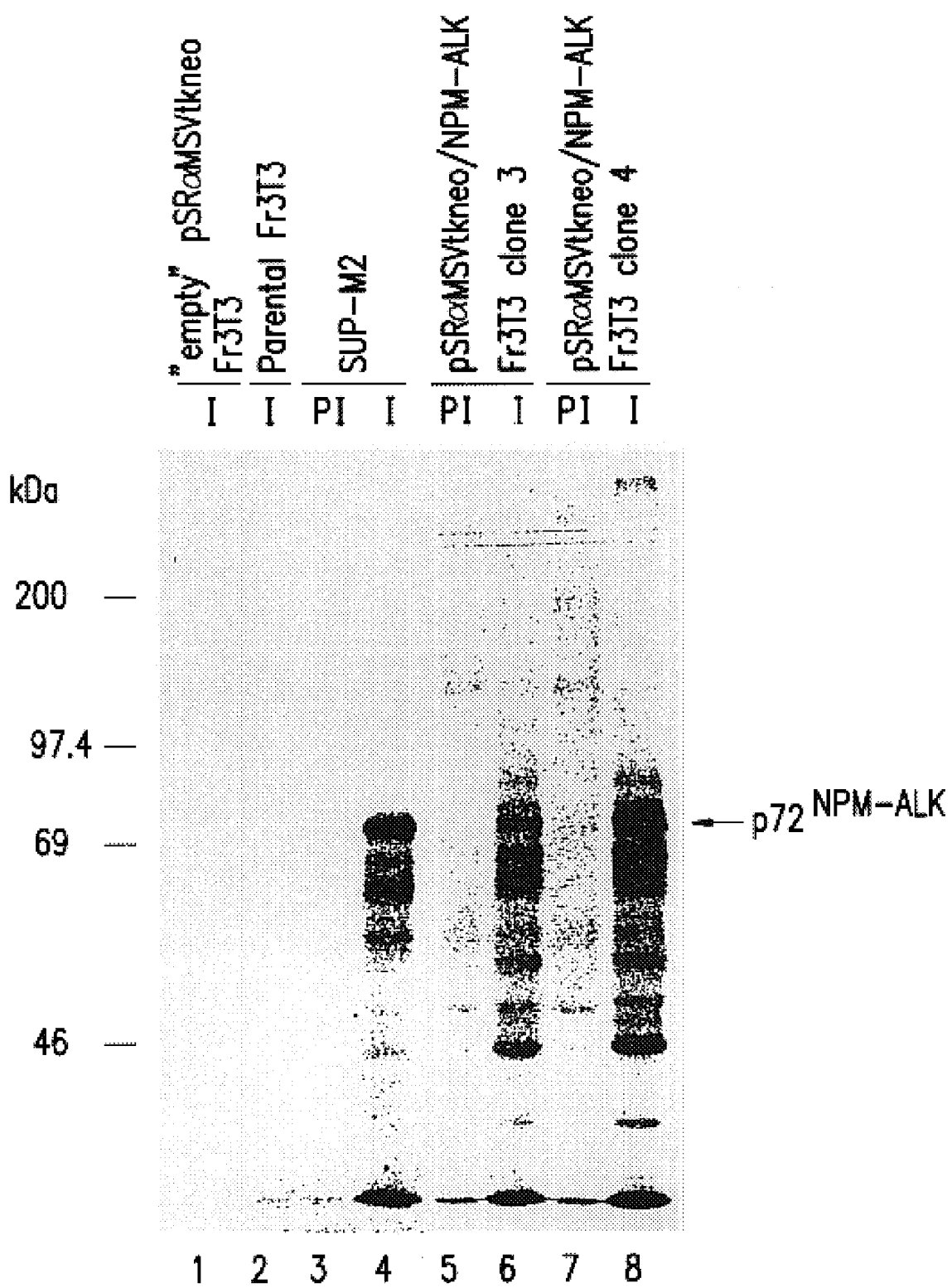
FIG. 19: NPM/ALK expression in cell lines established from individual soft agar colonies. In vitro kinase assays were performed on anti-ALK immunoprecipitates from detergent lysates of 2×10⁷ cells per sample. The proteins were resolved by 7.5% SDS-PAGE, then exposed to film for 3 minutes at room temperature. The analysis of two independent Fr3T3 clones infected with NPM/ALK viral stock is illustrated (lanes 5–8); the t(2;5)-positive lymphoma cell line SUP-M2 is included as a positive control (lanes 3 and 4). PI: pre-immune serum; I: anti-ALK serum.

Further evidence of NPM/ALK-induced transformation was noted in soft agar anchorage-independent growth assays. At two weeks, Fr3T3 infected with NPM/ALK viral stock formed numerous large colonies in agar culture; cells infected with virus prepared using the empty vector exhibited a low background of colony formation which was comparable to that of parental cells (FIGS. 17 and 18). Results similar to those observed with Fr3T3 were also seen with NIH-3T3; selection of G418-resistant Fr3T3 or NIH-3T3 cells prior to seeding in soft agar greatly enhanced the plating efficiency of the fibroblasts infected with NPM/ALK viral stock but not of cells infected with "empty" vector viral stock, as expected. NPM/ALK protein expression in infected cells was confirmed by performing an in vitro kinase assay using detergent lysates (J. B. Konopka et al., *Mol. Cell. Biol.* 5:3116–3123 (1985)) prepared from cell lines established from individual soft agar colonies (FIG. 19). These fibroblast transformation assays complement the assays which demonstrate the abrogation of IL-3 dependency of the BaF3 and 32D hematopoietic cell lines by the NPM/ALK fusion protein.

E. Identification and Isolation of Ligands for the ALK Receptor

The present invention also includes methods directed towards the identification and isolation of ligands for the ALK receptor.

Cultured Cells Expressing and Displaying ALK or ALK Fusion Proteins on Their Cell Surfaces Recent studies indicate that it is the amino acid sequence of a given receptor, rather than the cellular environment in which a receptor gene is expressed, processed, and displayed that determines the specific pharmacological properties thereof. Hartig, P. R., in *Medications Development: Drug Discovery, Databases, and Computer-Aided Drug Design*, NIDA Research Monograph 134, NIH Publication No. 93-3638, Rapaka, R. S., and Hawks, R. L., eds., U.S. Dept. of Health and Human Services, Rockville, Md. (1993), pages 58–65. Thus, the cloning of the gene encoding the ALK receptor, combined with the fact that ALK is displayed on cell surfaces as a single polypeptide chain (Example 2(C)), allows for the production of cultured cell lines that express and display ALK, or ALK-derived fusion proteins, on their cell surfaces.

Eukaryotic cells that have been genetically engineered to express and display ALK protein via the use of the ALK nucleic acids of the invention, using host cell lines which are devoid of related receptors, may be generated using, for example, the expression constructs described herein (Example 2(C)) and methods of genetic transformation known in the art (see, e.g., Chapters 9, 13 and 16 in Ausubel et al., *Current Protocols in Molecular Biology*, Wiley Press, Boston, Mass. (1993)).

Furthermore, although the NPM/ALK fusion protein is intracellularly localized, other ALK-derived fusion proteins incorporate polypeptide features that ensure the display of ALK amino acid sequences on the cell surface. ALK expression constructs can be produced which express a fusion protein composed of the extracellular domain of ALK linked to the constant domain of human immunoglobulin G1 (ALK-Fc) for use as a ligand probe (Armitage, R. J. et al., *Eur. J. Immunol.* 22:2071–2076 (1992); Fanslow, W. C., et al., *J. Immunol.* 149:655–660 (1992)). For example, an Asp7l8I-BstEII restriction fragment, which encodes the extracellular portion of ALK, is ligated with BstEII/BglII linkers to a Bg/II-NotI Fc-encoding fragment; the resultant Asp718I-NotI fragment is ligated into an appropriate Asp718I- and NotI-restricted mammalian expression vector which contains one or more eukaryotic origins of replication, and transfected into the monkey kidney cell line CV1 engineered to express the Epstein-Barr virus nuclear antigen-1 (CV1/EBNA cells). If desired, the ALK-Fc protein is purified from CV1/EBNA cell culture supernatants on a protein G-agarose column according to previously-described methods (McMahan, C. J., et al., *EMBO J.* 10:2821–2832 (1991)). Alternatively, murine or other mammalian cell lines (see, for example, Teitler, M., et al., *Molecular Pharmacology* 38:594–598 (1990)) or lower eukaryotic cells, such as yeast cells, are used to express and display the ALK receptor.

Furthermore, receptors such as ALK that function as single polypeptide chains may be easily fused to bacterial proteins that are displayed either on the inner or outer bacterial membranes with retention of the receptor's ligand-binding activity and pharamacological specificity (Marullo, S., et al., *Proc. Natl. Acad. Sci. (USA)* 85:7551–7555 (1988); Chapot, M.-P., et al., *Eur. J. Immunol.* 187:137–144 (1990)). ALK fusions expressed in bacterial cells will not be glycosylated (Example 2(C)) and thus allow for the identification of ligands that bind more efficiently to the unglycosylated form of the ALK receptor.

Screening Expression Libraries for ALK Ligands

Cells that potentially express a surface form of ALK ligand are screened for ALK-Fc binding using flow cytometry or tissue staining (Armitage, R. J. et al., *Eur. J. Immunol.* 22:2071–2076 (1992)). Further, ALK ligand-producing cell lines or tissues may be identified by in situ hybridization analysis of ALK expression (H. M. Cooper et al., in *Current Protocols in Molecular Biology*, F. M. Ausubel et al., eds., John Wiley & Sons, Boston, Mass. (1994), pp. 11.4.1–11.4.5)). Based on the results presented in previous studies of other receptor tyrosine kinases and their ligands (e.g., Ferracini et al., *Oncogene* 10:739–749 (1995)), it is believed that some transformed cell lines derived from the same tissues that normally express ALK will express ALK ligand in an autocrine fashion. Accordingly, a large number of rhabdomyosarcoma lines established at St. Jude Children's Research Hospital, demonstrated to express ALK by Northern and Western analysis, are screened by flow cytometry or tissue staining using ALK-Fc proteins to confrim expression of an ALK ligand. Identification of an ALK ligand-expressing cell line in this manner may require the screening of several cell lines; for example, nearly 100 murine and human lines were screened to identify an FLT3 ligand (Lyman, S. D. et al., *Cell* 75:1157–1167 (1993)).

Test cell lines for flow cytometric analysis are incubated with ALK-Fc or control fusion proteins constructed with the extracellular domains of other PTKs, then stained with biotinylated antibody specific for the Fc domain of human IgG followed by streptavidin-phycoerythrin (Armitage, R. J. et al., *Eur. J. Immunol.* 22:2071–2076 (1992)). RNA from the line exhibiting the highest ALK-Fc specific binding can be used to prepare an expression library in pDC409 (Lyman, S. D. et al., *Cell* 75:1157–1167 (1993)) or another comparable expression vector. A slide-based autoradiographic screening technique, which is more sensitive than classical screening methods using contact radiography for detecting weakly positive cells, can be used to identify ALK ligand cDNA clones (McMahan, C. J. et al., *EMBO J.* 10:2821–2832 (1991)). In this procedure, CV1/EBNA cells grown on microscope slides are transfected with pools of ~1000 expression library clones. Three days post-transfection the cells are incubated with unlabeled ALK-Fc, and specifically bound cells are detected by incubation with $^{125}$I-labeled mouse antibody specific for human IgG1 Fc domain. Positive cells with overlying silver grains are visualized by light microscopy after the slides have been coated with photographic emulsion and in situ autoradiography performed. Positive cDNA pools are progressively reduced into subpools that are screened in similar fashion until an ALK ligand-expressing clone is purified.

Secreted Forms of ALK Ligand(s)

Assays are performed to identify sources of ALK ligand which exist mainly in a secreted form. A cell line dependent on ALK ligand for growth is prepared for proliferation assays. The full-length ALK cDNA is electroporated into the IL-3-dependent murine hematopoietic line BaF3 for this purpose. Because expression of the constitutively activated NPM/ALK protein in these cells renders them IL-3-independent (Example3(D)), the normal ALK receptor should generate a proliferative signal in BaF3 cells exposed to the ALK ligand.

A related approach is to prepare a chimeric receptor composed of the extracellular domain of ALK fused to the transmembrane and cytoplasmic domains of another receptor PTK known to generate proliferative signals within BaF3 cells (e.g., KIT) (Williams, D. E. et al., *Cell* 63:167–1741 (1990)). A test line containing such a chimeric receptor can then be used to screen conditioned media prepared from a variety of cultured cell lines to identify a line that supports proliferation of ALK ligand-dependent cells. This screening is performed by, for example, conventional tritiated thymidine incorporation assays of the ALK ligand-dependent BaF3 incubated with the conditioned media in microtiter plates. Media containing ALK ligand mitogenic activity are tested at various dilutions to establish a dose-dependent proliferation effect. In addition, control assays with parental BaF3, as well as with neutralizing IL-3 antibodies, are performed. Conditioned media that appear positive are adsorbed using soluble ALK-Fc protein to remove the proliferative activity. Cell lines producing conditioned medium with proliferative activity are used to prepare RNA for construction of expression libraries according to methods known in the art (see, e.g., Chapters 5 and 6 in *Current Protocols in Molecular Biology*, F. M. Ausubel et al., eds., John Wiley & Sons, Boston, Mass. (1994), pp. 5.0.1–6.12.12). Screening of these expression libraries can be performed as described above. Alternately, classical protein purification techniques can be performed to isolate ligands from positive conditioned media (see, e.g., Chapter 10 in *Current Protocols in Molecular Biology*, F. M. Ausubel et al., eds., John Wiley & Sons, Boston, Mass. (1994), pp. 10.0.1–10.19.12).

Characterization of ALK Ligand(s)

Once a cDNA encoding an ALK ligand has been isolated, the protein encoded by that cDNA is produced and characterized with respect to binding to ALK-Fc and to full-length ALK. Further, the biological effects of the ligand on ALK receptor-positive cells are determined. Expression of the ALK ligand is measured in normal adult and fetal murine organs, as well as in malignant tissues and cell lines, by Northern and in situ hybridizations and immunostaining. The chromosomal localization(s) of the gene(s) encoding ALK ligand(s) in humans and mice are identified to determine if the loci are involved in genetic diseases. Examples of genetic abnormalities involving receptor ligands include human X-linked immunodeficiency with hyper-IgM that is caused by mutation of the CD40 ligand gene (Korthauer, U. et al., *Nature* 361:539–541 (1993); Allen, R. C. et al., *Science* 259:990–993 (1993)), and anemia and defects in pigmentation and gametogenesis in Steel mutant mice that are caused by abnormalities of the KIT ligand gene locus (Copeland, N. G. et al., *Cell* 63:175–183 (1990)).

Identification of Ligands for Tissue-Specific Forms of ALK

As noted in Example 2(B), four different ALK transcripts of 4.4, 6.0, 6.5, and 8.0 kb are observed in Northern blot analysis of mRNAs from specific normal human tissues (small intestine, fetal and adult brain, colon, prostate, testis, placenta, and fetal liver) (FIG. 1(C)). These different transcripts may result from alternate transcriptional start sites and/or polyadenylation signals. However, studies of variant forms of several other PTKs have revealed differing coding sequences that produce tissue-specific forms which possess different ligand binding and biological activities. For example, the fibroblast growth factor receptor (FGFR) family members keratinocyte growth factor receptor (KGFR), which is expressed only in cells of epithelial origin, and FGFR-2, which is widely expressed, are identical except for a divergent stretch of 49 amino acids within the most membrane-proximal of the three immunoglobulin-like loops of their ligand-binding domain that results from alternative exon splicing. Whereas the KGFR binds both KGF and acidic FGF, FGFR-2 shows high affinity for basic and acidic FGF but no detectable binding of KGF (Werner, S. et al., *Mol. Cell. Biol.* 12:82–88 (1992)).

The coding sequences of the alternative ALK transcripts can be identified to determine whether they encode ALK isoforms that might bind separate ligands. RNA-PCR can be used to amplify products from the RNA of ALK-positive tissues, using primers that are synthesized based upon the ALK sequence. RACE methods can also be used to identify unique 5' ends which variant mRNAs could possess (Frohman, M. A. et al., *Proc. Natl. Acad. Sci. USA* 85:8998–9002 (1988)). This analysis can be complemented by DNA-PCR screening and conventional hybridization screening of commercially available tissue-specific cDNA libraries (Stratagene, La Jolla, Calif.) to isolate clones corresponding to the different ALK transcripts. Full-length cDNAs can be cloned or constructed that correspond to the ALK mRNAs that possess different coding sequences. These coding sequence variants are used in assays as described above to identify their interacting ligands.

F. Transgenic ALK "Knock-Out" Mice

Methods of Generating Transgenic Non-Human Animals

The non-human animals of the invention comprise any animal having a transgenic interruption or alteration of the endogenous ALK gene(s) (knock-out animals) and/or into the genome of which has been introduced one or more transgenes that direct the expression of human ALK or NPM/ALK.

Such non-human animals include vertebrates such as rodents, non-human primates, sheep, dog, cow, amphibians, reptiles, etc. Preferred non-human animals are selected from non-human mammalian species of animals, most preferably, animals from the rodent family including rats and mice, most preferably mice.

The transgenic animals of the invention are animals into which has been introduced by nonnatural means (i.e., by human manipulation), one or more genes that do not occur naturally in the animal, e.g., foreign genes, genetically engineered endogenous genes, etc. The nonnaturally introduced genes, known as transgenes, may be from the same or a different species as the animal but not naturally found in the animal in the configuration and/or at the chromosomal locus conferred by the transgene. Transgenes may comprise foreign DNA sequences, i.e., sequences not normally found in the genome of the host animal. Alternatively or additionally, transgenes may comprise endogenous DNA sequences that are abnormal in that they have been rearranged or mutated in vitro in order to alter the normal in vivo pattern of expression of the gene, or to alter or eliminate the biological activity of an endogenous gene product encoded by the gene. (Watson, J. D., et al., in *Recombinant DNA*, 2d Ed., W. H. Freeman & Co., New York (1992), pages 255–272; Gordon, J. W., *Intl. Rev. Cytol.* 115:171–229 (1989); Jaenisch, R., *Science* 240:1468–1474 (1989); Rossant, J., *Neuron* 2:323–334 (1990)).

The transgenic non-human animals of the invention are produced by introducing transgenes into the germline of the non-human animal. Embryonic target cells at various developmental stages are used to introduce the transgenes of the invention. Different methods are used depending on the stage of development of the embryonic target cell(s).

1. Microinjection of zygotes is the preferred method for incorporating transgenes into animal genomes in the course of practicing the invention. A zygote, a fertilized ovum that has not undergone pronuclei fusion or subsequent cell division, is the preferred target cell for microinjection of transgenic DNA sequences. The murine male pronucleus reaches a size of approximately 20 micrometers in diameter, a feature which allows for the reproducible injection of 1–2 picoliters of a solution containing transgenic DNA sequences. The use of a zygote for introduction of transgenes has the advantage that, in most cases, the injected transgenic DNA sequences will be incorporated into the host animal's genome before the first cell division (Brinster, et al., *Proc. Natl. Acad. Sci. (USA)* 82:4438–4442 (1985)). As a consequence, all cells of the resultant transgenic animals (founder animals) stably carry an incorporated transgene at a particular genetic locus, referred to as a transgenic allele. The transgenic allele demonstrates Mendelian inheritance: half of the offspring resulting from the cross of a transgenic animal with a non-transgenic animal will inherit the transgenic allele, in accordance with Mendel's rules of random assortment.

2. Viral integration can also be used to introduce the transgenes of the invention into an animal. The developing embryos are cultured in vitro to the developmental stage known as a blastocyst. At this time, the blastomeres may be infected with appropriate retroviruses (Jaenich, R., *Proc. Natl. Sci. (USA)* 73:1260–1264 (1976)). Infection of the blastomeres is enhanced by enzymatic removal of the zona pellucida (Hogan, et al., in *Manipulating the Mouse Embryo,* Cold Spring Harbor Press, Cold Spring Harbor, N.Y. (1986)). Transgenes are introduced via viral vectors which are typically replication-defective but which remain competent for integration of viral-associated DNA sequences, including transgenic DNA sequences linked to such viral sequences, into the host animal's genome (Jahner, et al., *Proc. Natl. Acad. Sci. (USA)* 82:6927–6931 (1985); Van der Putten, et al., *Proc. Natl. Acad. Sci. (USA)* 82:6148–6152 (1985)). Transfection is easily and efficiently obtained by culture of blastomeres on a mono-layer of cells producing the transgene-containing viral vector (Van der Putten, et al., *Proc. Natl. Acad. Sci. (USA)* 82:6148–6152 (1985); Stewart, et al., *EMBO Journal* 6:383–388 (1987)). Alternatively, infection may be performed at a later stage, such as a blastocoele (Jahner, D., et al., *Nature* 298:623–628 (1982)). In any event, most transgenic founder animals produced by viral integration will be mosaics for the transgenic allele; that is, the transgene is incorporated into only a subset of all the cells that form the transgenic founder animal. Moreover, multiple viral integration events may occur in a single founder animal, generating multiple transgenic alleles which will segregate in future generations of offspring. Introduction of transgenes into germline cells by this method is possible but probably occurs at a low frequency (Jahner, D., et al., *Nature* 298:623–628 (1982)). However, once a transgene has been introduced into germline cells by this method, offspring may be produced in which the transgenic allele is present in all of the animal's cells, i.e., in both somatic and germline cells.

3. Embryonic stem (ES) cells can also serve as target cells for introduction of the transgenes of the invention into animals. ES cells are obtained from pre-implantation embryos that are cultured in vitro (Evans, M. J., et al., *Nature* 292:154–156 (1981); Bradley, M. O., et al., *Nature* 309:255–258 (1984); Gossler, et al., *Proc. Natl. Acad. Sci. (USA)* 83:9065–9069 (1986); Robertson et al., *Nature* 322:445–448 (1986); Robertson, E. J., in *Teratocarcinomas* and *Embryonic Stem Cells: A Practical Approach,* Robertson, E. J., ed., IRL Press, Oxford (1987), pages 71–112). ES cells, which are commercially available (from, e.g., Genome Systems, Inc., St. Louis, Mo.), can be transformed with one or more transgenes by established methods (Lovell-Badge, R. H., in *Teratocarcinomas and Embryonic Stem Cells: A Practical Approach, Robertson,* E. J., ed., IRL Press, Oxford (1987), pages 153–182). Transformed ES cells can be combined with an animal blastocyst, whereafter the ES cells colonize the embryo and contribute to the germline of the resulting animal, which is a chimera (composed of cells derived from two or more animals) (Jaenisch, R., *Science* 240:1468–1474 (1988); Bradley, A., in *Teratocarcinomas and Embryonic Stem Cells: A Practical Approach,* Robertson, E. J., ed., IRL Press, Oxford (1987), pages 113–151). Again, once a transgene has been introduced into germline cells by this method, offspring may be produced in which the transgenic allele is present in all of the animal's cells, i.e., in both somatic and germline cells.

However it occurs, the initial introduction of a transgene is a Lamarckian (non-Mendelian) event. However, the transgenes of the invention may be stably integrated into germ line cells and transmitted to offspring of the transgenic animal as Mendelian loci. Other transgenic techniques result in mosaic transgenic animals, in which some cells carry the transgenes and other cells do not. In mosaic transgenic animals in which germ line cells do not carry the transgenes, transmission of the transgenes to offspring does not occur. Nevertheless, mosaic transgenic animals are capable of demonstrating phenotypes associated with the transgenes.

Transgenes may be introduced into non-human animals in order to provide animal models for human diseases. Transgenes that result in such animal models include, e.g., transgenes that encode mutant gene products associated with an inborn error of metabolism in a human genetic disease and transgenes that encode a human factor required to confer susceptibility to a human pathogen (i.e., a bacterium, virus, or other pathogenic microorganism) (Lederetal., U.S. Pat. No. 5,175,383 (Dec. 29, 1992); Kindtetal., U.S. Pat. No. 5,183,949 (Feb. 2, 1993); Small et al., *Cell* 46:13–18 (1986); Hooper et al., *Nature* 326:292–295 (1987); Stacey et al., *Nature* 332:131–136 (1988); Windle et al., *Nature* 343:665–669 (1990); Katz et al., *Cell* 74:1089–1100 (1993)). Transgenically introduced mutations comprise null ("knock-out") alleles in which a DNA sequence encoding a selectable and/or detectable marker is substituted for a genetic sequence normally endogenous to a non-human animal. Resultant transgenic non-human animals that are predisposed to a disease, or in which the transgene causes a disease, may be used to identify compositions that induce the disease and to evaluate the pathogenic potential of compositions known or suspected to induce the disease (Berns, A. J. M., U.S. Pat. No. 5,174,986 (Dec. 29, 1992)), or to evaluate compositions which may be used to treat the disease or ameliorate the symptoms thereof (Scott et al., WO 94/12627 (1994)).

Offspring that have inherited the transgenes of the invention are distinguished from littermates that have not inherited transgenes by analysis of genetic material from the offspring for the presence of biomolecules that comprise unique sequences corresponding to sequences of, or encoded by, the transgenes of the invention. For example, biological fluids that contain polypeptides uniquely encoded by the selectable marker of the transgenes of the invention may be immunoassayed for the presence of the polypeptides. A more simple and reliable means of identifying transgenic offspring comprises obtaining a tissue sample from an extremity of an animal, e.g., a tail, and analyzing the sample for the presence of nucleic acid sequences corresponding to the DNA sequence of a unique portion or portions of the transgenes of the invention, such as the selectable marker thereof. The presence of such nucleic acid sequences may be determined by, e.g., hybridization ("Southern") analysis with DNA sequences corresponding to unique portions of the transgene, analysis of the products of PCR reactions using DNA sequences in a sample as substrates and oligonucleotides derived from the transgene's DNA sequence, etc.

Production of Transgenic ALK-Disrupted Non-Human Animals

The ALK gene is disrupted, for example, by homologous recombination using murine ALK genomic clones isolated from a murine library (Genome Systems, St. Louis, Mo.) using one of the ALK nucleic acids of the invention as a probe. The genomic organization of a murine fragment contains a 186 bp exon (SEQ ID NO:11) encoding the juxtamembrane cytoplasmic residues of the ALK receptor and an 87 bp exon immediately downstream of the juxtamembrane region that encodes the N-terminal end of the kinase catalytic domain, including the G-X-G-X-X-G (SEQ ID NO:43) motif and invariant lysine that are required for ATP binding and kinase activity. Because these exons are retained in all alternatively-spliced ALK transcripts observed in Northern analysis of human organ mRNAs (as determined by Northern analyses using a cDNA probe having sequences corresponding to these exons), disruption of these sequences is expected to inactivate ALK gene transcription in all tissues.

A replacement type of targeting vector (Thomas & Capecchi, *Cell* 51:503–512 (1987)) was prepared using an EcoRI genomic fragment containing these two ALK exons flanked by approximately 6 kb and 4 kb of intronic sequence. Because the frequency of gene targeting greatly depends upon the length of homology between vector and target sequences (up to ~14 kb of homology) (Deng & Capecchi, *Mol. Cell Biol.* 12:3365–3371 (1992)), this large genomic ALK clone should ensure efficient homologous replacement. To ensure efficient identification of homologous recombinants, the targeting vector includes both neomycin phosphotransferase (neo$^r$) and herpes simplex virus thymidine kinase (hsv-tk) gene cassettes to permit positive and negative selection of targeted ES cell clones in G418 and gancyclovir (Mansour, S. L. et al., *Nature* 336:348–352 (1988)). To prepare the targeting construct, an approximately 2 kb genomic fragment that encompasses both the juxtamembrane and catalytic domain exons was deleted; inserted in its place is the neo$^r$ cassette, placed in the opposite orientation relative to ALK coding sequences to prevent the unwanted possibility of transcription of downstream ALK sequences (that encode the remainder of the tyrosine kinase catalytic domain and the C-terminus) driven by the neo$^r$ promoter. Truncated ALK transcripts, produced from the mutant genomic locus generated by homologous recombination with this vector, encode a functionally inactive receptor devoid of its cytoplasmic domains.

The purified, linearized targeting construct is introduced into CCE ES cells by electroporation; these cells are then grown in the presence of G418 and gancyclovir on a fibroblast feeder layer that produces leukemia inhibiting factor. Doubly resistant ES cells are analyzed by Southern blotting, as described in the preceding examples, to identify clones containing a disrupted ALK locus and to exclude the presence of additional randomly integrated copies of the targeting vector. Appropriate DNA probes from the regions immediately flanking the murine genomic sequences incorporated into the construct have also been identified and subcloned for use in Southern hybridization analysis to identify correctly targeted ES cells. The 5' flanking fragment is an approximately 2 kb EcoRI/KpnI genomic DNA restriction fragment, and the 3' flanking fragment is an approximately 3.8 kb HindIII/SpeI genomic DNA restriction fragment.

Appropriately targeted cells are injected into C57BL/6J blastocysts which are then implanted into uteri of pseudopregnant females and allowed to develop to term to produce chimeric animals. These chimeric animals are then mated to determine their ability to transmit the modified allele in the germline; resulting heterozygotes are intercrossed to generate ALK null animals.

Chimeric mice and mice heterozygous or homozygous for the mutant ALK allele are extensively examined for gross phenotypic as well as histopathologic abnormalities. Successful targeted disruption of several receptor PTKs has been reported, perhaps most notably the TRK family members and RET. In the case of the TRK genes, which encode neurotrophin receptors, multiple central and peripheral nervous system abnormalities were observed (Snider, W. D., Cell 77:627–638 (1994)). RET null mice exhibited renal agenesis and lacked enteric neurons throughout their digestive tract (Schuchardt, A. et al., Nature 367:380–383 (1994)). The lack of enteric innervation observed in RET null mice provides a biologic basis and an animal model for the role of the RET mutations detected in Hirschsprung's disease (congenital megacolon). The experience gained with these other PTKs is utilized in evaluating the transgenic ALK-disrupted mice of the invention.

G. Transgenic Mice Expressing ALK and NPM/ALK Transgenes or Derivatives of ALK and NPM/ALK Transgenes The present invention also encompasses transgenic non-human animals which express the human ALK and/or NPM/ALK transgenes. These transgenes may be regulated in a tissue specific or developmental stage specific manner.

Tissue Specific Transgenic Expression

An NPM/ALK transgene construct containing a promoter demonstrated to drive gene expression specifically within this cell type is used to express the NPM/ALK fusion protein in activated T-cells of a transgenic animal. One such construct contains 5' regulatory sequences of the human granzyme B gene, which encodes a T lymphocyte-specific serine protease (Hanson & Ley, Mol. Cell. Biol. 10:5655–5662 (1990); Hanson, R. D. et al., J. Biol. Chem. 266:2433–2438 (1991)). The granzyme B promoter has been used to target human growth hormone gene expression in activated T cells in transgenic mice; expression was seen in both CD4+ and CD8+ lymphocytes (Hanson, R. D. et al., J. Biol. Chem. 266:2433–2438 (1991)). Constitutive expression at the whole organ level was detected only in lymph nodes and the gamma/delta T cells of the Peyer's patches of small intestine. Expression driven by these regulatory sequences was tightly controlled, as none was detected in B lymphocytes nor resting T lymphocytes; in vitro stimulation of resting T cells from transgenic founders or F1 offspring with agents that produce signals acting through either the T-cell or interleukin-2 receptors (concanavalin A and/or IL-2) resulted in high level expression, however (Hanson, R. D. et al., J. Biol. Chem. 266:2433–2438 (1991)). Upregulation of transgene expression should also be possible in vivo by recurrent exposure of mice to activating agents (e.g., intraperitoneal antigen injection and/or intravenous IL-2) if desired. These sequences have also been used to express the HTLV-1 transcriptional trans acting protein Tax in mice; the Tax expression pattern paralleled that observed for growth hormone by Ley and colleagues and these mice developed lymphomas involving the cervical, axillary, and mesenteric lymph nodes and the skin (L. Ratner, Washington University School of Medicine; personal comm.).

Northern analysis of total RNA from the t(2;5)-containing lymphoma lines SUP-M2, SU-DHL-1 and UCONN-L2 indicated that the endogenous granzyme B gene is abundantly expressed and is upregulated greater than 10-fold with culture of the cells in IL-2. Thus, a granzyme B-NPM/ALK transgene should target lymphoid cells at the stage of differentiation typical of these human lymphomas.

The complete 2.4 kb EcoRV/SmaI NPM/ALK cDNA was ligated into BamHI-restricted and blunt-ended granzyme B promoter vector. Introns and polyadenylation signals are provided by the hGH gene to enhance transcriptional efficiency and message stability in this transgene (Hanson, R. D. et al., J. Biol. Chem. 266:2433–2438 (1991)). Transient expression of this granzyme B-NPM/ALK transgene is confirmed by electroporating the vector construct into the PEER cell line, a T-cell leukemia line that does not contain the t(2;5) translocation, followed by treatment with the phorbol ester TPA in combination with dibutyryl cyclic AMP to induce granzyme B promoter regulated expression (Hanson & Ley, Mol. Cell. Biol. 10:5655–5662 (1990)). G418-resistant PEER cells are tested for NPM/ALK mRNA and protein encoded by the construct upon stimulation, indicating responsiveness of NPM/ALK expression to the granzyme B promoter. In vitro autophosphorylation assays can also be performed on the NPM/ALK protein encoded by the construct to ensure functional activity.

Developmental Stage Specific Transgenic Expression

Despite the consistent involvement of activated T lymphocytes in large cell lymphomas with the t(2;5) translocation, it is not entirely clear that this phenotype represents the actual differentiation stage of the lymphoid cells targeted by NPM/ALK in vivo. The mature developmental stage of these transformed lymphocytes possibly results from the effects of the chimeric protein in immature T cell precursors that do not normally express granzyme B. Thus, in addition to assessing the oncogenicity of NPM/ALK in activated T lymphocytes by using the granzyme B construct, NPM/ALK transgenic mice are generated using a construct containing a promoter from a gene known to be transcriptionally active in early T-cell progenitors. For this purpose, vectors having either the LCK proximal promoter (Chaffin, K. E. et al., EMBO J. 9:3821–3829 (1990)) or the CD2 dominant control region (CD2 DCR) are used (Greaves, D. R. et al., Cell 56:986 (1989)). Both LCK and CD2 are expressed in the t(2;5) lymphoma lines disclosed herein. Using this strategy, a spectrum of developing lymphoid cells are exposed to NPM/ALK to determine its oncogenic potential.

Transgenes Expressing Mutant NPM/ALK and ALK Proteins

In addition to "wild-type" NPM/ALK, transgenic founders are prepared containing selected NPM/ALK mutant cDNAs in which functionally critical domains have been identified by in vitro analysis. After testing the functional activity of the transgene constructs, plasmid sequences are excised and the purified insert is used for the generation of transgenic founders. All procedures are performed using standard techniques (Hogan, B. F. et al., Manipulating the Mouse Embryo: A Laboratory Manual, Cold Spring Harbor Laboratory, Cold Spring Harbor, N.Y. (1986)). Transgenic founders are tested for NPM/ALK expression by S1 nuclease or PCR analysis of RNA from activated T-cells in tail blood, as previously described (Hanson, R. D. et al., *J. Biol. Chem.* 266:2433–2438 (1991)). Founders are mated with wild-type mice to obtain F1 generation transgenic mice.

Characterization of Transgenic Mice

To assess lymphocyte number and phenotype, transgenic mice and normal littermates, beginning at 3–4 weeks of age and subsequently at regular intervals, are examined using fluorescence-activated flow cytometry analysis (FACS) of single cell suspensions from bone marrow, thymus, spleen, lymph nodes, and peripheral blood. Expression of NPM/ALK mRNA and protein is concomitantly assessed in these samples. Additionally, if desired, the clonality of NPM/ALK-positive lymphoid tissue is determined by T-cell receptor and/or Ig gene rearrangement analysis of genomic DNAs from premalignant samples, as well as tumors. The cell cycle kinetics of NPM/ALK-positive cells is assessed, together with appropriate control cells from littermates, by FACS analysis of DNA content (Hollander & Loken, *Cytometry* 9:485–490 (1988)). Routine histo- and immuno-pathologic analysis (Stevens, A., in *Theory and Practice of Histological Techniques,* Bancroft, J. D., and Stevens, A., eds., 3rd Ed., Churchill Livingstone, Edinburgh, N.Y. (1990), pp. 107–118; Coleman, D. V., and Chapman, P.A., eds., *Clinical Cytotechnology, Butterworth & Co., London* (1989)) can be performed on all tissues in which transgene expression is likely, including the organs noted above and lymphoid tissues within the small intestine. In addition, total body surveys can be performed to identify unexpected organ involvement. Tumor cells can be tested for their ability to grow in syngeneic recipients and to form stable cell lines.

What is claimed is:

1. An isolated antibody that specifically binds a polypeptide consisting of the amino acid sequence of SEQ ID NO:2.

2. The isolated antibody of claim 1, wherein said antibody further specifically binds a polypeptide consisting of the amino acid sequence of SEQ ID NO:4.

3. An isolated antibody tat specifically binds a polypeptide consisting of the amino acid sequence of SEQ ID NO:7.

4. The isolated antibody of claim 1, wherein said ALK polypeptide is denatured.

5. The isolated antibody of claim 3, wherein said polypeptide is denatured.

6. An isolated antibody that specifically binds an isolated polypeptide, wherein said isolated polypeptide consists of at least one domain of an ALK polypeptide consisting of the amino acid sequence of SEQ ID NO:2, wherein said domain is selected from the group consisting of an extxacellular domain, a transmembrane domain, a catalytic domain, a signal peptide domain, an intracellular domain, a kinase domain, an immunoreactive domain and a fusion domain.

7. The isolated antibody of claim 6, wherein said isolated polypeptide is denatured.

8. The isolated antibody of claim 1, wherein said antibody specifically binds to a fragment and wherein said fragment consists of amino acids 27–1030 of SEQ ID NO:2.

9. The isolated antibody of claim 1, wherein said antibody specifically binds to a fragment and wherein said fragment comprises amino acids 1031–1058 of SEQ ID NQ:2.

10. The isolated antibody of claim 1, wherein said antibody specifically binds to a fragment and wherein said fragment comprises amino acids 1023–1376 of SEQ ID NO:2.

11. The isolated antibody of claim 1, wherein antibody specifically binds to a fragment and wherein said fragment comprises amino acids 1–26 of SEQ ID NO:2.

12. The isolated antibody of claim 1, wherein said antibody specifically binds to a fragment and wherein said fragment comprises amino acids 1059–1620 of SEQ ID NO:2.

13. The isolated antibody of claim 1, wherein said antibody specifically binds to a fragment and wherein said fragment comprises amino acids 605–1509 of SEQ ID NO:2.

14. The isolated antibody of claim 1, wherein said antibody specifically binds to a fragment and wherein said fragment comprises amino acids 1359–1460 of SEQ ID NO:2.

* * * * *

UNITED STATES PATENT AND TRADEMARK OFFICE
CERTIFICATE OF CORRECTION

PATENT NO. : 6,696,548 B2
DATED : February 24, 2004
INVENTOR(S) : Morris et al.

It is certified that error appears in the above-identified patent and that said Letters Patent is hereby corrected as shown below:

Column 2,
Line 28, please delete "5 q35" and insert therein -- 5q35 --.

Column 5,
Line 11, please delete "7leis" and insert therein -- 7les --.
Line 15, please delete "el" and insert therein -- et --.
Line 19, please delete "eta!.," and insert therein -- et al --.

Column 26,
Line 32, please delete "normalALK" and insert therein -- normal ALK --.

Column 45,
Line 38, please delete "(Lederetal.," and insert therein -- (Leder et al., --.
Line 39, please delete "Kindtetal.," and insert therein -- Kindt et al., --.

Column 48,
Line 13, please delete "complete 2.4 kb" and insert therein -- complete ~2.4 kb --.

Column 97,
Line 8, please delete "tat" and insert therein -- that --.
Line 19, please delete "extxacellular" and insert therein -- extracellular --.

Column 98,
Line 8, please delete "wherein antibody" and insert therein -- wherein said antibody --.

Signed and Sealed this

Twentieth Day of July, 2004

JON W. DUDAS
*Acting Director of the United States Patent and Trademark Office*

SEQUENCE LISTING

<160> NUMBER OF SEQ ID NOS: 43

<210> SEQ ID NO 1
<211> LENGTH: 6226
<212> TYPE: DNA
<213> ORGANISM: Homo sapiens
<220> FEATURE:
<221> NAME/KEY: CDS
<222> LOCATION: (912)..(5774)

<400> SEQUENCE: 1

```
aagcgggggc ggcagcggtg gtagcagctg gtacctcccg ccgcctctgt tcggagggtc       60
gcggggcacc gaggtgcttt ccggccgccc tctggtcggc cacccaaagc cgcgggcgct      120
gatgatgggt gaggaggggg cggcaagatt tcgggcgccc ctgccctgaa cgccctcagc      180
tgctgccgcc ggggccgctc cagtgcctgc gaactctgag gagccgaggc gccggtgaga      240
gcaaggacgc tgcaaacttg cgcagcgcgg gggctgggat tcacgcccag aagttcagca      300
ggcagacagt ccgaagcctt cccgcagcgg agagatagct tgagggtgcg caagacggca      360
gcctccgccc tcggttcccg cccagaccgg gcagaagagc ttggaggagc cacaaggaac      420
gcaaaaggcg gccaggacag cgtgcagcag ctgggagccg ccgttctcag ccttaaaagt      480
tgcagagatt ggaggctgcc ccgagagggg acagacccca gctccgactg cggggggcag      540
gagaggacgg tacccaactg ccacctccct tcaaccatag tagttcctct gtaccgagcg      600
cagcgagcta cagacggggg cgcggcactc ggcgcggaga gcgggaggct caaggtccca      660
gccagtgagc ccagtgtgct tgagtgtctc tggactcgcc cctgagcttc caggtctgtt      720
tcatttagac tcctgctcgc ctccgtgcag ttgggggaaa gcaagagact tgcgcgcacg      780
cacagtcctc tggagatcag gtggaaggag ccgctgggta ccaaggactg ttcagagcct      840
cttcccatct cggggagagc gaagggtgag gctgggcccg gagagcagtg taaacggcct      900
cctccggcgg g atg gga gcc atc ggg ctc ctg tgg ctg ctg ccg ctg ctg        950
            Met Gly Ala Ile Gly Leu Leu Trp Leu Leu Pro Leu Leu
              1               5                   10 ctt tcc acg gca gct gtg ggc tcc ggg atg ggg acc ggc cag cgc gcg        998
Leu Ser Thr Ala Ala Val Gly Ser Gly Met Gly Thr Gly Gln Arg Ala
     15                  20                  25 ggc tcc cca gct gcg ggg tcg ccg ctg cag ccc cgg gag cca ctc agc       1046
Gly Ser Pro Ala Ala Gly Ser Pro Leu Gln Pro Arg Glu Pro Leu Ser
 30                  35                  40                  45 tac tcg cgc ctg cag agg aag agt ctg gca gtt gac ttc gtg gtg ccc       1094
```

```
Tyr Ser Arg Leu Gln Arg Lys Ser Leu Ala Val Asp Phe Val Val Pro
             50                  55                  60 tcg ctc ttc cgt gtc tac gcc cgg gac cta ctg ctg cca cca tcc tcc      1142
Ser Leu Phe Arg Val Tyr Ala Arg Asp Leu Leu Leu Pro Pro Ser Ser
             65                  70                  75 tcg gag ctg aag gct ggc agg ccc gag gcc cgc ggc tcg cta gct ctg      1190
Ser Glu Leu Lys Ala Gly Arg Pro Glu Ala Arg Gly Ser Leu Ala Leu
             80                  85                  90 gac tgc gcc ccg ctg ctc agg ttg ctg ggg ccg gcg ccg ggg gtc tcc      1238
Asp Cys Ala Pro Leu Leu Arg Leu Leu Gly Pro Ala Pro Gly Val Ser
         95                 100                 105 tgg acc gcc ggt tca cca gcc ccg gca gag gcc cgg acg ctg tcc agg      1286
Trp Thr Ala Gly Ser Pro Ala Pro Ala Glu Ala Arg Thr Leu Ser Arg
110             115                 120                 125 gtg ctg aag ggc ggc tcc gtg cgc aag ctc cgg cgt gcc aag cag ttg      1334
Val Leu Lys Gly Gly Ser Val Arg Lys Leu Arg Arg Ala Lys Gln Leu
                130                 135                 140 gtg ctg gag ctg ggc gag gag gcg atc ttg gag ggt tgc gtc ggg ccc      1382
Val Leu Glu Leu Gly Glu Glu Ala Ile Leu Glu Gly Cys Val Gly Pro
                145                 150                 155 ccc ggg gag gcg gct gtg ggg ctg ctc cag ttc aat ctc agc gag ctg      1430
Pro Gly Glu Ala Ala Val Gly Leu Leu Gln Phe Asn Leu Ser Glu Leu
                160                 165                 170 ttc agt tgg tgg att cgc caa ggc gaa ggg cga ctg agg atc cgc ctg      1478
Phe Ser Trp Trp Ile Arg Gln Gly Glu Gly Arg Leu Arg Ile Arg Leu
        175                 180                 185 atg ccc gag aag aag gcg tcg gaa gtg ggc aga gag gga agg ctg tcc      1526
Met Pro Glu Lys Lys Ala Ser Glu Val Gly Arg Glu Gly Arg Leu Ser
190                 195                 200                 205 gcg gca att cgc gcc tcc cag ccc cgc ctt ctc ttc cag atc ttc ggg      1574
Ala Ala Ile Arg Ala Ser Gln Pro Arg Leu Leu Phe Gln Ile Phe Gly
                210                 215                 220 act ggt cat agc tcc ttg gaa tca cca aca aac atg cca tct cct tct      1622
Thr Gly His Ser Ser Leu Glu Ser Pro Thr Asn Met Pro Ser Pro Ser
            225                 230                 235 cct gat tat ttt aca tgg aat ctc acc tgg ata atg aaa gac tcc ttc      1670
Pro Asp Tyr Phe Thr Trp Asn Leu Thr Trp Ile Met Lys Asp Ser Phe
        240                 245                 250 cct ttc ctg tct cat cgc agc cga tat ggt ctg gag tgc agc ttt gac      1718
Pro Phe Leu Ser His Arg Ser Arg Tyr Gly Leu Glu Cys Ser Phe Asp
        255                 260                 265 ttc ccc tgt gag ctg gag tat tcc cct cca ctg cat gac ctc agg aac      1766
Phe Pro Cys Glu Leu Glu Tyr Ser Pro Pro Leu His Asp Leu Arg Asn
270                 275                 280                 285 cag agc tgg tcc tgg cgc cgc atc ccc tcc gag gag gcc tcc cag atg      1814
Gln Ser Trp Ser Trp Arg Arg Ile Pro Ser Glu Glu Ala Ser Gln Met
                290                 295                 300 gac ttg ctg gat ggg cct ggg gca gag cgt tct aag gag atg ccc aga      1862
Asp Leu Leu Asp Gly Pro Gly Ala Glu Arg Ser Lys Glu Met Pro Arg
                305                 310                 315 ggc tcc ttt ctc ctt ctc aac acc tca gct gac tcc aag cac acc atc      1910
Gly Ser Phe Leu Leu Leu Asn Thr Ser Ala Asp Ser Lys His Thr Ile
                320                 325                 330 ctg agt ccg tgg atg agg agc agc agt gag cac tgc aca ctg gcc gtc      1958
Leu Ser Pro Trp Met Arg Ser Ser Ser Glu His Cys Thr Leu Ala Val
            335                 340                 345 tcg gtg cac agg cac ctg cag ccc tct gga agg tac att gcc cag ctg      2006
Ser Val His Arg His Leu Gln Pro Ser Gly Arg Tyr Ile Ala Gln Leu
350                 355                 360                 365
```

```
ctg ccc cac aac gag gct gca aga gag atc ctc ctg atg ccc act cca     2054
Leu Pro His Asn Glu Ala Ala Arg Glu Ile Leu Leu Met Pro Thr Pro
            370                 375                 380 ggg aag cat ggt tgg aca gtg ctc cag gga aga atc ggg cgt cca gac     2102
Gly Lys His Gly Trp Thr Val Leu Gln Gly Arg Ile Gly Arg Pro Asp
        385                 390                 395 aac cca ttt cga gtg gcc ctg gaa tac atc tcc agt gga aac cgc agc     2150
Asn Pro Phe Arg Val Ala Leu Glu Tyr Ile Ser Ser Gly Asn Arg Ser
    400                 405                 410 ttg tct gca gtg gac ttc ttt gcc ctg aag aac tgc agt gaa gga aca     2198
Leu Ser Ala Val Asp Phe Phe Ala Leu Lys Asn Cys Ser Glu Gly Thr
415                 420                 425 tcc cca ggc tcc aag atg gcc ctg cag agc tcc ttc act tgt tgg aat     2246
Ser Pro Gly Ser Lys Met Ala Leu Gln Ser Ser Phe Thr Cys Trp Asn
430                 435                 440                 445 ggg aca gtc ctc cag ctt ggg cag gcc tgt gac ttc cac cag gac tgt     2294
Gly Thr Val Leu Gln Leu Gly Gln Ala Cys Asp Phe His Gln Asp Cys
            450                 455                 460 gcc cag gga gaa gat gag agc cag atg tgc cgg aaa ctg cct gtg ggt     2342
Ala Gln Gly Glu Asp Glu Ser Gln Met Cys Arg Lys Leu Pro Val Gly
        465                 470                 475 ttt tac tgc aac ttt gaa gat ggc ttc tgt ggc tgg acc caa ggc aca     2390
Phe Tyr Cys Asn Phe Glu Asp Gly Phe Cys Gly Trp Thr Gln Gly Thr
    480                 485                 490 ctg tca ccc cac act cct cag tgg cag gtc agg acc cta aag gat gcc     2438
Leu Ser Pro His Thr Pro Gln Trp Gln Val Arg Thr Leu Lys Asp Ala
495                 500                 505 cgg ttc cag gac cac caa gac cat gct cta ttg ctc agt acc act gat     2486
Arg Phe Gln Asp His Gln Asp His Ala Leu Leu Leu Ser Thr Thr Asp
510                 515                 520                 525 gtc ccc gct tct gaa agt gct aca gtg acc agt gct acg ttt cct gca     2534
Val Pro Ala Ser Glu Ser Ala Thr Val Thr Ser Ala Thr Phe Pro Ala
            530                 535                 540 ccg atc aag agc tct cca tgt gag ctc cga atg tcc tgg ctc att cgt     2582
Pro Ile Lys Ser Ser Pro Cys Glu Leu Arg Met Ser Trp Leu Ile Arg
        545                 550                 555 gga gtc ttg agg gga aac gtg tcc ttg gtg cta gtg gag aac aaa acc     2630
Gly Val Leu Arg Gly Asn Val Ser Leu Val Leu Val Glu Asn Lys Thr
    560                 565                 570 ggg aag gag caa ggc agg atg gtc tgg cat gtc gcc gcc tat gaa ggc     2678
Gly Lys Glu Gln Gly Arg Met Val Trp His Val Ala Ala Tyr Glu Gly
575                 580                 585 ttg agc ctg tgg cag tgg atg gtg ttg cct ctc ctc gat gtg tct gac     2726
Leu Ser Leu Trp Gln Trp Met Val Leu Pro Leu Leu Asp Val Ser Asp
590                 595                 600                 605 agg ttc tgg ctg cag atg gtc gca tgg tgg gga caa gga tcc aga gcc     2774
Arg Phe Trp Leu Gln Met Val Ala Trp Trp Gly Gln Gly Ser Arg Ala
            610                 615                 620 atc gtg gct ttt gac aat atc tcc atc agc ctg gac tgc tac ctc acc     2822
Ile Val Ala Phe Asp Asn Ile Ser Ile Ser Leu Asp Cys Tyr Leu Thr
        625                 630                 635 att agc gga gag gac aag atc ctg cag aat aca gca ccc aaa tca aga     2870
Ile Ser Gly Glu Asp Lys Ile Leu Gln Asn Thr Ala Pro Lys Ser Arg
    640                 645                 650 aac ctg ttt gag aga aac cca aac aag gag ctg aaa ccc ggg gaa aat     2918
Asn Leu Phe Glu Arg Asn Pro Asn Lys Glu Leu Lys Pro Gly Glu Asn
655                 660                 665 tca cca aga cag acc ccc atc ttt gac cct aca gtt cat tgg ctg ttc     2966
Ser Pro Arg Gln Thr Pro Ile Phe Asp Pro Thr Val His Trp Leu Phe
670                 675                 680                 685
```

```
acc aca tgt ggg gcc agc ggg ccc cat ggc ccc acc cag gca cag tgc    3014
Thr Thr Cys Gly Ala Ser Gly Pro His Gly Pro Thr Gln Ala Gln Cys
                690             695             700 aac aac gcc tac cag aac tcc aac ctg agc gtg gag gtg ggg agc gag    3062
Asn Asn Ala Tyr Gln Asn Ser Asn Leu Ser Val Glu Val Gly Ser Glu
            705             710             715 ggc ccc ctg aaa ggc atc cag atc tgg aag gtg cca gcc acc gac acc    3110
Gly Pro Leu Lys Gly Ile Gln Ile Trp Lys Val Pro Ala Thr Asp Thr
        720             725             730 tac agc atc tcg ggc tac gga gct gct ggc ggg aaa ggc ggg aag aac    3158
Tyr Ser Ile Ser Gly Tyr Gly Ala Ala Gly Gly Lys Gly Gly Lys Asn
735             740             745 acc atg atg cgg tcc cac ggc gtg tct gtg ctg ggc atc ttc aac ctg    3206
Thr Met Met Arg Ser His Gly Val Ser Val Leu Gly Ile Phe Asn Leu
750             755             760             765 gag aag gat gac atg ctg tac atc ctg gtt ggg cag cag gga gag gac    3254
Glu Lys Asp Asp Met Leu Tyr Ile Leu Val Gly Gln Gln Gly Glu Asp
                770             775             780 gcc tgc ccc agt aca aac cag tta atc cag aaa gtc tgc att gga gag    3302
Ala Cys Pro Ser Thr Asn Gln Leu Ile Gln Lys Val Cys Ile Gly Glu
            785             790             795 aac aat gtg ata gaa gaa gaa atc cgt gtg aac aga agc gtg cat gag    3350
Asn Asn Val Ile Glu Glu Glu Ile Arg Val Asn Arg Ser Val His Glu
        800             805             810 tgg gca gga ggc gga gga gga ggg ggt gga gcc acc tac gta ttt aag    3398
Trp Ala Gly Gly Gly Gly Gly Gly Gly Gly Ala Thr Tyr Val Phe Lys
815             820             825 atg aag gat gga gtg ccg gtg ccc ctg atc att gca gcc gga ggt ggc    3446
Met Lys Asp Gly Val Pro Val Pro Leu Ile Ile Ala Ala Gly Gly Gly
830             835             840             845 ggc agg gcc tac ggg gcc aag aca gac acg ttc cac cca gag aga ctg    3494
Gly Arg Ala Tyr Gly Ala Lys Thr Asp Thr Phe His Pro Glu Arg Leu
                850             855             860 gag aat aac tcc tcg gtt cta ggg cta aac ggc aat tcc gga gcc gca    3542
Glu Asn Asn Ser Ser Val Leu Gly Leu Asn Gly Asn Ser Gly Ala Ala
            865             870             875 ggt ggt gga ggt ggc tgg aat gat aac act tcc ttg ctc tgg gcc gga    3590
Gly Gly Gly Gly Gly Trp Asn Asp Asn Thr Ser Leu Leu Trp Ala Gly
        880             885             890 aaa tct ttg cag gag ggt gcc acc gga gga cat tcc tgc ccc cag gcc    3638
Lys Ser Leu Gln Glu Gly Ala Thr Gly Gly His Ser Cys Pro Gln Ala
895             900             905 atg aag aag tgg ggg tgg gag aca aga ggg ggt ttc gga ggg ggt gga    3686
Met Lys Lys Trp Gly Trp Glu Thr Arg Gly Gly Phe Gly Gly Gly Gly
910             915             920             925 ggg ggg tgc tcc tca ggt gga gga ggc gga gga tat ata ggc ggc aat    3734
Gly Gly Cys Ser Ser Gly Gly Gly Gly Gly Tyr Ile Gly Gly Asn
                930             935             940 gca gcc tca aac aat gac ccc gaa atg gat ggg gaa gat ggg gtt tcc    3782
Ala Ala Ser Asn Asn Asp Pro Glu Met Asp Gly Glu Asp Gly Val Ser
            945             950             955 ttc atc agt cca ctg ggc atc ctg tac acc cca gct tta aaa gtg atg    3830
Phe Ile Ser Pro Leu Gly Ile Leu Tyr Thr Pro Ala Leu Lys Val Met
        960             965             970 gaa ggc cac ggg gaa gtg aat att aag cat tat cta aac tgc agt cac    3878
Glu Gly His Gly Glu Val Asn Ile Lys His Tyr Leu Asn Cys Ser His
975             980             985 tgt gag gta gac gaa tgt cac atg gac cct gaa     agc cac aag gtc atc    3926
Cys Glu Val Asp Glu Cys His Met Asp Pro Glu     Ser His Lys Val Ile
```

```
                   -continued 990              995              1000             1005 tgc ttc tgt gac cac ggg acg gtg ctg gct gag gat ggc gtc tcc    3971
Cys Phe Cys Asp His Gly Thr Val Leu Ala Glu Asp Gly Val Ser
                1010             1015             1020 tgc att gtg tca ccc acc ccg gag cca cac ctg cca ctc tcg ctg    4016
Cys Ile Val Ser Pro Thr Pro Glu Pro His Leu Pro Leu Ser Leu
                1025             1030             1035 atc ctc tct gtg gtg acc tct gcc ctc gtg gcc gcc ctg gtc ctg    4061
Ile Leu Ser Val Val Thr Ser Ala Leu Val Ala Ala Leu Val Leu
                1040             1045             1050 gct ttc tcc ggc atc atg att gtg tac cgc cgg aag cac cag gag    4106
Ala Phe Ser Gly Ile Met Ile Val Tyr Arg Arg Lys His Gln Glu
                1055             1060             1065 ctg caa gcc atg cag atg gag ctg cag agc cct gag tac aag ctg    4151
Leu Gln Ala Met Gln Met Glu Leu Gln Ser Pro Glu Tyr Lys Leu
                1070             1075             1080 agc aag ctc cgc acc tcg acc atc atg acc gac tac aac ccc aac    4196
Ser Lys Leu Arg Thr Ser Thr Ile Met Thr Asp Tyr Asn Pro Asn
                1085             1090             1095 tac tgc ttt gct ggc aag acc tcc tcc atc agt gac ctg aag gag    4241
Tyr Cys Phe Ala Gly Lys Thr Ser Ser Ile Ser Asp Leu Lys Glu
                1100             1105             1110 gtg ccg cgg aaa aac atc acc ctc att cgg ggt ctg ggc cat ggc    4286
Val Pro Arg Lys Asn Ile Thr Leu Ile Arg Gly Leu Gly His Gly
                1115             1120             1125 gcc ttt ggg gag gtg tat gaa ggc cag gtg tcc gga atg ccc aac    4331
Ala Phe Gly Glu Val Tyr Glu Gly Gln Val Ser Gly Met Pro Asn
                1130             1135             1140 gac cca agc ccc ctg caa gtg gct gtg aag acg ctg cct gaa gtg    4376
Asp Pro Ser Pro Leu Gln Val Ala Val Lys Thr Leu Pro Glu Val
                1145             1150             1155 tgc tct gaa cag gac gaa ctg gat ttc ctc atg gaa gcc ctg atc    4421
Cys Ser Glu Gln Asp Glu Leu Asp Phe Leu Met Glu Ala Leu Ile
                1160             1165             1170 atc agc aaa ttc aac cac cag aac att gtt cgc tgc att ggg gtg    4466
Ile Ser Lys Phe Asn His Gln Asn Ile Val Arg Cys Ile Gly Val
                1175             1180             1185 agc ctg caa tcc ctg ccc cgg ttc atc ctg ctg gag ctc atg gcg    4511
Ser Leu Gln Ser Leu Pro Arg Phe Ile Leu Leu Glu Leu Met Ala
                1190             1195             1200 ggg gga gac ctc aag tcc ttc ctc cga gag acc cgc cct cgc ccg    4556
Gly Gly Asp Leu Lys Ser Phe Leu Arg Glu Thr Arg Pro Arg Pro
                1205             1210             1215 agc cag ccc tcc tcc ctg gcc atg ctg gac ctt ctg cac gtg gct    4601
Ser Gln Pro Ser Ser Leu Ala Met Leu Asp Leu Leu His Val Ala
                1220             1225             1230 cgg gac att gcc tgt ggc tgt cag tat ttg gag gaa aac cac ttc    4646
Arg Asp Ile Ala Cys Gly Cys Gln Tyr Leu Glu Glu Asn His Phe
                1235             1240             1245 atc cac cga gac att gct gcc aga aac tgc ctc ttg acc tgt cca    4691
Ile His Arg Asp Ile Ala Ala Arg Asn Cys Leu Leu Thr Cys Pro
                1250             1255             1260 ggc cct gga aga gtg gcc aag att gga gac ttc ggg atg gcc cga    4736
Gly Pro Gly Arg Val Ala Lys Ile Gly Asp Phe Gly Met Ala Arg
                1265             1270             1275 gac atc tac agg gcg agc tac tat aga aag gga ggc tgt gcc atg    4781
Asp Ile Tyr Arg Ala Ser Tyr Tyr Arg Lys Gly Gly Cys Ala Met
                1280             1285             1290 ctg cca gtt aag tgg atg ccc cca gag gcc ttc atg gaa gga ata    4826
```

```
                  Leu Pro Val Lys Trp  Met Pro Pro Glu Ala  Phe Met Glu Gly Ile
                                  1295                1300                1305 ttc act tct aaa aca  gac aca tgg tcc ttt  gga gtg ctg cta tgg         4871
Phe Thr Ser Lys Thr  Asp Thr Trp Ser Phe  Gly Val Leu Leu Trp
            1310                1315                1320 gaa atc ttt tct ctt  gga tat atg cca tac  ccc agc aaa agc aac         4916
Glu Ile Phe Ser Leu  Gly Tyr Met Pro Tyr  Pro Ser Lys Ser Asn
            1325                1330                1335 cag gaa gtt ctg gag  ttt gtc acc agt gga  ggc cgg atg gac cca         4961
Gln Glu Val Leu Glu  Phe Val Thr Ser Gly  Gly Arg Met Asp Pro
            1340                1345                1350 ccc aag aac tgc cct  ggg cct gta tac cgg  ata atg act cag tgc         5006
Pro Lys Asn Cys Pro  Gly Pro Val Tyr Arg  Ile Met Thr Gln Cys
            1355                1360                1365 tgg caa cat cag cct  gaa gac agg ccc aac  ttt gcc atc att ttg         5051
Trp Gln His Gln Pro  Glu Asp Arg Pro Asn  Phe Ala Ile Ile Leu
            1370                1375                1380 gag agg att gaa tac  tgc acc cag gac ccg  gat gta atc aac acc         5096
Glu Arg Ile Glu Tyr  Cys Thr Gln Asp Pro  Asp Val Ile Asn Thr
            1385                1390                1395 gct ttg ccg ata gaa  tat ggt cca ctt gtg  gaa gag gaa gag aaa         5141
Ala Leu Pro Ile Glu  Tyr Gly Pro Leu Val  Glu Glu Glu Glu Lys
            1400                1405                1410 gtg cct gtg agg ccc  aag gac cct gag ggg  gtt cct cct ctc ctg         5186
Val Pro Val Arg Pro  Lys Asp Pro Glu Gly  Val Pro Pro Leu Leu
            1415                1420                1425 gtc tct caa cag gca  aaa cgg gag gag gag  cgc agc cca gct gcc         5231
Val Ser Gln Gln Ala  Lys Arg Glu Glu Glu  Arg Ser Pro Ala Ala
            1430                1435                1440 cca cca cct ctg cct  acc acc tcc tct ggc  aag gct gca aag aaa         5276
Pro Pro Pro Leu Pro  Thr Thr Ser Ser Gly  Lys Ala Ala Lys Lys
            1445                1450                1455 ccc aca gct gca gag  gtc tct gtt cga gtc  cct aga ggg ccg gcc         5321
Pro Thr Ala Ala Glu  Val Ser Val Arg Val  Pro Arg Gly Pro Ala
            1460                1465                1470 gtg gaa ggg gga cac  gtg aat atg gca ttc  tct cag tcc aac cct         5366
Val Glu Gly Gly His  Val Asn Met Ala Phe  Ser Gln Ser Asn Pro
            1475                1480                1485 cct tcg gag ttg cac  aag gtc cac gga tcc  aga aac aag ccc acc         5411
Pro Ser Glu Leu His  Lys Val His Gly Ser  Arg Asn Lys Pro Thr
            1490                1495                1500 agc ttg tgg aac cca  acg tac ggc tcc tgg  ttt aca gag aaa ccc         5456
Ser Leu Trp Asn Pro  Thr Tyr Gly Ser Trp  Phe Thr Glu Lys Pro
            1505                1510                1515 acc aaa aag aat aat  cct ata gca aag aag  gag cca cac gac agg         5501
Thr Lys Lys Asn Asn  Pro Ile Ala Lys Lys  Glu Pro His Asp Arg
            1520                1525                1530 ggt aac ctg ggg ctg  gag gga agc tgt act  gtc cca cct aac gtt         5546
Gly Asn Leu Gly Leu  Glu Gly Ser Cys Thr  Val Pro Pro Asn Val
            1535                1540                1545 gca act ggg aga ctt  ccg ggg gcc tca ctg  ctc cta gag ccc tct         5591
Ala Thr Gly Arg Leu  Pro Gly Ala Ser Leu  Leu Leu Glu Pro Ser
            1550                1555                1560 tcg ctg act gcc aat  atg aag gag gta cct  ctg ttc agg cta cgt         5636
Ser Leu Thr Ala Asn  Met Lys Glu Val Pro  Leu Phe Arg Leu Arg
            1565                1570                1575 cac ttc cct tgt ggg  aat gtc aat tac ggc  tac cag caa cag ggc         5681
His Phe Pro Cys Gly  Asn Val Asn Tyr Gly  Tyr Gln Gln Gln Gly
            1580                1585                1590
```

-continued

| | | |
|---|---|---|
| ttg ccc tta gaa gcc gct act gcc cct gga gct ggt cat tac gag<br>Leu Pro Leu Glu Ala Ala Thr Ala Pro Gly Ala Gly His Tyr Glu<br>               1595                       1600                       1605 | 5726 |
| gat acc att ctg aaa agc aag aat agc atg aac cag cct ggg ccc<br>Asp Thr Ile Leu Lys Ser Lys Asn Ser Met Asn Gln Pro Gly Pro<br>               1610                       1615                       1620 | 5771 |
| tga gctcggtcgc acactcactt ctcttccttg ggatccctaa gaccgtggag | 5824 |
| gagagagagg caatggctcc ttcacaaacc agagaccaaa tgtcacgttt tgttttgtgc | 5884 |
| caacctattt tgaagtacca ccaaaaaagc tgtattttga aaatgcttta gaaaggtttt | 5944 |
| gagcatgggt tcatcctatt ctttcgaaag aagaaaatat cataaaaatg agtgataaat | 6004 |
| acaaggccca gatgtggttg cataaggttt ttatgcatgt ttgttgtata cttccttatg | 6064 |
| cttcttttaa attgtgtgtg ctctgcttca atgtagtcag aattagctgc ttctatgttt | 6124 |
| catagttggg gtcatagatg tttccttgcc ttgttgatgt ggacatgagc catttgaggg | 6184 |
| gagagggaac ggaaataaag gagttatttg taatgactaa aa | 6226 |

<210> SEQ ID NO 2
<211> LENGTH: 1620
<212> TYPE: PRT
<213> ORGANISM: Homo sapiens

<400> SEQUENCE: 2

Met Gly Ala Ile Gly Leu Leu Trp Leu Leu Pro Leu Leu Leu Ser Thr
1               5                    10                  15

Ala Ala Val Gly Ser Gly Met Gly Thr Gly Gln Arg Ala Gly Ser Pro
            20                    25                    30

Ala Ala Gly Ser Pro Leu Gln Pro Arg Glu Pro Leu Ser Tyr Ser Arg
        35                    40                    45

Leu Gln Arg Lys Ser Leu Ala Val Asp Phe Val Val Pro Ser Leu Phe
50                    55                    60

Arg Val Tyr Ala Arg Asp Leu Leu Leu Pro Pro Ser Ser Ser Glu Leu
65                70                    75                    80

Lys Ala Gly Arg Pro Glu Ala Arg Gly Ser Leu Ala Leu Asp Cys Ala
            85                    90                    95

Pro Leu Leu Arg Leu Leu Gly Pro Ala Pro Gly Val Ser Trp Thr Ala
        100                    105                  110

Gly Ser Pro Ala Pro Ala Glu Ala Arg Thr Leu Ser Arg Val Leu Lys
       115                  120                 125

Gly Gly Ser Val Arg Lys Leu Arg Arg Ala Lys Gln Leu Val Leu Glu
   130                   135                  140

Leu Gly Glu Glu Ala Ile Leu Glu Gly Cys Val Gly Pro Pro Gly Glu
145                 150                  155               160

Ala Ala Val Gly Leu Leu Gln Phe Asn Leu Ser Glu Leu Phe Ser Trp
           165                  170               175

Trp Ile Arg Gln Gly Glu Gly Arg Leu Arg Ile Arg Leu Met Pro Glu
        180                  185                190

Lys Lys Ala Ser Glu Val Gly Arg Glu Gly Arg Leu Ser Ala Ala Ile
      195                200                 205

Arg Ala Ser Gln Pro Arg Leu Leu Phe Gln Ile Phe Gly Thr Gly His
  210                  215                220

Ser Ser Leu Glu Ser Pro Thr Asn Met Pro Ser Pro Ser Pro Asp Tyr
225                 230                  235               240

Phe Thr Trp Asn Leu Thr Trp Ile Met Lys Asp Ser Phe Pro Phe Leu
           245                  250               255

-continued

```
Ser His Arg Ser Arg Tyr Gly Leu Glu Cys Ser Phe Asp Phe Pro Cys
            260                 265                 270

Glu Leu Glu Tyr Ser Pro Pro Leu His Asp Leu Arg Asn Gln Ser Trp
            275                 280                 285

Ser Trp Arg Arg Ile Pro Ser Glu Glu Ala Ser Gln Met Asp Leu Leu
            290                 295                 300

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
                325                 330                 335

Trp Met Arg Ser Ser Glu His Cys Thr Leu Ala Val Ser Val His
            340                 345                 350

Arg His Leu Gln Pro Ser Gly Arg Tyr Ile Ala Gln Leu Leu Pro His
            355                 360                 365

Asn Glu Ala Ala Arg Glu Ile Leu Leu Met Pro Thr Pro Gly Lys His
            370                 375                 380

Gly Trp Thr Val Leu Gln Gly Arg Ile Gly Arg Pro Asp Asn Pro Phe
385                 390                 395                 400

Arg Val Ala Leu Glu Tyr Ile Ser Ser Gly Asn Arg Ser Leu Ser Ala
                405                 410                 415

Val Asp Phe Phe Ala Leu Lys Asn Cys Ser Glu Gly Thr Ser Pro Gly
                420                 425                 430

Ser Lys Met Ala Leu Gln Ser Ser Phe Thr Cys Trp Asn Gly Thr Val
            435                 440                 445

Leu Gln Leu Gly Gln Ala Cys Asp Phe His Gln Asp Cys Ala Gln Gly
            450                 455                 460

Glu Asp Glu Ser Gln Met Cys Arg Lys Leu Pro Val Gly Phe Tyr Cys
465                 470                 475                 480

Asn Phe Glu Asp Gly Phe Cys Gly Trp Thr Gln Gly Thr Leu Ser Pro
                485                 490                 495

His Thr Pro Gln Trp Gln Val Arg Thr Leu Lys Asp Ala Arg Phe Gln
            500                 505                 510

Asp His Gln Asp His Ala Leu Leu Leu Ser Thr Thr Asp Val Pro Ala
            515                 520                 525

Ser Glu Ser Ala Thr Val Thr Ser Ala Thr Phe Pro Ala Pro Ile Lys
            530                 535                 540

Ser Ser Pro Cys Glu Leu Arg Met Ser Trp Leu Ile Arg Gly Val Leu
545                 550                 555                 560

Arg Gly Asn Val Ser Leu Val Leu Val Glu Asn Lys Thr Gly Lys Glu
                565                 570                 575

Gln Gly Arg Met Val Trp His Val Ala Ala Tyr Glu Gly Leu Ser Leu
            580                 585                 590

Trp Gln Trp Met Val Leu Pro Leu Leu Asp Val Ser Asp Arg Phe Trp
            595                 600                 605

Leu Gln Met Val Ala Trp Trp Gly Gln Gly Ser Arg Ala Ile Val Ala
            610                 615                 620

Phe Asp Asn Ile Ser Ile Ser Leu Asp Cys Tyr Leu Thr Ile Ser Gly
625                 630                 635                 640

Glu Asp Lys Ile Leu Gln Asn Thr Ala Pro Lys Ser Arg Asn Leu Phe
                645                 650                 655

Glu Arg Asn Pro Asn Lys Glu Leu Lys Pro Gly Glu Asn Ser Pro Arg
            660                 665                 670
```

```
Gln Thr Pro Ile Phe Asp Pro Thr Val His Trp Leu Phe Thr Thr Cys
            675                 680                 685

Gly Ala Ser Gly Pro His Gly Pro Thr Gln Ala Gln Cys Asn Asn Ala
    690                 695                 700

Tyr Gln Asn Ser Asn Leu Ser Val Glu Val Gly Ser Glu Gly Pro Leu
705                 710                 715                 720

Lys Gly Ile Gln Ile Trp Lys Val Pro Ala Thr Asp Thr Tyr Ser Ile
            725                 730                 735

Ser Gly Tyr Gly Ala Ala Gly Lys Gly Gly Lys Asn Thr Met Met
                740                 745                 750

Arg Ser His Gly Val Ser Val Leu Gly Ile Phe Asn Leu Glu Lys Asp
            755                 760                 765

Asp Met Leu Tyr Ile Leu Val Gly Gln Gln Gly Glu Asp Ala Cys Pro
    770                 775                 780

Ser Thr Asn Gln Leu Ile Gln Lys Val Cys Ile Gly Glu Asn Asn Val
785                 790                 795                 800

Ile Glu Glu Glu Ile Arg Val Asn Arg Ser Val His Glu Trp Ala Gly
            805                 810                 815

Gly Gly Gly Gly Gly Gly Ala Thr Tyr Val Phe Lys Met Lys Asp
            820                 825                 830

Gly Val Pro Val Pro Leu Ile Ile Ala Ala Gly Gly Gly Gly Arg Ala
            835                 840                 845

Tyr Gly Ala Lys Thr Asp Thr Phe His Pro Glu Arg Leu Glu Asn Asn
    850                 855                 860

Ser Ser Val Leu Gly Leu Asn Gly Asn Ser Gly Ala Ala Gly Gly Gly
865                 870                 875                 880

Gly Gly Trp Asn Asp Asn Thr Ser Leu Leu Trp Ala Gly Lys Ser Leu
            885                 890                 895

Gln Glu Gly Ala Thr Gly Gly His Ser Cys Pro Gln Ala Met Lys Lys
            900                 905                 910

Trp Gly Trp Glu Thr Arg Gly Gly Phe Gly Gly Gly Gly Gly Cys
            915                 920                 925

Ser Ser Gly Gly Gly Gly Gly Tyr Ile Gly Gly Asn Ala Ala Ser
930                 935                 940

Asn Asn Asp Pro Glu Met Asp Gly Glu Asp Gly Val Ser Phe Ile Ser
945                 950                 955                 960

Pro Leu Gly Ile Leu Tyr Thr Pro Ala Leu Lys Val Met Glu Gly His
            965                 970                 975

Gly Glu Val Asn Ile Lys His Tyr Leu Asn Cys Ser His Cys Glu Val
            980                 985                 990

Asp Glu Cys His Met Asp Pro Glu   Ser His Lys Val Ile Cys Phe Cys
            995                 1000                 1005

Asp His Gly Thr Val Leu Ala   Glu Asp Gly Val Ser   Cys Ile Val
            1010                1015                 1020

Ser Pro Thr Pro Glu Pro His   Leu Pro Leu Ser Leu   Ile Leu Ser
            1025                1030                 1035

Val Val  Thr Ser Ala Leu Val   Ala Ala Leu Val Leu   Ala Phe Ser
            1040                1045                 1050

Gly Ile  Met Ile Val Tyr Arg   Arg Lys His Gln Glu   Leu Gln Ala
            1055                1060                 1065

Met Gln  Met Glu Leu Gln Ser   Pro Glu Tyr Lys Leu   Ser Lys Leu
            1070                1075                 1080

Arg Thr  Ser Thr Ile Met Thr   Asp Tyr Asn Pro Asn   Tyr Cys Phe
```

-continued

```
              1085                1090                 1095

Ala Gly Lys Thr Ser Ser Ile Ser Asp Leu Lys Glu Val Pro Arg
1100                1105                1110

Lys Asn Ile Thr Leu Ile Arg Gly Leu Gly His Gly Ala Phe Gly
1115                1120                1125

Glu Val Tyr Glu Gly Gln Val Ser Gly Met Pro Asn Asp Pro Ser
1130                1135                1140

Pro Leu Gln Val Ala Val Lys Thr Leu Pro Glu Val Cys Ser Glu
1145                1150                1155

Gln Asp Glu Leu Asp Phe Leu Met Glu Ala Leu Ile Ile Ser Lys
1160                1165                1170

Phe Asn His Gln Asn Ile Val Arg Cys Ile Gly Val Ser Leu Gln
1175                1180                1185

Ser Leu Pro Arg Phe Ile Leu Leu Glu Leu Met Ala Gly Gly Asp
1190                1195                1200

Leu Lys Ser Phe Leu Arg Glu Thr Arg Pro Arg Pro Ser Gln Pro
1205                1210                1215

Ser Ser Leu Ala Met Leu Asp Leu Leu His Val Ala Arg Asp Ile
1220                1225                1230

Ala Cys Gly Cys Gln Tyr Leu Glu Glu Asn His Phe Ile His Arg
1235                1240                1245

Asp Ile Ala Ala Arg Asn Cys Leu Leu Thr Cys Pro Gly Pro Gly
1250                1255                1260

Arg Val Ala Lys Ile Gly Asp Phe Gly Met Ala Arg Asp Ile Tyr
1265                1270                1275

Arg Ala Ser Tyr Tyr Arg Lys Gly Gly Cys Ala Met Leu Pro Val
1280                1285                1290

Lys Trp Met Pro Pro Glu Ala Phe Met Glu Gly Ile Phe Thr Ser
1295                1300                1305

Lys Thr Asp Thr Trp Ser Phe Gly Val Leu Leu Trp Glu Ile Phe
1310                1315                1320

Ser Leu Gly Tyr Met Pro Tyr Pro Ser Lys Ser Asn Gln Glu Val
1325                1330                1335

Leu Glu Phe Val Thr Ser Gly Gly Arg Met Asp Pro Pro Lys Asn
1340                1345                1350

Cys Pro Gly Pro Val Tyr Arg Ile Met Thr Gln Cys Trp Gln His
1355                1360                1365

Gln Pro Glu Asp Arg Pro Asn Phe Ala Ile Ile Leu Glu Arg Ile
1370                1375                1380

Glu Tyr Cys Thr Gln Asp Pro Asp Val Ile Asn Thr Ala Leu Pro
1385                1390                1395

Ile Glu Tyr Gly Pro Leu Val Glu Glu Glu Glu Lys Val Pro Val
1400                1405                1410

Arg Pro Lys Asp Pro Glu Gly Val Pro Pro Leu Leu Val Ser Gln
1415                1420                1425

Gln Ala Lys Arg Glu Glu Glu Arg Ser Pro Ala Ala Pro Pro Pro
1430                1435                1440

Leu Pro Thr Thr Ser Ser Gly Lys Ala Ala Lys Lys Pro Thr Ala
1445                1450                1455

Ala Glu Val Ser Val Arg Val Pro Arg Gly Pro Ala Val Glu Gly
1460                1465                1470

Gly His Val Asn Met Ala Phe Ser Gln Ser Asn Pro Pro Ser Glu
1475                1480                1485
```

-continued

```
Leu His Lys Val His Gly Ser Arg Asn Lys Pro Thr Ser Leu Trp
    1490                1495                1500

Asn Pro Thr Tyr Gly Ser Trp Phe Thr Glu Lys Pro Thr Lys Lys
    1505                1510                1515

Asn Asn Pro Ile Ala Lys Lys Glu Pro His Asp Arg Gly Asn Leu
    1520                1525                1530

Gly Leu Glu Gly Ser Cys Thr Val Pro Pro Asn Val Ala Thr Gly
    1535                1540                1545

Arg Leu Pro Gly Ala Ser Leu Leu Leu Glu Pro Ser Ser Leu Thr
    1550                1555                1560

Ala Asn Met Lys Glu Val Pro Leu Phe Arg Leu Arg His Phe Pro
    1565                1570                1575

Cys Gly Asn Val Asn Tyr Gly Tyr Gln Gln Gln Gly Leu Pro Leu
    1580                1585                1590

Glu Ala Ala Thr Ala Pro Gly Ala Gly His Tyr Glu Asp Thr Ile
    1595                1600                1605

Leu Lys Ser Lys Asn Ser Met Asn Gln Pro Gly Pro
    1610                1615                1620

<210> SEQ ID NO 3
<211> LENGTH: 2442
<212> TYPE: DNA
<213> ORGANISM: Homo sapiens
<220> FEATURE:
<221> NAME/KEY: CDS
<222> LOCATION: (74)..(2113)
<221> NAME/KEY: mat_peptide
<222> LOCATION: (74)..(2113)

<400> SEQUENCE: 3
cggttgttct ctggagcagc gttcttttat ctccgtccgc cttctctcct acctaagtgc    60
gtgccgccac ccg atg gaa gat tcg atg gac atg gac atg agc ccc ctg      109
            Met Glu Asp Ser Met Asp Met Asp Met Ser Pro Leu
              1               5                   10 agg ccc cag aac tat ctt ttc ggt tgt gaa cta aag gcc gac aaa gat    157
Arg Pro Gln Asn Tyr Leu Phe Gly Cys Glu Leu Lys Ala Asp Lys Asp
            15                  20                  25 tat cac ttt aag gtg gat aat gat gaa aat gag cac cag tta tct tta    205
Tyr His Phe Lys Val Asp Asn Asp Glu Asn Glu His Gln Leu Ser Leu
    30                  35                  40 aga acg gtc agt tta ggg gct ggt gca aag gat gag ttg cac att gtt    253
Arg Thr Val Ser Leu Gly Ala Gly Ala Lys Asp Glu Leu His Ile Val
45                  50                  55                  60 gaa gca gag gca atg aat tac gaa ggc agt cca att aaa gta aca ctg    301
Glu Ala Glu Ala Met Asn Tyr Glu Gly Ser Pro Ile Lys Val Thr Leu
                65                  70                  75 gca act ttg aaa atg tct gta cag cca acg gtt tcc ctt ggg ggc ttt    349
Ala Thr Leu Lys Met Ser Val Gln Pro Thr Val Ser Leu Gly Gly Phe
            80                  85                  90 gaa ata aca cca cca gtg gtc tta agg ttg aag tgt ggt tca ggg cca    397
Glu Ile Thr Pro Pro Val Val Leu Arg Leu Lys Cys Gly Ser Gly Pro
        95                  100                 105 gtg cat att agt gga cag cac tta gta gtg tac cgc cgg aag cac cag    445
Val His Ile Ser Gly Gln His Leu Val Val Tyr Arg Arg Lys His Gln
    110                 115                 120 gag ctg caa gcc atg cag atg gag ctg cag agc cct gag tac aag ctg    493
Glu Leu Gln Ala Met Gln Met Glu Leu Gln Ser Pro Glu Tyr Lys Leu
125                 130                 135                 140
```

-continued

| | | |
|---|---|---|
| agc aag ctc cgc acc tcg acc atc atg acc gac tac aac ccc aac tac<br>Ser Lys Leu Arg Thr Ser Thr Ile Met Thr Asp Tyr Asn Pro Asn Tyr<br>                145                  150                 155 | 541 |
| tgc ttt gct ggc aag acc tcc tcc atc agt gac ctg aag gag gtg ccg<br>Cys Phe Ala Gly Lys Thr Ser Ser Ile Ser Asp Leu Lys Glu Val Pro<br>           160                  165                  170 | 589 |
| cgg aaa aac atc acc ctc att cgg ggt ctg ggc cat ggc gcc ttt ggg<br>Arg Lys Asn Ile Thr Leu Ile Arg Gly Leu Gly His Gly Ala Phe Gly<br>        175                   180                  185 | 637 |
| gag gtg tat gaa ggc cag gtg tcc gga atg ccc aac gac cca agc ccc<br>Glu Val Tyr Glu Gly Gln Val Ser Gly Met Pro Asn Asp Pro Ser Pro<br>          190                  195                  200 | 685 |
| ctg caa gtg gct gtg aag acg ctg cct gaa gtg tgc tct gaa cag gac<br>Leu Gln Val Ala Val Lys Thr Leu Pro Glu Val Cys Ser Glu Gln Asp<br>205                   210                  215                  220 | 733 |
| gaa ctg gat ttc ctc atg gaa gcc ctg atc atc agc aaa ttc aac cac<br>Glu Leu Asp Phe Leu Met Glu Ala Leu Ile Ile Ser Lys Phe Asn His<br>                  225                  230                  235 | 781 |
| cag aac att gtt cgc tgc att ggg gtg agc ctg caa tcc ctg ccc cgg<br>Gln Asn Ile Val Arg Cys Ile Gly Val Ser Leu Gln Ser Leu Pro Arg<br>        240                   245                  250 | 829 |
| ttc atc ctg ctg gag ctc atg gcg ggg gga gac ctc aag tcc ttc ctc<br>Phe Ile Leu Leu Glu Leu Met Ala Gly Gly Asp Leu Lys Ser Phe Leu<br>          255                  260                  265 | 877 |
| cga gag acc cgc cct cgc ccg agc cag ccc tcc tcc ctg gcc atg ctg<br>Arg Glu Thr Arg Pro Arg Pro Ser Gln Pro Ser Ser Leu Ala Met Leu<br>          270                  275                  280 | 925 |
| gac ctt ctg cac gtg gct cgg gac att gcc tgt ggc tgt cag tat ttg<br>Asp Leu Leu His Val Ala Arg Asp Ile Ala Cys Gly Cys Gln Tyr Leu<br>285                   290                  295                  300 | 973 |
| gag gaa aac cac ttc atc cac cga gac att gct gcc aga aac tgc ctc<br>Glu Glu Asn His Phe Ile His Arg Asp Ile Ala Ala Arg Asn Cys Leu<br>                  305                  310                  315 | 1021 |
| ttg acc tgt cca ggc cct gga aga gtg gcc aag att gga gac ttc ggg<br>Leu Thr Cys Pro Gly Pro Gly Arg Val Ala Lys Ile Gly Asp Phe Gly<br>        320                   325                  330 | 1069 |
| atg gcc cga gac atc tac agg gcg agc tac tat aga aag gga ggc tgt<br>Met Ala Arg Asp Ile Tyr Arg Ala Ser Tyr Tyr Arg Lys Gly Gly Cys<br>          335                  340                  345 | 1117 |
| gcc atg ctg cca gtt aag tgg atg ccc cca gag gcc ttc atg gaa gga<br>Ala Met Leu Pro Val Lys Trp Met Pro Pro Glu Ala Phe Met Glu Gly<br>        350                   355                  360 | 1165 |
| ata ttc act tct aaa aca gac aca tgg tcc ttt gga gtg ctg cta tgg<br>Ile Phe Thr Ser Lys Thr Asp Thr Trp Ser Phe Gly Val Leu Leu Trp<br>365                   370                  375                  380 | 1213 |
| gaa atc ttt tct ctt gga tat atg cca tac ccc agc aaa agc aac cag<br>Glu Ile Phe Ser Leu Gly Tyr Met Pro Tyr Pro Ser Lys Ser Asn Gln<br>                  385                  390                  395 | 1261 |
| gaa gtt ctg gag ttt gtc acc agt gga ggc cgg atg gac cca ccc aag<br>Glu Val Leu Glu Phe Val Thr Ser Gly Gly Arg Met Asp Pro Pro Lys<br>          400                  405                  410 | 1309 |
| aac tgc cct ggg cct gta tac cgg ata atg act cag tgc tgg caa cat<br>Asn Cys Pro Gly Pro Val Tyr Arg Ile Met Thr Gln Cys Trp Gln His<br>        415                   420                  425 | 1357 |
| cag cct gaa gac agg ccc aac ttt gcc atc att ttg gag agg att gaa<br>Gln Pro Glu Asp Arg Pro Asn Phe Ala Ile Ile Leu Glu Arg Ile Glu<br>          430                  435                  440 | 1405 |
| tac tgc acc cag gac ccg gat gta atc aac acc gct ttg ccg ata gaa<br>Tyr Cys Thr Gln Asp Pro Asp Val Ile Asn Thr Ala Leu Pro Ile Glu<br>445                   450                  455                  460 | 1453 |

-continued

| | | |
|---|---|---|
| tat ggt cca ctt gtg gaa gag gaa gag aaa gtg cct gtg agg ccc aag<br>Tyr Gly Pro Leu Val Glu Glu Glu Glu Lys Val Pro Val Arg Pro Lys<br>               465                         470                       475 | 1501 |

```
tat ggt cca ctt gtg gaa gag gaa gag aaa gtg cct gtg agg ccc aag     1501
Tyr Gly Pro Leu Val Glu Glu Glu Glu Lys Val Pro Val Arg Pro Lys
                465                 470                 475 gac cct gag ggg gtt cct cct ctc ctg gtc tct caa cag gca aaa cgg     1549
Asp Pro Glu Gly Val Pro Pro Leu Leu Val Ser Gln Gln Ala Lys Arg
            480                 485                 490 gag gag gag cgc agc cca gct gcc cca cca cct ctg cct acc acc tcc     1597
Glu Glu Glu Arg Ser Pro Ala Ala Pro Pro Leu Pro Thr Thr Ser
        495                 500                 505 tct ggc aag gct gca aag aaa ccc aca gct gca gag gtc tct gtt cga     1645
Ser Gly Lys Ala Ala Lys Lys Pro Thr Ala Ala Glu Val Ser Val Arg
    510                 515                 520 gtc cct aga ggg ccg gcc gtg gaa ggg gga cac gtg aat atg gca ttc     1693
Val Pro Arg Gly Pro Ala Val Glu Gly Gly His Val Asn Met Ala Phe
525                 530                 535                 540 tct cag tcc aac cct cct tcg gag ttg cac aag gtc cac gga tcc aga     1741
Ser Gln Ser Asn Pro Pro Ser Glu Leu His Lys Val His Gly Ser Arg
                545                 550                 555 aac aag ccc acc agc ttg tgg aac cca acg tac ggc tcc tgg ttt aca     1789
Asn Lys Pro Thr Ser Leu Trp Asn Pro Thr Tyr Gly Ser Trp Phe Thr
            560                 565                 570 gag aaa ccc acc aaa aag aat aat cct ata gca aag aag gag cca cac     1837
Glu Lys Pro Thr Lys Lys Asn Asn Pro Ile Ala Lys Lys Glu Pro His
        575                 580                 585 gac agg ggt aac ctg ggg ctg gag gga agc tgt act gtc cca cct aac     1885
Asp Arg Gly Asn Leu Gly Leu Glu Gly Ser Cys Thr Val Pro Pro Asn
    590                 595                 600 gtt gca act ggg aga ctt ccg ggg gcc tca ctg ctc cta gag ccc tct     1933
Val Ala Thr Gly Arg Leu Pro Gly Ala Ser Leu Leu Leu Glu Pro Ser
605                 610                 615                 620 tcg ctg act gcc aat atg aag gag gta cct ctg ttc agg cta cgt cac     1981
Ser Leu Thr Ala Asn Met Lys Glu Val Pro Leu Phe Arg Leu Arg His
                625                 630                 635 ttc cct tgt ggg aat gtc aat tac ggc tac cag caa cag ggc ttg ccc     2029
Phe Pro Cys Gly Asn Val Asn Tyr Gly Tyr Gln Gln Gln Gly Leu Pro
            640                 645                 650 tta gaa gcc gct act gcc cct gga gct ggt cat tac gag gat acc att     2077
Leu Glu Ala Ala Thr Ala Pro Gly Ala Gly His Tyr Glu Asp Thr Ile
        655                 660                 665 ctg aaa agc aag aat agc atg aac cag cct ggg ccc tgagctcggt          2123
Leu Lys Ser Lys Asn Ser Met Asn Gln Pro Gly Pro
    670                 675                 680 cgcacactca cttctcttcc ttgggatccc taagaccgtg gaggagagag aggcaatggc   2183
tccttcacaa accagagacc aaatgtcacg ttttgttttg tgccaaccta ttttgaagta   2243
ccaccaaaaa agctgtattt tgaaatgct  ttagaaaggt tttgagcatg ggttcatcct   2303
attctttcga aagaagaaaa tatcataaaa atgagtgata aatacaaggc ccagatgtgg   2363
ttgcataagg ttttatgca tgtttgttgt atacttcctt atgcttcttt taaattgtgt    2423
gtgctctgct tcaatctag                                                2442

<210> SEQ ID NO 4
<211> LENGTH: 680
<212> TYPE: PRT
<213> ORGANISM: Homo sapiens

<400> SEQUENCE: 4

Met Glu Asp Ser Met Asp Met Asp Met Ser Pro Leu Arg Pro Gln Asn
1               5                   10                  15
```

-continued

```
Tyr Leu Phe Gly Cys Glu Leu Lys Ala Asp Lys Asp Tyr His Phe Lys
             20                  25                  30

Val Asp Asn Asp Glu Asn Glu His Gln Leu Ser Leu Arg Thr Val Ser
             35                  40                  45

Leu Gly Ala Gly Ala Lys Asp Glu Leu His Ile Val Glu Ala Glu Ala
         50                  55                  60

Met Asn Tyr Glu Gly Ser Pro Ile Lys Val Thr Leu Ala Thr Leu Lys
65                      70                  75                  80

Met Ser Val Gln Pro Thr Val Ser Leu Gly Gly Phe Glu Ile Thr Pro
                 85                  90                  95

Pro Val Val Leu Arg Leu Lys Cys Gly Ser Gly Pro Val His Ile Ser
                100                 105                 110

Gly Gln His Leu Val Val Tyr Arg Arg Lys His Gln Glu Leu Gln Ala
            115                 120                 125

Met Gln Met Glu Leu Gln Ser Pro Glu Tyr Lys Leu Ser Lys Leu Arg
        130                 135                 140

Thr Ser Thr Ile Met Thr Asp Tyr Asn Pro Asn Tyr Cys Phe Ala Gly
145                 150                 155                 160

Lys Thr Ser Ser Ile Ser Asp Leu Lys Glu Val Pro Arg Lys Asn Ile
                165                 170                 175

Thr Leu Ile Arg Gly Leu Gly His Gly Ala Phe Gly Glu Val Tyr Glu
                180                 185                 190

Gly Gln Val Ser Gly Met Pro Asn Asp Pro Ser Pro Leu Gln Val Ala
            195                 200                 205

Val Lys Thr Leu Pro Glu Val Cys Ser Glu Gln Asp Glu Leu Asp Phe
        210                 215                 220

Leu Met Glu Ala Leu Ile Ile Ser Lys Phe Asn His Gln Asn Ile Val
225                 230                 235                 240

Arg Cys Ile Gly Val Ser Leu Gln Ser Leu Pro Arg Phe Ile Leu Leu
                245                 250                 255

Glu Leu Met Ala Gly Gly Asp Leu Lys Ser Phe Leu Arg Glu Thr Arg
            260                 265                 270

Pro Arg Pro Ser Gln Pro Ser Ser Leu Ala Met Leu Asp Leu Leu His
        275                 280                 285

Val Ala Arg Asp Ile Ala Cys Gly Cys Gln Tyr Leu Glu Glu Asn His
    290                 295                 300

Phe Ile His Arg Asp Ile Ala Ala Arg Asn Cys Leu Leu Thr Cys Pro
305                 310                 315                 320

Gly Pro Gly Arg Val Ala Lys Ile Gly Asp Phe Gly Met Ala Arg Asp
                325                 330                 335

Ile Tyr Arg Ala Ser Tyr Tyr Arg Lys Gly Gly Cys Ala Met Leu Pro
            340                 345                 350

Val Lys Trp Met Pro Pro Glu Ala Phe Met Glu Gly Ile Phe Thr Ser
        355                 360                 365

Lys Thr Asp Thr Trp Ser Phe Gly Val Leu Leu Trp Glu Ile Phe Ser
    370                 375                 380

Leu Gly Tyr Met Pro Tyr Pro Ser Lys Ser Asn Gln Glu Val Leu Glu
385                 390                 395                 400

Phe Val Thr Ser Gly Gly Arg Met Asp Pro Pro Lys Asn Cys Pro Gly
                405                 410                 415

Pro Val Tyr Arg Ile Met Thr Gln Cys Trp Gln His Gln Pro Glu Asp
            420                 425                 430
```

```
Arg Pro Asn Phe Ala Ile Ile Leu Glu Arg Ile Glu Tyr Cys Thr Gln
        435                 440                 445

Asp Pro Asp Val Ile Asn Thr Ala Leu Pro Ile Glu Tyr Gly Pro Leu
    450                 455                 460

Val Glu Glu Glu Lys Val Pro Val Arg Pro Lys Asp Pro Glu Gly
465                 470                 475                 480

Val Pro Pro Leu Leu Val Ser Gln Gln Ala Lys Arg Glu Glu Arg
                485                 490                 495

Ser Pro Ala Ala Pro Pro Leu Pro Thr Thr Ser Ser Gly Lys Ala
        500                 505                 510

Ala Lys Lys Pro Thr Ala Ala Glu Val Ser Val Arg Val Pro Arg Gly
        515                 520                 525

Pro Ala Val Glu Gly Gly His Val Asn Met Ala Phe Ser Gln Ser Asn
        530                 535                 540

Pro Pro Ser Glu Leu His Lys Val His Gly Ser Arg Asn Lys Pro Thr
545                 550                 555                 560

Ser Leu Trp Asn Pro Thr Tyr Gly Ser Trp Phe Thr Glu Lys Pro Thr
                565                 570                 575

Lys Lys Asn Asn Pro Ile Ala Lys Lys Glu Pro His Asp Arg Gly Asn
                580                 585                 590

Leu Gly Leu Glu Gly Ser Cys Thr Val Pro Pro Asn Val Ala Thr Gly
        595                 600                 605

Arg Leu Pro Gly Ala Ser Leu Leu Glu Pro Ser Ser Leu Thr Ala
        610                 615                 620

Asn Met Lys Glu Val Pro Leu Phe Arg Leu Arg His Phe Pro Cys Gly
625                 630                 635                 640

Asn Val Asn Tyr Gly Tyr Gln Gln Gln Gly Leu Pro Leu Glu Ala Ala
                645                 650                 655

Thr Ala Pro Gly Ala Gly His Tyr Glu Asp Thr Ile Leu Lys Ser Lys
        660                 665                 670

Asn Ser Met Asn Gln Pro Gly Pro
        675                 680

<210> SEQ ID NO 5
<211> LENGTH: 26
<212> TYPE: DNA
<213> ORGANISM: synthetic construct

<400> SEQUENCE: 5
tcccttgggg gctttgaaat aacacc                                    26

<210> SEQ ID NO 6
<211> LENGTH: 22
<212> TYPE: DNA
<213> ORGANISM: synthetic construct

<400> SEQUENCE: 6
gctgagcaag ctccgcacct cg                                        22

<210> SEQ ID NO 7
<211> LENGTH: 100
<212> TYPE: PRT
<213> ORGANISM: Homo sapiens

<400> SEQUENCE: 7

Val Asn Ile Lys His Tyr Leu Asn Cys Ser His Cys Glu Val Asp Glu
1               5                   10                  15
```

Cys His Met Asp Pro Glu Ser His Lys Val Ile Cys Phe Cys Asp His
            20                  25                  30

Gly Thr Val Leu Ala Glu Asp Gly Val Ser Cys Ile Val Ser Pro Thr
            35                  40                  45

Pro Glu Pro His Leu Pro Leu Ser Leu Ile Leu Ser Val Val Thr Ser
50                  55                  60

Ala Leu Val Ala Ala Leu Val Leu Ala Phe Ser Gly Ile Met Ile Val
65                  70                  75                  80

Tyr Arg Arg Lys His Gln Glu Leu Gln Ala Met Gln Met Glu Leu Gln
                85                  90                  95

Ser Pro Glu Tyr
            100

<210> SEQ ID NO 8
<211> LENGTH: 21
<212> TYPE: DNA
<213> ORGANISM: synthetic construct

<400> SEQUENCE: 8
gctaccacct ccagggcag a                                          21

<210> SEQ ID NO 9
<211> LENGTH: 24
<212> TYPE: DNA
<213> ORGANISM: synthetic construct

<400> SEQUENCE: 9
agcacttagt agctgtggag gaag                                      24

<210> SEQ ID NO 10
<211> LENGTH: 24
<212> TYPE: DNA
<213> ORGANISM: synthetic construct

<400> SEQUENCE: 10
agcacttagt agtgtaccgc cgga                                      24

<210> SEQ ID NO 11
<211> LENGTH: 186
<212> TYPE: DNA
<213> ORGANISM: Homo sapiens

<400> SEQUENCE: 11
taccgtcgga agcaccagga gttgcaggct atgcagatgg aactgcagag ccccgagtat    60
aagctgagca agctacggac ctcgaccatc atgaccgact acaacccaa ctactgcttc   120 gctggcaaga cttcctccat cagtgacctg aaagaagtgc acggaaaaa catcacactc   180 atccgg                                                             186

<210> SEQ ID NO 12
<211> LENGTH: 22
<212> TYPE: PRT
<213> ORGANISM: Homo sapiens

<400> SEQUENCE: 12

Leu Gly His Gly Ala Phe Gly Glu Val Tyr Glu Gly Gln Val Ser Gly
1               5                   10                  15

Met Pro Asn Asp Pro Ser
            20

```
<210> SEQ ID NO 13
<211> LENGTH: 72
<212> TYPE: PRT
<213> ORGANISM: Homo sapiens

<400> SEQUENCE: 13

Pro Leu Gln Val Ala Val Lys Thr Leu Pro Glu Val Cys Ser Glu Gln
1               5                   10                  15

Asp Glu Leu Asp Phe Leu Met Glu Ala Leu Ile Ile Ser Lys Phe Asn
            20                  25                  30

His Gln Asn Ile Val Arg Cys Ile Gly Val Ser Leu Gln Ser Leu Pro
        35                  40                  45

Arg Phe Ile Leu Leu Glu Leu Met Ala Gly Gly Asp Leu Lys Ser Phe
    50                  55                  60

Leu Arg Glu Thr Arg Pro Arg Pro
65                  70

<210> SEQ ID NO 14
<211> LENGTH: 45
<212> TYPE: PRT
<213> ORGANISM: Homo sapiens

<400> SEQUENCE: 14

Ser Gln Pro Ser Ser Leu Ala Met Leu Asp Leu Leu His Val Ala Arg
1               5                   10                  15

Asp Ile Ala Cys Gly Cys Gln Tyr Leu Glu Glu Asn His Phe Ile His
            20                  25                  30

Arg Asp Ile Ala Ala Arg Asn Cys Leu Leu Thr Cys Pro
        35                  40                  45

<210> SEQ ID NO 15
<211> LENGTH: 116
<212> TYPE: PRT
<213> ORGANISM: Homo sapiens

<400> SEQUENCE: 15

Gly Pro Gly Arg Val Ala Lys Ile Gly Asp Phe Gly Met Ala Arg Asp
1               5                   10                  15

Ile Tyr Arg Ala Ser Tyr Tyr Arg Lys Gly Gly Cys Ala Met Leu Pro
            20                  25                  30

Val Lys Trp Met Pro Pro Glu Ala Phe Met Glu Gly Ile Phe Thr Ser
        35                  40                  45

Lys Thr Asp Thr Trp Ser Phe Gly Val Leu Leu Trp Glu Ile Phe Ser
    50                  55                  60

Leu Gly Tyr Met Pro Tyr Pro Ser Lys Ser Asn Gln Glu Val Leu Glu
65                  70                  75                  80

Phe Val Thr Ser Gly Gly Arg Met Asp Pro Pro Lys Asn Cys Pro Gly
            85                  90                  95

Pro Val Tyr Arg Ile Met Thr Gln Cys Trp Gln His Gln Pro Glu Asp
        100                 105                 110

Arg Pro Asn Phe
    115

<210> SEQ ID NO 16
<211> LENGTH: 22
<212> TYPE: PRT
<213> ORGANISM: Homo sapiens

<400> SEQUENCE: 16
```

```
Leu Gly His Gly Ala Phe Gly Glu Val Tyr Glu Gly Leu Val Ile Gly
1               5                   10                  15

Leu Pro Gly Asp Ser Ser
                20

<210> SEQ ID NO 17
<211> LENGTH: 72
<212> TYPE: PRT
<213> ORGANISM: Homo sapiens

<400> SEQUENCE: 17

Pro Leu Gln Val Ala Ile Lys Thr Leu Pro Glu Leu Cys Ser Pro Gln
1               5                   10                  15

Asp Glu Leu Asp Phe Leu Met Glu Ala Leu Ile Ile Ser Lys Phe Arg
                20                  25                  30

His Gln Asn Ile Val Arg Cys Val Gly Leu Ser Leu Arg Ala Thr Pro
            35                  40                  45

Arg Leu Ile Leu Leu Glu Leu Met Ser Gly Gly Asp Met Lys Ser Phe
        50                  55                  60

Leu Arg His Ser Arg Pro His Leu
65                  70

<210> SEQ ID NO 18
<211> LENGTH: 45
<212> TYPE: PRT
<213> ORGANISM: Homo sapiens

<400> SEQUENCE: 18

Gly Gln Pro Ser Pro Leu Val Met Arg Asp Leu Leu Gln Leu Ala Gln
1               5                   10                  15

Asp Ile Ala Gln Gly Cys His Tyr Leu Glu Glu Asn His Phe Ile His
                20                  25                  30

Arg Asp Ile Ala Ala Arg Asn Cys Leu Leu Ser Cys Ala
            35                  40                  45

<210> SEQ ID NO 19
<211> LENGTH: 116
<212> TYPE: PRT
<213> ORGANISM: Homo sapiens

<400> SEQUENCE: 19

Gly Pro Ser Arg Val Ala Lys Ile Gly Asp Phe Gly Met Ala Arg Asp
1               5                   10                  15

Ile Tyr Arg Ala Ser Tyr Tyr Arg Arg Gly Asp Arg Ala Leu Leu Pro
                20                  25                  30

Val Lys Trp Met Pro Pro Glu Ala Phe Leu Glu Gly Ile Phe Thr Ser
            35                  40                  45

Lys Thr Asp Ser Trp Ser Phe Gly Val Leu Leu Trp Glu Ile Phe Ser
        50                  55                  60

Leu Gly Tyr Met Pro Tyr Pro Gly Arg Thr Asn Gln Glu Val Leu Asp
65                  70                  75                  80

Phe Val Val Gly Gly Gly Arg Met Asp Pro Pro Arg Gly Cys Pro Gly
                85                  90                  95

Pro Val Tyr Arg Ile Met Thr Gln Cys Trp Gln His Glu Pro Glu Leu
                100                 105                 110

Arg Pro Ser Phe
            115
```

```
<210> SEQ ID NO 20
<211> LENGTH: 22
<212> TYPE: PRT
<213> ORGANISM: Homo sapiens

<400> SEQUENCE: 20

Leu Gly Glu Gly Ala Phe Gly Lys Val Phe Leu Ala Glu Cys His Asn
1               5                   10                  15

Leu Leu Pro Glu Gln Asp
            20

<210> SEQ ID NO 21
<211> LENGTH: 11
<212> TYPE: PRT
<213> ORGANISM: Homo sapiens

<400> SEQUENCE: 21

Lys Met Leu Val Ala Val Lys Ala Leu Lys Glu
1               5                   10

<210> SEQ ID NO 22
<211> LENGTH: 110
<212> TYPE: PRT
<213> ORGANISM: Homo sapiens

<400> SEQUENCE: 22

Ala Ser Glu Ser Ala Arg Gln Asp Phe Gln Arg Glu Ala Glu Leu Leu
1               5                   10                  15

Thr Met Leu Gln His Gln His Ile Val Arg Phe Phe Gly Val Cys Thr
            20                  25                  30

Glu Gly Arg Pro Leu Leu Met Val Phe Glu Tyr Met Arg His Gly Asp
        35                  40                  45

Leu Asn Arg Phe Leu Arg Ser His Gly Pro Asp Ala Lys Leu Leu Ala
    50                  55                  60

Gly Gly Glu Asp Val Ala Pro Gly Pro Leu Gly Leu Gly Gln Leu Leu
65                  70                  75                  80

Ala Val Ala Ser Gln Val Ala Ala Gly Met Val Tyr Leu Ala Gly Leu
                85                  90                  95

His Phe Val His Arg Asp Leu Ala Thr Arg Asn Cys Leu Val
            100                 105                 110

<210> SEQ ID NO 23
<211> LENGTH: 116
<212> TYPE: PRT
<213> ORGANISM: Homo sapiens

<400> SEQUENCE: 23

Gly Gln Gly Leu Val Val Lys Ile Gly Asp Phe Gly Met Ser Arg Asp
1               5                   10                  15

Ile Tyr Ser Thr Asp Tyr Tyr Arg Val Gly Gly Arg Thr Met Leu Pro
            20                  25                  30

Ile Arg Trp Met Pro Pro Glu Ser Ile Leu Tyr Arg Lys Phe Thr Thr
        35                  40                  45

Glu Ser Asp Val Trp Ser Phe Gly Val Val Leu Trp Glu Ile Phe Thr
    50                  55                  60

Tyr Gly Lys Gln Pro Trp Tyr Gln Leu Ser Asn Thr Glu Ala Ile Asp
65                  70                  75                  80

Cys Ile Thr Gln Gly Arg Glu Leu Glu Arg Pro Arg Ala Cys Pro Pro
                85                  90                  95
```

```
Glu Val Tyr Ala Ile Met Arg Gly Cys Trp Gln Arg Glu Pro Gln Gln
                100                 105                 110

Arg His Ser Ile
        115

<210> SEQ ID NO 24
<211> LENGTH: 98
<212> TYPE: PRT
<213> ORGANISM: Homo sapiens

<400> SEQUENCE: 24

Leu Gly Ser Gly Ala Phe Gly Glu Val Val Tyr Glu Gly Thr Ala Val
1               5                   10                  15

Asp Ile Leu Gly Val Gly Ser Gly Glu Ile Lys Val Ala Val Lys Thr
            20                  25                  30

Leu Lys Lys Gly Ser Thr Asp Gln Glu Lys Ile Glu Phe Leu Lys Glu
        35                  40                  45

Ala His Leu Met Ser Lys Phe Asn His Pro Asn Ile Leu Lys Gln Leu
    50                  55                  60

Gly Val Cys Leu Leu Asn Glu Pro Gln Tyr Ile Ile Leu Glu Leu Met
65                  70                  75                  80

Glu Gly Gly Asp Leu Leu Thr Tyr Leu Arg Lys Ala Arg Met Ala Thr
                85                  90                  95

Phe Tyr

<210> SEQ ID NO 25
<211> LENGTH: 40
<212> TYPE: PRT
<213> ORGANISM: Homo sapiens

<400> SEQUENCE: 25

Pro Leu Leu Thr Leu Val Asp Leu Val Asp Leu Cys Val Asp Ile Ser
1               5                   10                  15

Lys Gly Cys Val Tyr Leu Glu Arg Met His Phe Ile His Arg Asp Leu
            20                  25                  30

Ala Ala Arg Asn Cys Leu Val Ser
        35                  40

<210> SEQ ID NO 26
<211> LENGTH: 120
<212> TYPE: PRT
<213> ORGANISM: Homo sapiens

<400> SEQUENCE: 26

Val Lys Asp Tyr Thr Ser Pro Arg Ile Val Lys Ile Gly Asp Phe Gly
1               5                   10                  15

Leu Ala Arg Asp Ile Tyr Lys Asn Asp Tyr Tyr Arg Lys Arg Gly Glu
            20                  25                  30

Gly Leu Leu Pro Val Arg Trp Met Ala Pro Glu Ser Leu Met Asp Gly
        35                  40                  45

Ile Phe Thr Thr Gln Ser Asp Val Trp Ser Phe Gly Ile Leu Ile Trp
    50                  55                  60

Glu Ile Leu Thr Leu Gly His Gln Pro Tyr Pro Ala His Ser Asn Leu
65                  70                  75                  80

Asp Val Leu Asn Tyr Val Gln Thr Gly Gly Arg Leu Glu Pro Pro Arg
                85                  90                  95

Asn Cys Pro Asp Asp Leu Trp Asn Leu Met Thr Gln Cys Trp Ala Gln
                100                 105                 110
```

```
Glu Pro Asp Gln Arg Pro Thr Phe
        115                 120

<210> SEQ ID NO 27
<211> LENGTH: 16
<212> TYPE: PRT
<213> ORGANISM: Homo sapiens

<400> SEQUENCE: 27

Leu Gly Ser Gly Ala Phe Gly Glu Val Tyr Glu Gly Gln Leu Gln Ala
1               5                   10                  15

<210> SEQ ID NO 28
<211> LENGTH: 19
<212> TYPE: PRT
<213> ORGANISM: Homo sapiens

<400> SEQUENCE: 28

Glu Asp Glu Ala Gln Pro Gln Arg Val Ala Ile Lys Ser Leu Arg Lys
1               5                   10                  15

Gly Ala Ser

<210> SEQ ID NO 29
<211> LENGTH: 58
<212> TYPE: PRT
<213> ORGANISM: Homo sapiens

<400> SEQUENCE: 29

Glu Phe Ala Glu Leu Leu Gln Glu Ala Gln Leu Met Ser Asn Phe Lys
1               5                   10                  15

His Glu Asn Ile Val Cys Leu Ile Gly Ile Cys Cys Asp Thr Asp Ser
            20                  25                  30

Ile Ser Leu Ile Met Glu His Met Glu Ala Gly Asp Leu Leu Ser Tyr
        35                  40                  45

Leu Arg Ala Ala Arg Pro Ser Ser Gln Glu
    50                  55

<210> SEQ ID NO 30
<211> LENGTH: 23
<212> TYPE: PRT
<213> ORGANISM: Homo sapiens

<400> SEQUENCE: 30

Ala Leu Ser Lys Leu Gln Leu Pro Glu Leu Leu Ser Met Cys Leu Asp
1               5                   10                  15

Val Ala Asn Gly Cys Ser Tyr
            20

<210> SEQ ID NO 31
<211> LENGTH: 139
<212> TYPE: PRT
<213> ORGANISM: Homo sapiens

<400> SEQUENCE: 31

Glu Asp Met His Phe Val His Arg Asp Leu Ala Cys Arg Asn Cys Leu
1               5                   10                  15

Val Ser Asp Gly Ala Ala Ile Gly Gly Arg Arg Ile Val Lys Ile Gly
            20                  25                  30

Asp Phe Gly Leu Ala Arg Asp Ile Tyr Lys Ser Asp Tyr Tyr Arg Lys
        35                  40                  45
```

Glu Gly Glu Gly Leu Leu Pro Val Arg Trp Met Ala Leu Glu Ser Leu
                50                  55                  60

Val Asp Gly Leu Phe Ser Thr Gln Ser Asp Val Trp Ala Phe Gly Val
 65                  70                  75                  80

Leu Cys Trp Glu Ile Phe Thr Leu Gly Gln Gln Pro Tyr Ala Ala Arg
                    85                  90                  95

Asn Asn Phe Glu Val Leu Ala His Val Lys Glu Gly Gly Arg Leu Gln
                100                 105                 110

Gln Pro Glu Arg Cys Pro Glu Lys Leu Tyr Ala Leu Leu Leu Gln Cys
                115                 120                 125

Trp Arg Ser Glu Pro Trp Glu Arg Pro Ser Phe
130                 135

<210> SEQ ID NO 32
<211> LENGTH: 22
<212> TYPE: PRT
<213> ORGANISM: Homo sapiens

<400> SEQUENCE: 32

Leu Gly Gln Gly Ser Phe Gly Met Val Tyr Glu Gly Val Ala Lys Gly
 1               5                  10                  15

Val Val Lys Asp Glu Pro
                20

<210> SEQ ID NO 33
<211> LENGTH: 72
<212> TYPE: PRT
<213> ORGANISM: Homo sapiens

<400> SEQUENCE: 33

Glu Thr Arg Val Ala Ile Lys Thr Val Asn Glu Ala Ala Ser Met Arg
 1               5                  10                  15

Glu Arg Ile Glu Phe Leu Asn Glu Ala Ser Val Met Lys Glu Phe Asn
                20                  25                  30

Cys His His Val Val Arg Leu Leu Gly Val Val Ser Gln Gly Gln Pro
                35                  40                  45

Thr Leu Val Ile Met Glu Leu Met Thr Arg Gly Asp Leu Lys Ser Tyr
 50                  55                  60

Leu Arg Ser Leu Arg Pro Glu Met
65                  70

<210> SEQ ID NO 34
<211> LENGTH: 45
<212> TYPE: PRT
<213> ORGANISM: Homo sapiens

<400> SEQUENCE: 34

Glu Asn Asn Pro Val Leu Ala Pro Pro Ser Leu Ser Lys Met Ile Gln
 1               5                  10                  15

Met Ala Gly Glu Ile Ala Asp Gly Met Ala Tyr Leu Asn Ala Asn Lys
                20                  25                  30

Phe Val His Arg Asp Leu Ala Ala Arg Asn Cys Met Val
                35                  40                  45

<210> SEQ ID NO 35
<211> LENGTH: 116
<212> TYPE: PRT
<213> ORGANISM: Homo sapiens

<400> SEQUENCE: 35

```
Ala Glu Asp Phe Thr Val Lys Ile Gly Asp Phe Gly Met Thr Arg Asp
  1               5                  10                 15

Ile Tyr Glu Thr Asp Tyr Tyr Arg Lys Gly Gly Lys Gly Leu Leu Pro
             20                  25                 30

Val Arg Trp Met Ser Pro Glu Ser Leu Lys Asp Gly Val Phe Thr Thr
             35                  40                 45

Tyr Ser Asp Val Trp Ser Phe Gly Val Val Leu Trp Glu Ile Ala Thr
 50                  55                  60

Leu Ala Glu Gln Pro Tyr Gln Gly Leu Ser Asn Glu Gln Val Leu Arg
 65                  70                  75                 80

Phe Val Met Glu Gly Gly Leu Leu Asp Lys Pro Asp Asn Cys Pro Asp
             85                  90                 95

Met Leu Phe Glu Leu Met Arg Met Cys Trp Gln Tyr Asn Pro Lys Met
            100                 105                110

Arg Pro Ser Phe
            115

<210> SEQ ID NO 36
<211> LENGTH: 22
<212> TYPE: PRT
<213> ORGANISM: Homo sapiens

<400> SEQUENCE: 36

Leu Gly Gln Gly Ser Phe Gly Met Val Tyr Glu Gly Asn Ala Arg Asp
  1               5                  10                 15

Ile Ile Lys Gly Glu Ala
             20

<210> SEQ ID NO 37
<211> LENGTH: 72
<212> TYPE: PRT
<213> ORGANISM: Homo sapiens

<400> SEQUENCE: 37

Glu Thr Arg Val Ala Val Lys Thr Val Asn Glu Ser Ala Ser Leu Arg
  1               5                  10                 15

Glu Arg Ile Glu Phe Leu Asn Glu Ala Ser Val Met Lys Gly Phe Thr
             20                  25                 30

Cys His His Val Val Arg Leu Leu Gly Val Val Ser Lys Gly Gln Pro
             35                  40                 45

Thr Leu Val Val Met Glu Leu Met Ala His Gly Asp Leu Lys Ser Tyr
 50                  55                  60

Leu Arg Ser Leu Arg Pro Glu Ala
 65                  70

<210> SEQ ID NO 38
<211> LENGTH: 45
<212> TYPE: PRT
<213> ORGANISM: Homo sapiens

<400> SEQUENCE: 38

Glu Asn Asn Pro Gly Arg Pro Pro Pro Thr Leu Gln Glu Met Ile Gln
  1               5                  10                 15

Met Ala Ala Glu Ile Ala Asp Gly Met Ala Tyr Leu Asn Ala Lys Lys
             20                  25                 30

Phe Val His Arg Asp Leu Ala Ala Arg Asn Cys Met Val
             35                  40                 45
```

<210> SEQ ID NO 39
<211> LENGTH: 115
<212> TYPE: PRT
<213> ORGANISM: Homo sapiens

<400> SEQUENCE: 39

```
Ala His Asp Phe Thr Val Lys Ile Gly Asp Phe Gly Met Thr Arg Asp
1               5                   10                  15

Ile Tyr Glu Thr Asp Tyr Tyr Arg Lys Gly Gly Lys Gly Leu Leu Pro
            20                  25                  30

Val Arg Trp Met Ala Pro Glu Ser Leu Lys Asp Gly Val Phe Thr Ser
        35                  40                  45

Ser Asp Met Trp Ser Phe Gly Val Val Leu Trp Glu Ile Thr Ser Leu
    50                  55                  60

Ala Glu Gln Pro Tyr Gln Gly Leu Ser Asn Glu Gln Val Leu Lys Phe
65                  70                  75                  80

Val Met Asp Gly Gly Tyr Leu Asp Gln Pro Asp Asn Cys Pro Glu Arg
                85                  90                  95

Val Thr Asp Leu Met Arg Met Cys Trp Gln Phe Asn Pro Lys Met Arg
                100                 105                 110

Pro Thr Phe
        115
```

<210> SEQ ID NO 40
<211> LENGTH: 177
<212> TYPE: DNA
<213> ORGANISM: synthetic construct
<220> FEATURE:
<221> NAME/KEY: CDS
<222> LOCATION: (1)..(177)

<400> SEQUENCE: 40

```
tcc ctt ggg ggc ttt gaa ata aca cca cca gtg gtc tta agg ttg aag        48
Ser Leu Gly Gly Phe Glu Ile Thr Pro Pro Val Val Leu Arg Leu Lys
1               5                   10                  15 tgt ggt tca ggg cca gtg cat att agt gga cag cac tta gta gtg tac        96
Cys Gly Ser Gly Pro Val His Ile Ser Gly Gln His Leu Val Val Tyr
            20                  25                  30 cgc cgg aag cac cag gag ctg caa gcc atg cag atg gag ctg cag agc       144
Arg Arg Lys His Gln Glu Leu Gln Ala Met Gln Met Glu Leu Gln Ser
        35                  40                  45 cct gag tac aag ctg agc aag ctc cgc acc tcg                           177
Pro Glu Tyr Lys Leu Ser Lys Leu Arg Thr Ser
    50                  55
```

<210> SEQ ID NO 41
<211> LENGTH: 59
<212> TYPE: PRT
<213> ORGANISM: synthetic construct

<400> SEQUENCE: 41

```
Ser Leu Gly Gly Phe Glu Ile Thr Pro Pro Val Val Leu Arg Leu Lys
1               5                   10                  15

Cys Gly Ser Gly Pro Val His Ile Ser Gly Gln His Leu Val Val Tyr
            20                  25                  30

Arg Arg Lys His Gln Glu Leu Gln Ala Met Gln Met Glu Leu Gln Ser
        35                  40                  45

Pro Glu Tyr Lys Leu Ser Lys Leu Arg Thr Ser
    50                  55
```

```
<210> SEQ ID NO 42
<211> LENGTH: 10
<212> TYPE: DNA
<213> ORGANISM: Homo sapiens

<400> SEQUENCE: 42
ggcgggatgg                                                          10

<210> SEQ ID NO 43
<211> LENGTH: 6
<212> TYPE: PRT
<213> ORGANISM: Homo sapiens
<220> FEATURE:
<221> NAME/KEY: misc_feature
<222> LOCATION: (2)
<223> OTHER INFORMATION: Xaa is any amino acid
<221> NAME/KEY: misc_feature
<222> LOCATION: (4)
<223> OTHER INFORMATION: Xaa is any amino acid
<221> NAME/KEY: misc_feature
<222> LOCATION: (5)
<223> OTHER INFORMATION: Xaa is any amino acid

<400> SEQUENCE: 43

Gly Xaa Gly Xaa Xaa Gly
1               5
```